(12) United States Patent
Rank et al.

(10) Patent No.: US 10,717,968 B2
(45) Date of Patent: *Jul. 21, 2020

(54) POLYMERASES FOR NUCLEOTIDE ANALOGUE INCORPORATION

(71) Applicant: Pacific Biosciences of California, Inc., Menlo Park, CA (US)

(72) Inventors: David R. Rank, Pacific Grove, CA (US); Paul S. Peluso, Newark, CA (US); David K. Hanzel, Palo Alto, CA (US); Geoff Otto, Brookline, MA (US); Thang Pham, Mountain View, CA (US); Fred Christians, Los Altos Hills, CA (US); Arekadiusz Bibillo, Cupertino, CA (US); Insil Park, Fremont, CA (US); Sonya Clark, Oakland, CA (US); John Lyle, Fremont, CA (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 28 days.

This patent is subject to a terminal disclaimer.

(21) Appl. No.: 15/894,157

(22) Filed: Feb. 12, 2018

(65) Prior Publication Data

US 2018/0237757 A1  Aug. 23, 2018

Related U.S. Application Data

(63) Continuation of application No. 15/370,461, filed on Dec. 6, 2016, now Pat. No. 9,951,321, which is a continuation of application No. 14/538,653, filed on Nov. 11, 2014, now Pat. No. 9,556,479, which is a continuation of application No. 11/645,223, filed on Dec. 21, 2006, now Pat. No. 8,921,086.

(60) Provisional application No. 60/753,670, filed on Dec. 22, 2005.

(51) Int. Cl.
| | |
|---|---|
| *C12N 9/12* | (2006.01) |
| *C12P 19/34* | (2006.01) |
| *C12Q 1/6827* | (2018.01) |
| *C12Q 1/6869* | (2018.01) |

(52) U.S. Cl.
CPC ............ *C12N 9/1252* (2013.01); *C12P 19/34* (2013.01); *C12Q 1/6827* (2013.01); *C12Q 1/6869* (2013.01); *C12Y 207/07007* (2013.01); *C07K 2319/20* (2013.01); *Y02P 20/52* (2015.11)

(58) Field of Classification Search
None
See application file for complete search history.

(56) References Cited

U.S. PATENT DOCUMENTS

| | | |
|---|---|---|
| 5,001,050 A | 3/1991 | Blanco et al. |
| 5,198,543 A | 3/1993 | Blanco et al. |
| 5,576,204 A | 11/1996 | Blanco et al. |
| 5,968,781 A | 10/1999 | Yoon et al. |
| 5,998,580 A | 12/1999 | Fay et al. |
| 6,607,883 B1 | 8/2003 | Frey et al. |
| 6,767,704 B2 | 7/2004 | Waldman et al. |
| 6,917,726 B2 | 7/2005 | Levene et al. |
| 7,033,764 B2 | 4/2006 | Korlach et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,361,466 B2 | 4/2008 | Korlach et al. |
| 7,405,281 B2 | 7/2008 | Xu et al. |
| 8,343,746 B2 | 1/2013 | Rank et al. |
| 8,906,660 B2 | 12/2014 | Kamtekar et al. |
| 9,296,999 B2 | 3/2016 | Kamtekar et al. |
| 9,399,766 B2 | 7/2016 | Kamtekar et al. |
| 9,476,035 B2 | 10/2016 | Kamtekar et al. |
| 2001/0031483 A1 | 10/2001 | Sorge et al. |
| 2003/0036181 A1 | 2/2003 | Okkels |
| 2003/0044781 A1 | 3/2003 | Korlach et al. |
| 2003/0087315 A1 | 5/2003 | Prockop et al. |
| 2003/0121854 A1 | 7/2003 | Reis |
| 2003/0140369 A1 | 7/2003 | Simmons |
| 2003/0152988 A1 | 8/2003 | Gelfand et al. |
| 2004/0018969 A1 | 1/2004 | Rosen et al. |
| 2004/0259082 A1 | 12/2004 | Williams |
| 2005/0009189 A1 | 1/2005 | Lechelt-Kunze et al. |
| 2005/0042633 A1 | 2/2005 | Williams |
| 2005/0187718 A1 | 8/2005 | Edwards et al. |

(Continued)

FOREIGN PATENT DOCUMENTS

| | | |
|---|---|---|
| WO | 2000053805 A1 | 9/2000 |
| WO | 2002029027 | 4/2002 |
| WO | 2002086088 A2 | 10/2002 |

(Continued)

OTHER PUBLICATIONS

Office Action dated Jun. 11, 2018 for related application No. CA 2,633,524.
Albà (2001) "Protein Family Review: Replicative DNA Polymerases." Genome Biology 2(1): reviews 3002.1-3002.4.
Albert et al (2005) "Structural Basis for Mambrane Anchorage of Viral f29 DNA during Replication." The Journal of Biological Chemistry, 280(52): 42486-42488.

(Continued)

*Primary Examiner* — Richard G Hutson
(74) *Attorney, Agent, or Firm* — Monica Elrod-Erickson

(57) ABSTRACT

Compositions that include polymerases with features for improving entry of nucleotide analogues into active site regions and for coordinating with the nucleotide analogues in the active site region are provided. Methods of making the polymerases and of using the polymerases in sequencing and DNA replication and amplification as well as kinetic models of polymerase activity and computer-implemented methods of using the models are also provided.

18 Claims, 19 Drawing Sheets
(5 of 19 Drawing Sheet(s) Filed in Color)

Specification includes a Sequence Listing.

(56) References Cited

U.S. PATENT DOCUMENTS

2007/0196846 A1    8/2007    Hanzel et al.

FOREIGN PATENT DOCUMENTS

| WO | 2004058987 | 7/2004 |
|---|---|---|
| WO | 2004092331 | 10/2004 |
| WO | 2007076057 A2 | 7/2007 |

OTHER PUBLICATIONS

Adelman et al. (2002) "Single Molecule Analysis of RNA Polymerase Elongation Reveals Uniform Kinetic Behavior." Proceedings of the National Academy of Sciences, USA, 99(21): 13538-13543.
Augustin et al. (2001) "Progress towards single-molecule sequencing: enzymatic synthesis of nucleotide-specifically labeled DNA." Journal of Biotechnology, 86(3): 289-301.
Benkovic and Schray (1973) "Chemical basis of biological phosphoryl transfer," in The Enzymes, Boyer (ed), 8:201-238, Academic Press, New York.
Bernad et al. (1990) "The highly conserved amino acid sequence motif Tyr-Gly-Asp-Thr-Asp-Ser in alpha-like DNA polymerases is required by phage phi 29 DNA polymerase for protein-primed initiation and polymerization." Proceedings of the National Academy of Sciences, USA, 87(12): 4610-4614.
Blanco and Salas (1996) "Relating Structure to Function in f29 DNA Polymerase." The Journal of Biological Chemistry, 271(15): 8509-8512.
Blanco et al. (1995) "Mutational Analysis of Bacterophage Phi DNA Polymerase." Methods of Enzimology, 262: 283-294.
Blasco et al. (1990) "Structural and functional analysis of temperature-senditive mutants of the phage f29 DNA polymerase." Nucleic Acids Research, 18(16): 4763-4770.
Blasco et al. (1992) "Phi 29 DNA polymerase active site. Mutants in conserved residues Tyr254 and Tyr390 are affected in dNTP binding." The Journal of Biological Chemistry, 267(27): 19427-19434.
Blasco et al. (1992) "Primer Terminus Stabilization at the f29 DNA Polymerase Active Site." The Journal of Biological Chemistry, 270(6): 2735-2740.
Blasco et al. (1992) "Structural and functional studies on f29 DNA polymerase." Chromosoma, 102: S32-S38.
Blasco et al. (1992) "f29 DNA Polymerase Active Site." The Journal of Biological Chemistry, 267(27): 19424-19434.
Blasco et al. (1992) "f29 DNA Polymerase Active Site." The Journal of Biological Chemistry, 268(32) 24106-24113.
Blasco et al. (1993) "Phi 29 DNA polymerase active site. Residue ASP249 of conserved amino acid motif 'Dx2SLYP' is critical for synthetic activities." J Biol Chem. 268(32):24106-13.
Blasco et al. (1993) "Phi 29 DNA polymerase active site. The conserved amino acid motif 'Kx3NSxYG' is involved in template-primer binding and dNTP selection." The Journal of Biological Chemistry, 268(22): 16763-16770.
Bonnin et al. (1999) "A Single Tyrosine Prevents Insertion of Ribonucleotides in the Eukaryotic-type f29 DNA Polymerase." The Journal of Molecular Biology, 290: 241-251.
Brueggemeier et al. (2003) "Protein-acrylamide Copolymer Hydrogels for Array-based Detection of Tryosine Kinase Activity from Cell Lysates." Biomacromolecules, 6(5): 2765-2775.
Burgers et al. (2001) "Eukaryotic DNA polymerases: proposal for a revised nomenclature." The Journal of Biological Chemistry. 276(47): 43487-43490.
Butz, et al. (2004) "Detection of allelic variations of human gene expression by polymerase colonies," BMC Genetics, 5:3.
Defour et al. (2000) "An Aspartic Acid residue in TPR-1, a Specific Region of Protein-priming DNA Polymerase, is Required for the Functional Interaction with Primer Terminal Protein." The Journal of Molecular Biology, 304: 289-300.

Defour et al. (2003) "A Conserved Insertion in Protein-primed DNA Polymerases is Involved in Primer Terminus Stabilisation." The Journal of Molecular Biology, 331: 781-794.
DeVega et al. (1996) "Primer-terminus stabilization at the 3'-5' exonuclease active site of f29 DNA polymerase. Involvement of two amino acid residues highly conserved in proofreading DNA polymerases." The EMBO Journal, 15(5): 1182-1192.
DeVega et al. (1997) "An Invariant Lysine Residue is Involved in Catalysis at the 3'5' Exonuclease Active Site of Eukaryotic-type DNA Polymerase." The Journal of Molecular Biology, 270: 65-78.
DeVega et al. (1998) "Mutational Analysis of f29 DNA Polymerase Residues Acting as ssDNa Ligands for 3'-5' Exonucleoysis." The Journal of Molecular Biology, 279: 807-822.
DeVega et al. (1998) "f29 DNA Polymerase Residue Ser122, a Single-stranded DNA Ligand for 3'=5' Exonucleoysis, Is Required to Interact with the Terminal Protein." The Journal of Biological Chemistry, 273(44): 28966-28977.
DeVega et al. (1999) "Processive Proofreading and the Spatial Relationship between Polymerase and Exonuclease Active Sites of Bacteriophage f29 DNA Polymerase." The Journal of Molecular Biology, 292: 39-51.
DeVega et al. (2000) "Phage f29 DNA Polymerase Residues Involved in the Proper Stabilisation of the Primer-terminus at the 3'-5' Exnuclease Active Site." The Journal of Molecular Biology, 304: 1-9.
Eger and Benkovic (1992) "Minimal kinetic mechanism for misincorporation by DNA polymerase I (Klenow fragment)," Biochemistry, 31(38):9227-9236.
Eisenbrandt et al. (2002) "f29 DNA polymerase residue Try59, His61 and Phe69 of the highly conserved ExoII motif are essential for interaction with the terminal protein." Nucleic Acids Research, 30(6): 1379-1386.
Esteban et al. (1993) "Fidelity of f29 DNA Polymerase." The Journal of Biological Chemistry, 268(4): 2719-2726.
Esteban et al. (1994) "3'-->5' exonuclease active site of phi 29 DNA polymerase. Evidence favoring a metal ion-assisted reaction mechanism." The Journal of Biological Chemistry, 269(50): 31946-31954.
Gardner and Jack (1999) "Determinants of nucleotide sugar recognition in an archaeon DNA polymerase." Nucleic Acids Research, 27(12): 2545-2553.
Gardner et al. (2004) "Comparative Kinetics of Nucleotide Analog Incorporation by Vent DNA Polymerase." The Journal of Biological Chemistry, 279(12): 11834-11842.
Gerlach, et al. (2001) "Purification and Characterization of polk, a DNA Polymerase Encoded by the Human DINB1 Gene," J. Biol. Chem., 276:92-98.
Giller et al. (2003) "Incorporation of reporter molecule-labeled nucleotides by DNA polymerases. I. Chemical synthesis of various reporter group-labeled 2'-deoxyribonucleoside-5'-triphosphates." Nucleic Acids Research, 31(10): 2630-2635.
Hübscher et al. (2002) "Eukaryotic DNA Polymerases." Annual Review of Biochemistry, vol. 71: 133-163.
Illana et al. (1998) "The RGD Sequence in Phage f29 Terminal Protein Is Required for Interaction with f29 DNA Polymerase." Virology, 248: 12-19.
Illana et al. (1999) "Phage f29 Terminal Protein Residues Asn80 and Try82 Are Recognition Elements of the Replication Origins." The Journal of Biological Chemistry, 274(21): 15073-15079.
Inoue et al. (2006) "Improvements of rolling circle amplification (RCA) efficiency and accuracy using Thermus thermophilus SSB mutant protein." Nucleic Acids Research, 34(9): e69.
Kamtekar et al. (2004) "Insights into Strand Displacement and Processivity from the Crystal Structure of the Protein-Prined DNA Polymerase of Bacteriophage f29." Molecular Cell, 16: 609-618.
Kamtekar et al. (2006) The f29 DNA polmerase protein-primer structure suggests a model for the initiation to elongation transition. The EMBO Journal, 25(6): 1335-1343.
Levene et al. (2003) "Zero-Mode Waveguides for Single-Molecule Analysis at High Concentrations." Science, 299(5607): 682-686.
Longás et al. (2006) "Functional characterization of highly processive protein-primed DNA polymerase from phages Nf and GA-1, endowed with a potent strand displacement capacity." Nucleic Acids Research, 34(20): 6051-6063.

(56) References Cited

OTHER PUBLICATIONS

Meijer et al. (2001) "Phi 29 Family of Phages." Microbiology and Molecular Biology Reviews, 65(2): 261-287.
Méndez et al. (1994) "Primer-terminus Stabilization at the f29 DNA Polymerase Active Site." The Journal of Biological Chemistry, 269(47): 30030-30038.
Méndez et al. (1997) "Protein-primed DNA replication: a transition between two modes of priming by a unique DNA polymerase." The EMBO Journal, 16(9): 2519-2527.
Miyazaki et al. (2005) "Efficient Immobilization of Enzymes on Microchannel Surface Through His-Tag and Applications for Microreactor." Protein and Peptide Letters, 12(2): 207-210.
Mizrahi et al. (1985) "Rate-limiting steps in the DNA polymerase I reaction pathway,"Biochemistry, 24(15):4010-4018.
Ngo et al. (1994) "The Protein Folding Problem and Tertiary Structure Prediction." Chapter 14, Birkhauser, Boston, MA pp. 433 & 492-495.
Office Action dated Jun. 7, 2019 for related application No. CA 2,633,524.
Nieba et al. (1997) "BIACORE Analysis of Histidine-tagged Proteins Using a Chelating NTA Sensor Chip." Analytical Biochemistry, 252: 217-228.
Nisson et al. (1997) "Heat-mediated Activation of Affinity-immobilized Taq DNA Polymerase." BioTechniques, 22(4): 744-751.
Patel et al. (1991) "Pre-steady-state kinetic analysis of processive DNA replication including complete characterization of an exonuclease-deficient mutant" Biochemistry 30(2):511-525.
Pérex-Arnaiz et al. (2006) "Invlovement of f29 DNA polymerase thumb subdomain in the proper coordination of synthesis and degradation during DNA replication." Nucleic Acids Research, 34(10): 3107-3115.
Ried et al. (1992) "Simultaneous visualization of seven different DNA probes by in situ hybridization using combinatorial fluorescence and digital imaging microscopy." Proceedings of the National Academy of Sciences, USA, 89(4): 1388-1392.
Rodríguez et al. (2003) "f29 DNA Polymerase Residue Phe128 of the Highly Conserved (S/T)Lx2h Motif is Required for a Stable and Functional Interaction with the Terminal Protein." The Journal of Molecular Biology, 325: 85-97.
Rodríguez et al. (2004) "f29 DNA Polymerase—Terminal Protein Interaction, Involvement of Residues Specifically Conserved Among Protein-primed DNA Polymerases." The Journal of Molecular Biology, 337: 829-841.
Rodríguez et al. (2005) "A specific subdomain in f29 DNA poymarase confers both processivity and strand-displacement capacity." The Proceedings of the National Academy of Sciences, USA, 102: 6407-6412.
Salas et al. (1990) "Structure and Function of the Bacteriophage f29 Replication Proteins." Molecular Mechanisms in DNA Replication, pp. 277-288.
Saturno et al. (1995) "A Novel Kinetic Analysis to Calculate Nucleotide Affinity of Proofreading DNA Polymerases." The Journal of Biological Chemistry, 270(52): 31235-31243.
Saturno et al. (1997) "f29 DNA Polymerase as a Residue Lys383, Invariant at Motif B of DNA-dependent Polymerases, is involved in dNTP Binding." The Journal of Molecular Biology, 269: 313-325.
Saturno et al. (1998) "Role of the First Asparate Residue of the 'YxDTDS' Motif of f29 DNA Polymerase as a Metal Ligand during both TP-primed and DNA-primed DNA Synthesis." The Journal of Molecular Biology, 283: 633-642.
Soengas et al. (1992) "Site-directed mutagenesis at the Exo III motif of f29 DNA polymerase; overlapping and strand-displacement activities." The EMBO Journal, 11(11): 4227-4237.
Steitz (1999) "DNA polymerases: structural diversity and common mechanisms." The Journal of Biological Chemistry, 274(25): 17395-17398.
Steitz (2006) "Visualizing polynucleotide polymerase machines at work." The EMBO Journal, 25(15): 3458-3468.
Tonon et al. (2000) "Spectral karyotyping combined with locus-specific FISH simultaneously defines genes and chromosomes involved in chromosomal translocations." Genes, Chromosomes & Cancer, 27: 418-423.
Truniger et al. (2002) "A positively charged residue of f29 DNA polymerase, highly conserved in DNA polymerase from families A and B, is involved in binding the incoming nucleotide." Nucleic Acids Research, 30(7): 1483-1492.
Truniger et al. (2003) "f29 DNA Polymerase Residue Leu384, Highly Conserved in Motif B of Eukaryotic Type DNA Replicases, Is Involved in Nucleotide Insertion Fidelity." The Journal of Biological Chemistry, 278(35): 33482-33491.
Truniger et al. (2004) "Function of the C-terminus of f29 DNA polymerase in DNA and terminal protein binding." Nucleic Acids Research, 32(1): 361-370.
Truniger et al. (2004) "Two Positively Charged Residues of φ29 DNA Polymerase, Conserved in Protein-primed DNA Polymerases, are Involved in Stabilisation of the Incoming Nucleotide." Journal of Molecular Biology, 335(2): 481-494.
Truniger et al. (2005) "Involvement if the 'linker' region between the exonuclease and polymerization domains of f29 DNA polymerase in DNA and TP binding." Gene, 348: 89-99.
Tsai and Johnson (2006) "A new paradigm for DNA polymerase specificity," Biochemistry, 45(32):9675-9687.
Vega et al. (1996) "Primer-terminus stabilization at the 3'-5' exonuclease active site of phi29 DNA polymerase. Involvement of two amino acid residues highly conserved in proofreading DNA polymerases." EMBO Journal, 15(5): 1182-1192.
Vega et al. (1998) Phi 29 DNA Polymerase residue SER122, a single-stranded DNA ligand for 3'-5' exonucleolysis, is required to interact with the terminal protein. J. Biol. Chem. 273(44): 28966-28977.
Wilfried et al. (2001) "f29 Family of Phages," Microbiology and Molecular Biology Reviews, 65: 261-287.
Yu et al. (1994) "Cyanine dye dUTP analogs for enzymatic labeling of DNA probes." Nucleic Acids Research, 22(15): 3226-3232.
Zakharova et al. (2004) "The Activity of Selected RB69 DNA Polymerase Mutants Can Be Restored by Manganese Ions: The Existence of Alternative Metal Ion Ligands Used during the Polymerization Cycle," Biochemistry, 43(21):6587-6595.
Zhu and Waggoner (1997) "Molecular mechanism controlling the incorporation of fluorescent nucleotides into DNA by PCR." Cytometry, 28: 206-211.
Zhu et al. (1994) "Directly labeled DNA probes using fluorescent nucleotides with different length linkers." Nucleic Acids Research, 22(16): 3418-3422.
European Search Report dated Feb. 1, 2010 for related application No. EP 06848948.3.
Office Action dated Aug. 1, 2013 for related application No. IN 3163/CHENP/2008.
Office Action dated Aug. 16, 2011 for related application No. AU 2006330947.
Office Action dated Jun. 14, 2013 for related application No. CA 2,633,524.
Office Action dated Mar. 26, 2013 for related application No. IN 3163/CHENP/2008.
Office Action dated May 13, 2011 for related application No. AU 2006331512.
Office Action dated Nov. 1, 2011 for related application No. CN 200680052606.3.
Office Action dated Nov. 10, 2010 for related application No. CN 200680052606.3.
Office Action dated Sep. 28, 2012 for related application No. EP 06848948.3.
Office Action dated Apr. 25, 2014 for related application No. CA 2,633,524.
Office Action dated Feb. 3, 2015 for related application No. CA 2,633,524.
Office Action dated Apr. 29, 2016 for related application No. CA 2,633,524.
European Search Report Jun. 8, 2016 for related application No. EP 16157104.7.

(56) References Cited

OTHER PUBLICATIONS

Office Action dated Jul. 4, 2017 for related application No. CA 2,633,524.

```
Phi29  TYIQDIYMKEVD-GKLVEGSPDDYTDIKFSVKCAGM
B103   TYIQDIYAKEVD-GKLIECSPDEATTTKFSVKCAGM
PZA    TYIQDIYMKEVD-GKLVEGSPDDYTTIKFSVKCAGM
M2     TYIQDIYVKEVD-GKLKECSPDEATTTKFSVKCAGM
G1     TYFIETTWKENDKGKLVVCEPQDATKVKPKIACAGM
cp-1   LYIEELIQEDGT------------------THLDVKGAGM
```

505-525 domain

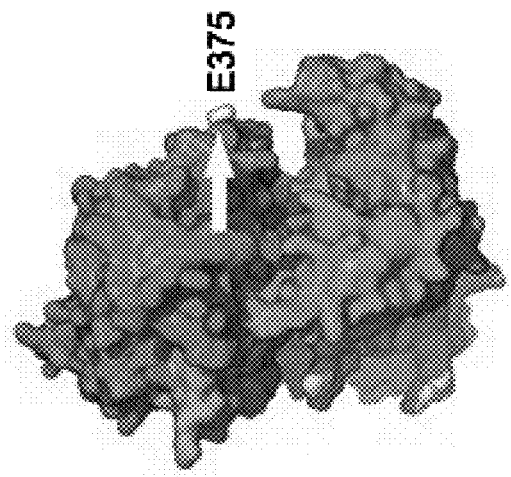
Fig. 3D
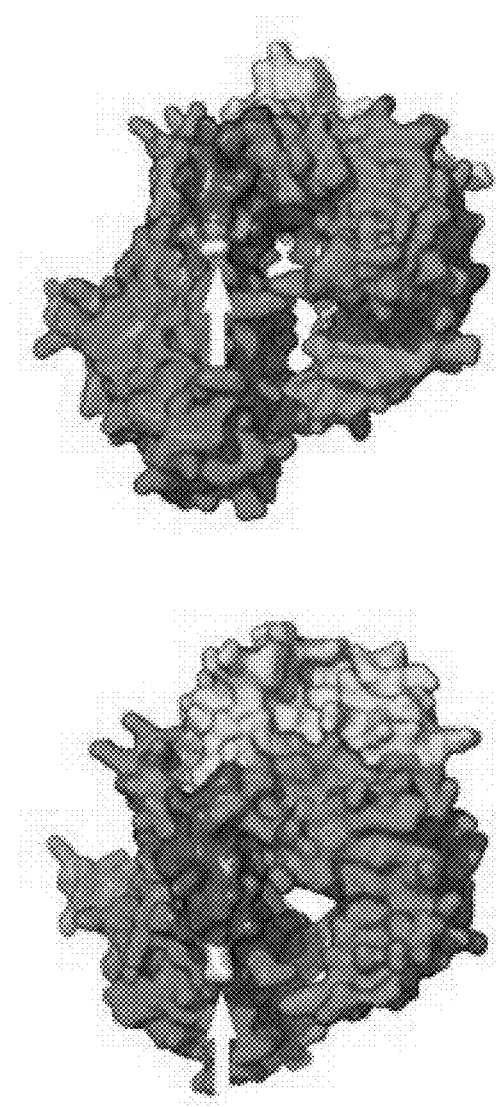
Fig. 3C
Fig. 3B
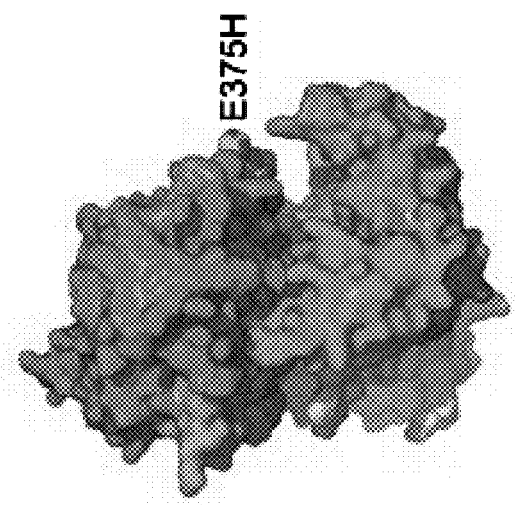
Fig. 3G
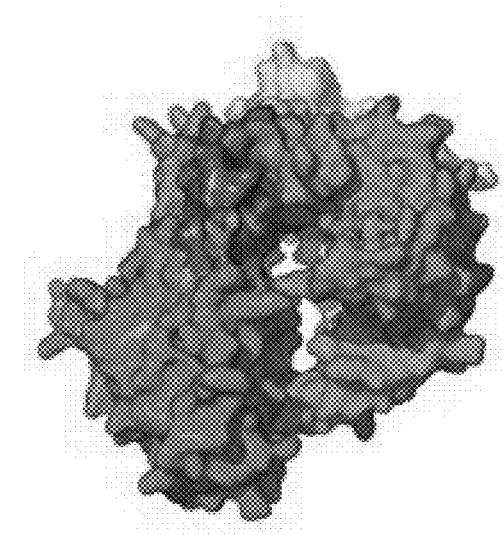
Fig. 3F
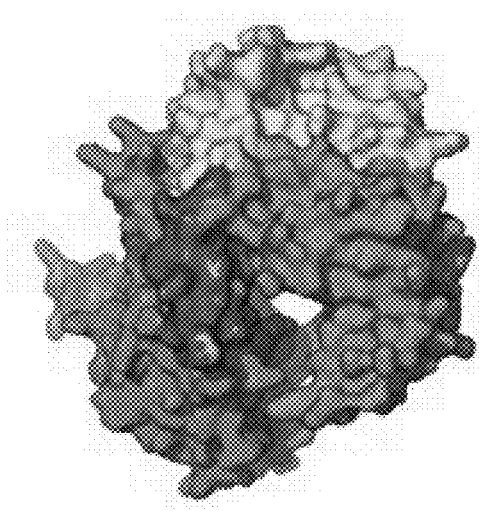
Fig. 3E

| | |
|---|---|
| Phi29 | GYWAHESTFKRAK |
| B103 | GYWAHESTFKRAK |
| PZA | GYWAHESTFKRAK |
| M2 | GYWAHESTFKRAK |
| G1 | GYWDHEATFQRAR |
| cp-1 | GKWAHEGRAVKAK |

| | |
|---|---|
| Phi29 | VKKIAKDFKL |
| B103  | VKKIAKDFQL |
| PZA   | VKKIAKDFKL |
| M2    | VKKIAKDFQL |
| G1    | VEQIAKGFGL |
| cp-1  | IATMAGLFKM |

Fig. 6A

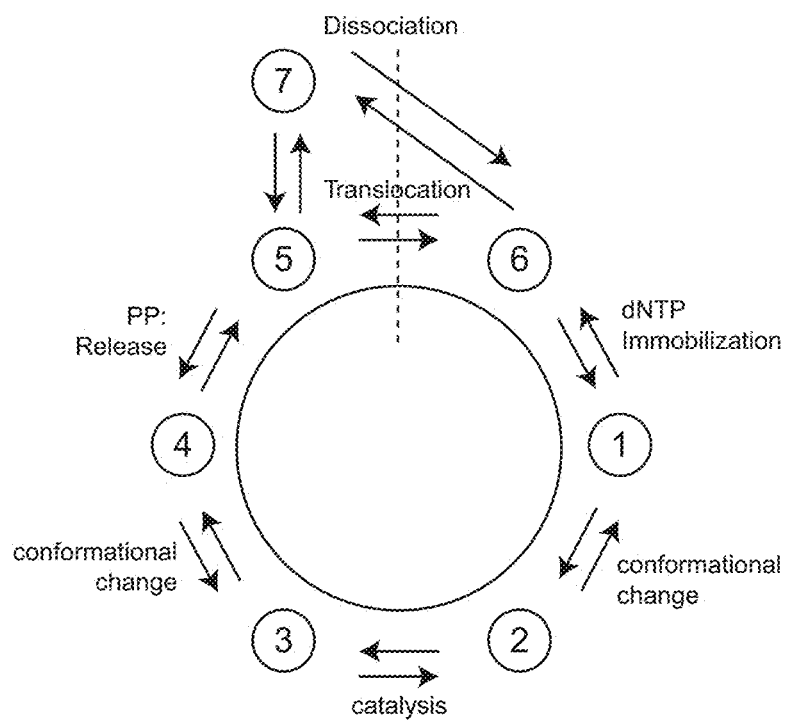
Fig 10C
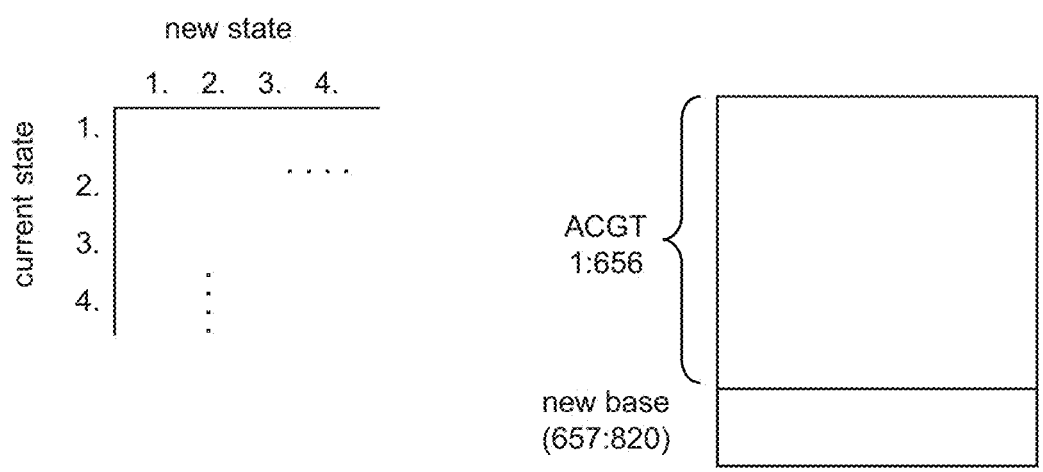
Fig 10D
Fig 10E

POLYMERASES FOR NUCLEOTIDE ANALOGUE INCORPORATION

CROSS-REFERENCE TO RELATED APPLICATIONS

This application is a continuation of U.S. patent application Ser. No. 15/370,461, filed Dec. 6, 2016, which is a continuation of U.S. patent application Ser. No. 14/538,653, filed Nov. 11, 2014, now U.S. Pat. No. 9,556,479, which is a continuation of U.S. patent application Ser. No. 11/645,223, filed Dec. 21, 2006, now U.S. Pat. No. 8,921,086, which claims priority to and benefit of U.S. Provisional Patent Application No. 60/753,670, filed Dec. 22, 2005. Each of these applications is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under NHGRI Grant No. R01 HG003710-01 awarded by the National Human Genome Research Institute (NHGRI) of the National Institutes of Health (NIH). The government has certain rights in the invention. The preceding statement is included in accordance with 37 C.F.R. 401.14(f)(4) because one or more inventions described herein were made or developed with government grant support. This statement should not be construed as necessarily covering all inventions described herein.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 186 KB file (01001305_2018-05-03_SequenceListing.txt).

FIELD OF THE INVENTION

The invention relates to polymerases with features for improving entry of nucleotide analogues into active site regions and for coordinating with the nucleotide analogues in the active site region. Methods of making the polymerases and of using the polymerases in sequencing and DNA replication and amplification, as well as kinetic models of polymerase activity and computer-implemented methods of using the models, are also described.

BACKGROUND OF THE INVENTION

DNA polymerases replicate the genomes of living organisms. In addition to this central role in biology, DNA polymerases are also ubiquitous tools of biotechnology. They are widely used, e.g., for reverse transcription, amplification, labeling, and sequencing, which are central technologies for a variety of applications such as sequencing, nucleic acid amplification, cloning, protein engineering, diagnostics, molecular medicine and many other technologies.

Because of the significance of DNA polymerases, they have been extensively studied. This study has focused, e.g., on phylogenetic relationships among polymerases, structure of polymerases, structure-function features of polymerases, and the role of polymerases in DNA replication and other basic biology, as well as ways of using DNA polymerases in biotechnology. For a review of polymerases, see, e.g., Hübscher et al. (2002) EUKARYOTIC DNA POLYMERASES *Annual Review of Biochemistry* Vol. 71: 133-163; Alba (2001) "Protein Family Review: Replicative DNA Polymerases" *Genome Biology* 2(1):reviews 3002.1-3002.4; Steitz (1999) "DNA polymerases: structural diversity and common mechanisms" *J Biol Chem* 274:17395-17398 and Burgers et al. (2001) "Eukaryotic DNA polymerases: proposal for a revised nomenclature" *J Biol Chem.* 276(47): 43487-90. Crystal structures have been solved for many polymerases, which often share a similar architecture. The basic mechanisms of action for many polymerases have been determined.

A fundamental application of DNA technology involves various labeling strategies for labeling a DNA that is produced by a DNA polymerase. This is useful in microarray technology, DNA sequencing, SNP detection, cloning, PCR analysis, and many other applications. Labeling is often performed in various post-synthesis hybridization or chemical labeling schemes, but DNA polymerases have also been used to directly incorporate various labeled nucleotides in a variety of applications, e.g., via nick translation, reverse transcription, random priming, amplification, the polymerase chain reaction, etc. See, e.g., Giller et al. (2003) "Incorporation of reporter molecule-labeled nucleotides by DNA polymerases. I. Chemical synthesis of various reporter group-labeled 2'-deoxyribonucleoside-5'-triphosphates" *Nucleic Acids Res.* 31(10): 2630-2635; Augustin et al. (2001) "Progress towards single-molecule sequencing: enzymatic synthesis of nucleotide-specifically labeled DNA" *J. Biotechnol.*, 86:289-301; Tonon et al. (2000) "Spectral karyotyping combined with locus-specific FISH simultaneously defines genes and chromosomes involved in chromosomal translocations" *Genes Chromosom. Cancer* 27:418-423; Zhu and Waggoner (1997) "Molecular mechanism controlling the incorporation of fluorescent nucleotides into DNA by PCR." *Cytometry*, 28:206-211. Yu et al. (1994) "Cyanine dye dUTP analogs for enzymatic labeling of DNA probes" *Nucleic Acids Res.*, 22:3226-3232; Zhu et al. (1994) "Directly labeled DNA probes using fluorescent nucleotides with different length linkers." *Nucleic Acids Res.* 22:3418-3422; Ried et al. (1992) "Simultaneous visualization of seven different DNA probes by in situ hybridization using combinatorial fluorescence and digital imaging microscopy" *Proc. Natl Acad. Sci. USA*, 89:1388-1392.

DNA polymerase mutants have been identified that have altered nucleotide analogue incorporation properties relative to wild-type counterpart enzymes. For example, Vent$^{A488L}$ DNA polymerase can incorporate certain non-standard nucleotides with a higher efficiency than native Vent DNA polymerase. See Gardner et al. (2004) "Comparative Kinetics of Nucleotide Analog Incorporation by Vent DNA Polymerase" *J. Biol. Chem.*, 279(12), 11834-11842; Gardner and Jack "Determinants of nucleotide sugar recognition in an archaeon DNA polymerase" *Nucleic Acids Research*, 27(12) 2545-2553. The altered residue in this mutant, A488, is predicted to be facing away from the nucleotide binding site of the enzyme. The pattern of relaxed specificity at this position roughly correlates with the size of the substituted amino acid side chain and affects incorporation by the enzyme of a variety of modified nucleotide sugars.

The ability to improve specificity, processivity, or other features of DNA polymerases towards labeled nucleotide analogues would be highly desirable in a variety of contexts where, e.g., nucleic acid labeling is desired, including DNA amplification, sequencing, labeling, detection, cloning, and many others. The present invention provides new DNA polymerases with modified properties for labeled nucleotide analogues, methods of making such polymerases, methods of using such polymerases, and many other features that will become apparent upon a complete review of the following.

SUMMARY OF THE INVENTION

The invention includes polymerases that incorporate nucleotide analogues, such as phosphate analogues, into a growing template copy, during DNA amplification. Without being bound to any particular theory of operation, these polymerases are optionally modified such that the active site of the polymerase is modified to reduce steric entry inhibition of the analogue into the active site and/or to provide complementarity with one or more non-natural features of the nucleotide analogue. Such polymerases are particularly well-suited for DNA amplification and/or sequencing applications, including real-time applications, e.g., in the context of amplification or sequencing protocols that include incorporation of analogue residues into DNA by the polymerase. The analogue residue that is incorporated can be the same as a natural residue, e.g., where a label or other moiety of the analogue is removed by action of the polymerase during incorporation, or the analogue residue can have one or more feature that distinguishes it from a natural nucleotide residue.

Accordingly, the invention includes compositions that include a recombinant DNA polymerase. The recombinant DNA polymerase includes a modified active site region that is homologous to a wild-type active site region of a wild-type DNA polymerase. The modified active site region includes one or more structural modifications relative to the wild type active site region that improve the desired activity of the enzyme, e.g., toward naturally occurring nucleotides and/or nucleotide analogues. In certain aspects, and without being bound to a particular theory of operation, such modifications include those that reduce steric inhibition for entry of a natural nucleotide or nucleotide analogue into the modified active site region and/or that make the active site region complementary with one or more non-natural features of the natural nucleotide and/or nucleotide analogue. The recombinant DNA polymerase displays a modified property for the nucleotide analogue as compared to the wild-type polymerase.

A variety of DNA polymerases are optionally modified to include the modified active site region. For example, the recombinant DNA polymerase is optionally homologous to a Φ29 DNA polymerase or mutant thereof, a Taq polymerase, an exonuclease deficient Taq polymerase, a DNA Pol I polymerase, a T7 polymerase, an RB69 polymerase, a T5 polymerase, or a polymerase corresponding to a Klenow fragment of a DNA Pol I polymerase. For example, the recombinant DNA polymerase can be homologous to a wild-type or exonuclease deficient Φ29 DNA polymerase, e.g., as described in U.S. Pat. Nos. 5,001,050, 5,198,543, or 5,576,204. Similarly, the recombinant DNA polymerase can be homologous to Φ29, B103, GA-1, PZA, Φ15, BS32, M2Y, Nf, G1, Cp-1, PRD1, PZE, SF5, Cp-5, Cp-7, PR4, PR5, PR722, or L17, or the like. For nomenclature, see also, Meijer et al. (2001) "Φ29 Family of Phages" *Microbiology and Molecular Biology Reviews*, 65(2):261-287.

The modified active site region can include any of a variety of different modifications to reduce steric inhibition and/or to make the region complementary with one or more non-natural features of the nucleotide analogue. For example, structural modifications within or proximal to the active site relative to the wild-type Φ29 DNA polymerase are selected from: a Δ505-525 deletion, a deletion within Δ505-525, a K135A mutation, an L384R mutation in combination with another mutation herein (when an L384R mutation is present, it will generally be in combination with one or more additional mutation that reduces steric inhibition for entry of the nucleotide analogue), an E375H mutation, an E375S mutation, an E375K mutation, an E375R mutation, an E375A mutation, an E375Q mutation, an E375W mutation, an E375Y mutation, an E375F mutation, an E486A mutation, an E486D mutation, a K512A mutation, and combinations thereof. The polymerase can also include an additional mutation or combination of mutations selected from those listed in Table 8.

The polymerase optionally further includes one or more mutations/deletions relative to the wild-type polymerase that reduce or eliminate endogenous exonuclease activity. For example, relative to the wild-type Φ29 DNA polymerase, N62 is optionally mutated or deleted to reduce exonuclease activity; e.g., the polymerase can include an N62D mutation. Other example mutations that reduce exonuclease activity include: D12A, T15I, E14I, and/or D66A; accordingly, the polymerases of the invention optionally comprise one or more of these mutations.

The recombinant DNA polymerase optionally includes additional features exogenous or heterologous to a corresponding DNA polymerase such as a wild-type or nuclease deficient polymerase. For example, the recombinant polymerase optionally includes one or more exogenous affinity tags, e.g., purification or substrate binding tags, such as a 6 His tag sequence, a GST tag, an HA tag sequence, a plurality of 6 His tag sequences, a plurality of GST tags, a plurality of HA tag sequences, a SNAP-tag, or the like. These may be inserted into any of a variety of positions within the protein, and are preferably at one or more termini, e.g., C terminus or N terminus of the protein, and are more preferably, at the terminus that is most distal to the active site in the 3D structure of the protein.

Example polymerases of the invention include those listed in Table 3.

The compositions optionally include the nucleotide analogue. Example nucleotide analogues include those that include fluorophore and/or dye moieties. For example, the nucleotide analogue can be a labeled nucleotide, e.g., a base, sugar and/or phosphate labeled nucleotide. The analogue can be a mono-deoxy or a dideoxy nucleotide analogue.

One example class of nucleotide analogues are phosphate-labeled nucleotide analogues, including mono-deoxy phosphate-labeled nucleotide analogues and/or dideoxy phosphate-labeled nucleotide analogues. For example, the nucleotide analogue can be a labeled nucleotide analogue having from 3 to 6 phosphate groups (e.g., where the nucleotide analogue is a triphosphate, a tetraphosphate, a pentaphosphate or a hexaphosphate).

For example, the composition can include a labeled compound of the formula:

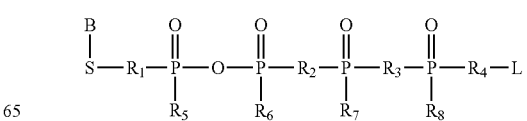

wherein B is a nucleobase (note that B optionally includes a label); S is selected from a sugar moiety, an acyclic moiety or a carbocyclic moiety (note that S optionally includes a label); L is an optional detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, C(OH)CH$_2$R where R is 4-pyridine or 1-imidazole, provided that $R_4$ may additionally be selected from

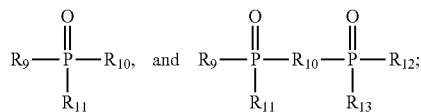

$R_5$, $R_6$, $R_7$, $R_8$, $R_{11}$ and $R_{13}$ are, when present, each independently selected from O, BH$_3$, and S; and $R_9$, $R_{10}$ and $R_{12}$ are independently selected from O, NH, S, methylene, substituted methylene, CNH$_2$, CH$_2$CH$_2$, C(OH)CH$_2$R where R is 4-pyridine or 1-imidazole. In some cases, phosphonate analogs may be employed as the analogs, e.g., where one of $R_2$, $R_3$, $R_4$, R9, R10 or R12 are not O, e.g., they are methyl etc.

The recombinant DNA polymerase displays a modified property for the nucleotide analogue as compared to the wild-type polymerase. For example, the modified property can be, e.g., $K_m$, $k_{cat}$, $V_{max}$, recombinant polymerase processivity in the presence of the nucleotide analogue (or of a naturally occurring nucleotide), average template read-length by the recombinant polymerase in the presence of the nucleotide analogue, specificity of the recombinant polymerase for the nucleotide analogue, rate of binding of the nucleotide analogue, rate of product (pyrophosphate, triphosphate, etc.) release, and/or branching rate. In one desirable embodiment, the modified property is a reduced $K_m$ for the nucleotide analogue and/or an increased $k_{cat}/K_m$ or $V_{max}/K_m$ for the nucleotide analogue. Similarly, the recombinant polymerase optionally has an increased rate of binding of the nucleotide analogue, an increased rate of product release, and/or a decreased branching rate, as compared to the wild-type polymerase.

At the same time, the recombinant DNA polymerase can incorporate natural nucleotides (e.g., A, C, G and T) into a growing copy nucleic acid. For example, the recombinant polymerase optionally displays a specific activity for a natural nucleotide that is at least about 5% as high (e.g., 5%, 10%, 25%, 50%, 75%, 100% or higher), as a corresponding wild-type polymerase and a processivity with natural nucleotides in the presence of a template that is at least 5% as high (e.g., 5%, 10%, 25%, 50%, 75%, 100% or higher) as the wild-type polymerase in the presence of the natural nucleotide. Optionally, the recombinant polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

The nucleotide analogue and a DNA template are optionally included in compositions of the invention, e.g., in which the recombinant polymerase incorporates the nucleotide analogue into a copy nucleic acid in response to the template DNA. The template DNA can be linear or circular DNA, and in certain sequencing applications is desirable a circular template. Thus, the composition can be present in a DNA amplification and/or sequencing system. Optionally, in one class of embodiments, the sequencing system comprises a Zero Mode Waveguide.

Methods of making and using the compositions are also features of the invention. For example, in one aspect, methods of making a DNA e.g., comprising one or more nucleotide analogue residues are provided. In these methods, a reaction mixture is provided. The reaction mixture typically includes those components that can at least partially replicate a template, e.g., a template, nucleotides, the polymerase and a replication initiating moiety that complexes with the template, or is integral to it, to prime the polymerase. The replication initiating moiety in this context is any moiety that can serve as a site to initiate the polymerase, e.g., a separate oligonucleotide complementary to the template, a hairpin or other self-complementary region of a template (e.g., a hairpin in a single-stranded template), a terminal protein, or the like. The polymerase is a recombinant polymerase capable of at least partially replicating the template in a template-dependent polymerase extension reaction (e.g., using the replication initiation moiety as a site of initiation). Typically, the one or more nucleotides comprise a nucleotide analogue. In preferred aspects, at least one, preferably two or more, three or more or at least four nucleotides are nucleotide analogues. The recombinant DNA polymerase has a modified active site (a region of the polymerase that, when modified, results in an alteration in an activity of the polymerase) that is homologous to a wild-type active site of a wild-type DNA polymerase. As discussed in the context of the compositions above, the modified active site can include one or more structural modification relative to the wild type active site that improves the activity of the enzyme toward one or more natural nucleotides and/or nucleotide analogues. In at least one example, and without being bound to any particular theory of operation, the modification to the active site reduces steric inhibition for entry of the nucleotide analogue into the modified active site and/or the modification is complementary with one or more non-natural features of the nucleotide analogue.

The mixture is reacted such that the recombinant polymerase replicates at least a portion of the template in a template-dependent manner, whereby at least one nucleotide analogue residue is incorporated into the resulting DNA. Incorporation of the analogue can result in the incorporation of a non-standard residue into the extended DNA (e.g., as a labeled nucleotide residue), or action of the polymerase can modify the analogue such that the nucleotide analogue residue incorporated into the extended DNA is structurally the same as a standard nucleotide residue. For example, in the latter embodiment, a variety of labels are cleaved by action of the polymerase, e.g., certain phosphate labels discussed in more detail herein are cleaved from the nucleotide analogue as it is incorporated into the growing DNA (typically providing a signal upon release of the label).

In a related class of methods, a reaction mixture is provided that includes a template, a replication initiating moiety, a template-dependent recombinant polymerase and one or more nucleotides. The one or more nucleotides include a phosphate labeled nucleotide. A $K_m$ value of the recombinant polymerase for the nucleotide analogue is lower than a $K_m$ for a corresponding homologous wild-type polymerase for the nucleotide analogue. The mixture is reacted such that the polymerase at least partially replicates the template in a template-dependent manner, e.g., whereby at least one nucleotide analogue residue is incorporated into the resulting DNA. As noted previously, once incorporated, the residue can be the same as a natural nucleotide residue, or can be different from a natural nucleotide residue.

In another related class of methods of making a DNA, a reaction mixture that includes a template, a replication initiating moiety that complexes with or is integral to the template, a polymerase capable of replicating at least a portion of the template using the moiety in a template-dependent polymerase extension reaction, and one or more nucleotide is provided. Here again, the one or more nucleotide typically includes a labeled phosphate nucleotide analogue. The polymerase in this class of embodiments is homologous to a Φ29 DNA polymerase. The polymerase has a $K_m$ for 488dC4P, A568dC4P, or both, that is less than about 75% of a $K_m$ of a GST-N62D Φ29 DNA polymerase for 488dC4P, A568dC4P or both. For example, the $K_m$ for 488dC4P, A568dC4P can be about 40% or less than GST-N62D Φ29 DNA polymerase, or, e.g., about 15% or less. The mixture is reacted such that the polymerase replicates at least a portion of the template.

The polymerases used in the methods can be any of those noted above with reference to the compositions. The properties of the polymerases used in the methods can be any of those noted in reference to compositions. For example, the polymerase optionally has a $k_{cat}/K_m$ for the nucleotide analogue that is higher than a $k_{cat}/K_m$ of a wild-type Φ29 for the nucleotide analogue. Similarly, the nucleotide analogues used in the methods can be any of those noted in reference to the compositions herein. The recombinant polymerases herein can have a $K_m$ for the nucleotide analogue that is e.g., about 90% as high, about 80% as high, about 75% as high, about 60% as high, about 50% as high, about 40% as high, about 25% as high, about 15% as high, about 10% as high, or less than about 5% as high as a $K_m$ of a naturally occurring polymerase homologous to the recombinant polymerase. The recombinant polymerase optionally has an increased rate of binding of the nucleotide analogue, an increased rate of product release, and/or a decreased branching rate, as compared to the corresponding wild-type polymerase.

In addition to methods of using the compositions herein, the present invention also includes methods of making the compositions. For example, in one aspect, a method of making a recombinant DNA polymerase (e.g., any of those discussed with respect to the compositions herein) is provided. For example, the methods can include structurally modeling a first polymerase, e.g., using any available crystal structure and molecular modeling software or system. Based on the modeling, one or more steric inhibition feature or complementarity feature affecting nucleotide access to the active site and/or binding of a nucleotide analogue within the active site region is identified, e.g., in the active site or proximal to it. The first DNA polymerase is mutated to reduce or remove at least one steric inhibition feature or to add the complementarity feature.

The method can additionally include screening or other protocols to determine whether the resulting recombinant polymerase displays a modified activity for a nucleotide analogue as compared to the first DNA polymerase. For example, $k_{cat}$, $K_m$, $V_{max}$, or $k_{cat}/K_m$ of the recombinant DNA polymerase for the nucleotide analogue can be determined. Further, $k_{cat}$, $K_m$, $V_{max}$, or $k_{cat}/K_m$ of the recombinant DNA polymerase for a natural nucleotide can also be determined (e.g., where the polymerase desirably includes both analogue and natural nucleotide incorporation activity).

A library of recombinant DNA polymerases can be made and screened for these properties. For example, a plurality of members of the library can be made to include one or more steric inhibition feature mutation and/or a mutation to produce complementary with one or more non-natural features of the nucleotide analogue, that is then screened for the properties of interest. In general, the library can be screened to identify at least one member comprising a modified activity of interest.

In an additional aspect, the invention includes computer-implemented methods, e.g., for modeling enzyme kinetics. The methods include, e.g., defining a plurality of polymerase state transitions for discrete time steps during a template-based polymerization reaction; defining a plurality of rate transition rates between the states; generating a multidimensional probability matrix of possible states, based upon a given nucleic acid template sequence, nucleotides in a reaction mixture and the polymerase state transitions; and, storing the multidimensional probability matrix in a computer readable medium.

A variety of features of the method can vary. For example, the polymerase state transitions are optionally user-selectable. The rate transition rates between the states optionally vary depending on nucleotide concentration, template sequence and position of the polymerase along the template. The nucleotides in the reaction mixture optionally comprise one or more nucleotide analogues. The rate transition rates between states optionally include a conformational transition rate for the polymerase during use of the nucleotide analogues by the polymerase, with the rate set to be equal to a conformational transition rate for a natural nucleotide. The multidimensional probability matrix is optionally automatically generated based upon the template sequence, a standardized matrix of probability states, and the nucleotides in the reaction mixture. The probability matrix is optionally simplified by assuming that all possible Watson-Crick base pairings are equivalent in all state transitions.

Similarly, a second reagent concentration matrix is optionally generated to account for reagent concentration changes that result from position of the polymerase along a template, based on an output of the probability matrix. The probability matrix is optionally vectorized for multiple templates and the resulting vectorized probability matrix can be multiplied by the multidimensional probability matrix to provide a state distribution matrix. An exponential time factor for the probability matrix can be used to account for repeated sequences within the template sequence. A polymerase nucleotide mismatch fraction using either a continuum model or a counting model can be defined.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A presents a sequence alignment for Phi 29-like polymerases in the region surrounding residues 505-525 (Phi29 SEQ ID NO:35, B103 SEQ ID NO:36, PZA SEQ ID NO:37, M2 SEQ ID NO:38, G1 SEQ ID NO:39, cp-1 SEQ ID NO:40).

FIGS. 3B-3G illustrate the structure of Phi 29 (FIGS. 3B-3D) and an E375H mutant (FIGS. 3E-3G). Views of the structures from three different angles are shown.

FIG. 4A presents a sequence alignment for Phi 29-like polymerases in the region surrounding E486 of Phi 29 (Phi29 SEQ ID NO:47, B103 SEQ ID NO:48, PZA SEQ ID NO:49, M2 SEQ ID NO:50, G1 SEQ ID NO:51, cp-1 SEQ ID NO:52).

FIG. 6A shows a sequence alignment for Phi 29-like polymerases in the region surrounding K135 of Phi 29 (Phi29 SEQ ID NO:59, B103 SEQ ID NO:60, PZA SEQ ID NO:61, M2 SEQ ID NO:62, G1 SEQ ID NO:63, cp-1 SEQ ID NO:64).

FIG. 10C schematically illustrates a kinetic model of a polymerase-template-dNTP system. FIG. 10D illustrates the relationship between the current state and the new state. FIG. 10E schematically illustrates expansion of the matrix.

DETAILED DISCUSSION OF THE INVENTION

Overview

Figure 1:
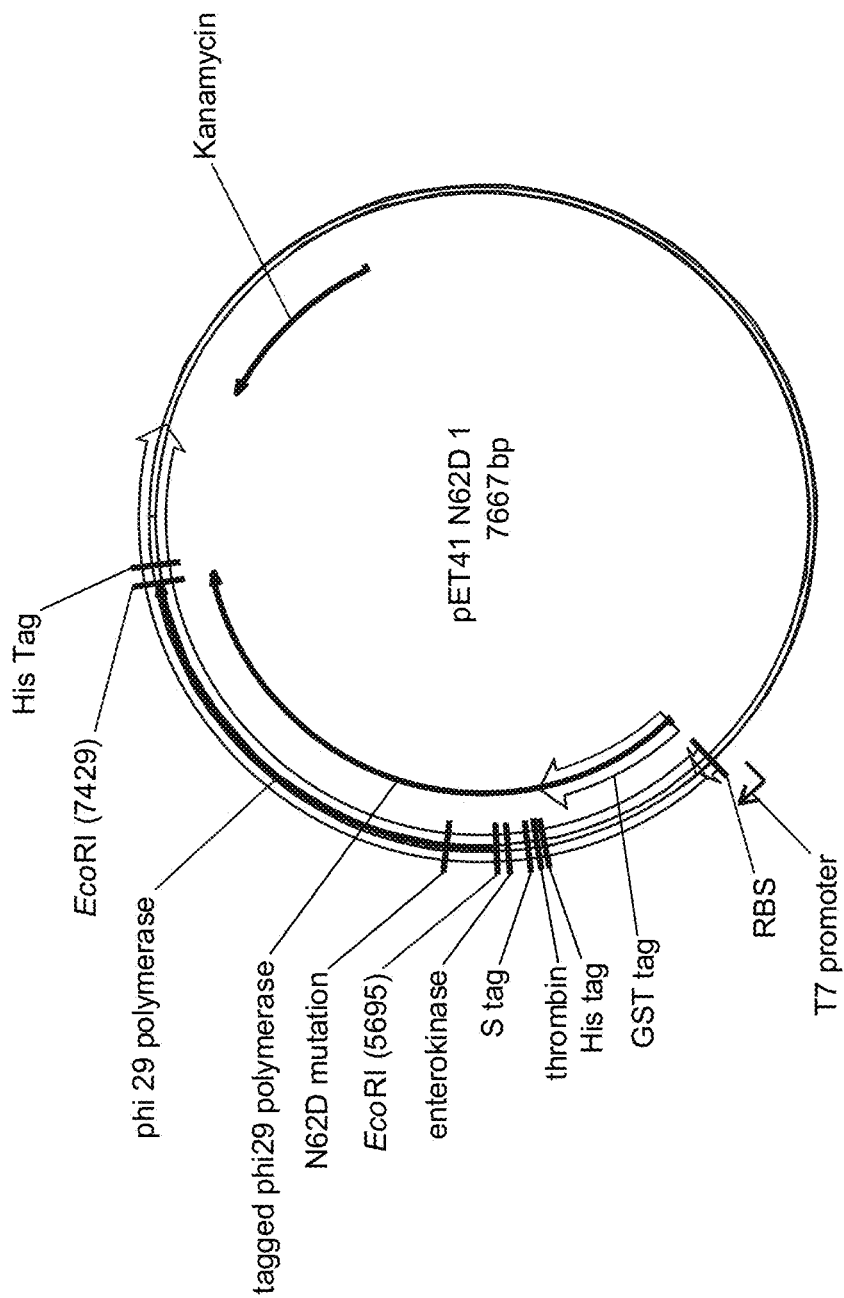
FIG. 1 schematically depicts a vector for expression of tagged N62D Phi 29 DNA polymerase.

A variety of technologies rely on the incorporation of labels into nucleic acids to observe the results of an experiment. For example, the outcome of sequencing, nucleic acid amplification and nick translation reactions are all typically monitored by labeling product nucleic acids. This is often done by covalently or non-covalently binding labels to the product nucleic acids, e.g., by binding labeled probes to the product nucleic acid. In other approaches, nucleotide analogues are incorporated into product nucleic acids during synthesis of the product nucleic acid. This typically occurs, e.g., in sequencing by incorporation methods, and certain real-time PCR (RT-PCR) and real-time LCR reactions (RT-LCR). A label present on the analogue can be incorporated into the DNA, or it can be released by action of the polymerase. Incorporation or release of the label can be monitored to monitor incorporation of an analogue residue into the product nucleic acid.

The present invention provides new polymerases that incorporate nucleotide analogues, such as dye labeled phosphate labeled analogues, into a growing template copy, during DNA amplification. These polymerases are modified such that the active site of the polymerase is modified to reduce steric entry inhibition of the analogue into the active site (facilitating entry of the nucleotide analogue into the active site) and/or to provide complementarity with one or more non-natural features of the nucleotide analogue.

These new polymerases are particularly well-suited to DNA amplification (e.g., RT-PCR and RT-LCR) and/or sequencing applications, e.g., in the context of amplification or sequencing protocols that include incorporation of labeled analogues into DNA amplicons.

DNA Polymerases

DNA polymerases that can be modified to interact with nucleotide analogues by reducing steric entry inhibition into the active site, or by adding features complementary to the analogues, are generally available. DNA polymerases have relatively recently been classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" *J Biol Chem.* 276(47):43487-90. For a review of polymerases, see, e.g., Hübscher et al. (2002) EUKARYOTIC DNA POLYMERASES *Annual Review of Biochemistry* Vol. 71: 133-163; Alba (2001) "Protein Family Review: Replicative DNA Polymerases" *Genome Biology* 2(1):reviews 3002.1-3002.4; and Steitz (1999) "DNA polymerases: structural diversity and common mechanisms" *J Biol Chem* 274: 17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29 is available.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. Any of these available polymerases can be modified in accordance with the invention to reduce steric inhibition to analogue entry into the active site, or to provide features complementary to the analogue. Many such polymerases that are suitable for modification are available, e.g., for use in sequencing, labeling and amplification technologies. For example, Human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicenter. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase is available from New England Biolabs; GoTaq® Flexi DNA Polymerase available from Promega; RepliPHI™ Φ29 DNA Polymerase from EPICENTRE; PfuUltra™ Hotstart DNA Polymerase available from Stratagene; KOD HiFi DNA Polymerase is available from Novagen and many others. Biocompare(dot) com provides comparisons of many different commercially available polymerases.

DNA polymerases that are preferred substrates for mutation to reduce steric inhibition or to incorporate features complementary to the nucleotide analogue include Taq polymerases, exonuclease deficient Taq polymerases, *E. coli* DNA Polymerase 1, Klenow fragment, reverse transcriptases, Φ29 related polymerases including wild type Φ29 polymerase derivatives of such polymerases such as exonuclease deficient forms, T7 DNA Polymerase, T5 DNA Polymerase, an RB69 polymerase, etc. For example, the recombinant DNA polymerase can be homologous to a wild-type or exonuclease deficient Φ29 DNA polymerase, e.g., as described in U.S. Pat. Nos. 5,001,050, 5,198,543, or 5,576,204. Similarly, the recombinant DNA polymerase can be homologous to Φ29, B103, GA-1, PZA, Φ15, BS32, M2Y, Nf, G1, Cp-1, PRD1, PZE, SF5, Cp-5, Cp-7, PR4, PR5, PR722, or L17, or the like.

Nucleotide Analogues

As discussed, various polymerases of the invention can incorporate one or more nucleotide analogues into a growing oligonucleotide chain. Upon incorporation, the analogue can leave a residue that is the same or different than a natural nucleotide in the growing oligonucleotide (the polymerase can incorporate any non-standard moiety of the analogue, or can cleave it off during incorporation into the oligonucleotide). A "nucleotide analogue" herein is a compound that, in a particular application, functions in a manner similar or analogous to a naturally occurring nucleoside triphosphate (a "nucleotide"), and does not otherwise denote any particular structure. A nucleotide analogue is an analogue other than a standard naturally occurring nucleotide, i.e., other than A, G, C, T, or U, though upon incorporation into the oligonucleotide, the resulting residue in the oligonucleotide can be the same as (or different from) an A, G, C, T or U residue.

Many nucleotide analogues are available. These include analogue structures with core similarity to naturally occurring nucleotides, such as those that comprise one or more substituent on a phosphate, sugar or base moiety of the nucleoside or nucleotide relative to a naturally occurring nucleoside or nucleotide. In one embodiment, a nucleotide analogue can include one or more extra phosphate containing groups, relative to a nucleoside triphosphate. For example, a variety of nucleotide analogues that comprise, e.g., from 4-6 phosphates are described in detail in U.S. patent application Ser. No. 11/241,809, filed Sep. 29, 2005, and incorporated herein by reference in its entirety for all purposes.

For example, the analogue can include a labeled compound of the formula:

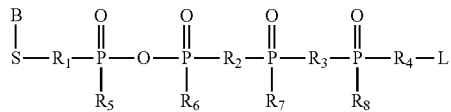

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, C(OH)CH$_2$R where R is 4-pyridine or 1-imidazole, provided that $R_4$ may additionally be selected from

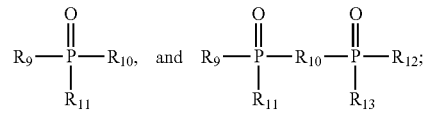

$R_5$, $R_6$, $R_7$, $R_8$, $R_{11}$ and $R_{13}$ are, when present, each independently selected from O, BH$_3$, and S; and $R_9$, $R_{10}$ and $R_{12}$ are independently selected from O, NH, S, methylene, substituted methylene, CNH$_2$, CH$_2$CH$_2$, C(OH)CH$_2$R where R is 4-pyridine or 1-imidazole. In some cases, phosphonate analogs may be employed as the analogs, e.g., where one of $R_2$, $R_3$, $R_4$, R9, R10 or R12 are not O, e.g., they are methyl etc. See, e.g., U.S. patent application Ser. No. 11/241,809, previously incorporated herein by reference in its entirety for all purposes.

The base moiety incorporated into the analogue is generally selected from any of the natural or non-natural nucleobases or nucleobase analogs, including, e.g., purine or pyrimidine bases that are routinely found in nucleic acids and available nucleic acid analogs, including adenine, thymine, guanine, cytidine, uracil, and in some cases, inosine. As noted, the base optionally includes a label moiety. For convenience, nucleotides and nucleotide analogs are generally referred to based upon their relative analogy to naturally occurring nucleotides. As such, an analogue that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogues, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2', 3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in published U.S. Patent Application No. 2003/0124576, previously incorporated herein by reference in its entirety for all purposes.

For most cases, the phosphorus containing chain in the analogues, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$) group. The labeling groups employed in the analogs of the invention may comprise any of a variety of detectable labels. Detectable labels generally denote a chemical moiety that provides a basis for detection of the analogue compound separate and apart from the same compound lacking such a labeling group. Examples of labels include, e.g., optical labels, e.g., labels that impart a detectable optical property to the analogue, electrochemical labels, e.g., labels that impart a detectable electrical or electrochemical property to the analogue, physical labels, e.g., labels that impart a different physical or spatial property to the analogue, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc., and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogues incorporated by the polymerases of the present invention are described in, e.g., Published U.S. Patent Application No. 2003/0124576, the full disclosure of which is incorporated herein in its entirety for all purposes.

Additional details regarding analogues and methods of making such analogues can be found in U.S. patent application Ser. No. 11/241,809, filed Sep. 29, 2005, and incorporated herein by reference in its entirety for all purposes.

Thus, in one illustrative example, the analogue can be a phosphate analogue (e.g., an analogue that has more than the typical number of phosphates found in nucleoside triphosphates) that include, e.g., an Alexa dye label. For example, an Alexa488 dye can be labeled on a deltaphosphate (denoted, e.g., A488dC4P), or an Alexa568 or Alexa633 dye can be used (e.g., A568dC4P, and A633dC4P respectively), or an Alexa546 dye can be used (e.g., A546dG4P), or an Alexa594 dye can be used (e.g., A594dT4P). Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

Modifying DNA Polymerases to Reduce Steric Hindrance Features and/or to Add Complementarity Features
Structure-Based Design of Recombinant Polymerases Structural data for a polymerase can be used to conveniently identify amino acid residues as candidates for mutagenesis to create recombinant polymerases having modified active site regions. For example, analysis of the three-dimensional structure of a polymerase can identify residues that sterically hinder access to the active site by a natural nucleotide or nucleotide analogue or analogue thereof or that can be mutated to introduce a feature complementary to a non-natural feature of the analogue, e.g., by adding or altering charge, hydrophobicity, size, or the like.

The three-dimensional structures of a large number of DNA polymerases have been determined by x-ray crystallography and nuclear magnetic resonance (NMR) spectroscopy, including the structures of polymerases with bound templates, nucleotides, and/or nucleotide analogues. Many such structures are freely available for download from the Protein Data Bank, at (www(dot)rcsb(dot)org/pdb. Structures, along with domain and homology information, are also freely available for search and download from the National Center for Biotechnology Information's Molecular Modeling DataBase, at www(dot)ncbi(dot)nlm(dot)nih(dot)gov/Structure/MMDB/mmdb(dot)shtml. The structures of additional polymerases can be modeled, for example, based on homology of the polymerases with polymerases whose structures have already been determined. Alternatively, the structure of a given polymerase, optionally complexed with a nucleotide analogue, or the like, can be determined.

Techniques for crystal structure determination are well known. See, for example, McPherson (1999) *Crystallization of Biological Macromolecules* Cold Spring Harbor Laboratory; Bergfors (1999) *Protein Crystallization* International University Line; Mullin (1993) *Crystallization* Butterwoth-Heinemann; Stout and Jensen (1989) *X-ray structure determination: a practical guide,* 2nd Edition Wiley Publishers, New York; Ladd and Palmer (1993) *Structure determination by X-ray crystallography,* 3rd Edition Plenum Press, New York; Blundell and Johnson (1976) *Protein Crystallography* Academic Press, New York; Glusker and Trueblood (1985) *Crystal structure analysis: A primer,* 2nd Ed. Oxford University Press, New York; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag; Fanchon and Hendrickson (1991) Chapter 15 of *Crystallographic Computing, Volume* 5 IUCr/Oxford University Press; Murthy (1996) Chapter 5 of *Crystallographic Methods and Protocols* Humana Press; Dauter et al. (2000) "Novel approach to phasing proteins: derivatization by short cryo-soaking with halides" Acta Cryst.D56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl Acad. Sci. USA, 88:4240-4244; and Gavira et al. (2002) "Ab initio crystallographic structure determination of insulin from protein to electron density without crystal handling" Acta Cryst.D58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276:307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and O (Jones et al. (1991) "Improved methods for building protein models in electron density maps and the location of errors in these models" Acta Crystallogr A 47 (Pt 2):110-119).

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis*, 2nd Edition, Wiley-VCH; Macomber (1998) *A Complete Introduction to Modem NMR Spectroscopy*, Wiley-Interscience; Downing (2004) Protein NMR Techniques (Methods in Molecular Biology), 2nd edition, Humana Press; Clore and Gronenborn (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) Curr. Opin. Struct. Biol. 10:585; Gardner (1998) Annu. Rev. Biophys. Biomol. Struct. 27:357; Wüthrich (2003) Angew. Chem. Int. Ed. 42:3340; Bax (1994) Curr. Opin. Struct. Biol. 4:738; Pervushin et al. (1997) Proc. Natl. Acad. Sci. U.S.A. 94:12366; Fiaux et al. (2002) Nature 418:207; Fernandez and Wider (2003) Curr. Opin. Struct. Biol. 13:570; Ellman et al. (1992) J. Am. Chem. Soc. 114:7959; Wider (2000) BioTechniques 29:1278-1294; Pellecchia et al. (2002) Nature Rev. Drug Discov. (2002) 1:211-219; Arora and Tamm (2001) Curr. Opin. Struct. Biol. 11:540-547; Flaux et al. (2002) Nature 418:207-211; Pellecchia et al. (2001) J. Am. Chem. Soc. 123:4633-4634; and Pervushin et al. (1997) Proc. Natl. Acad. Sci. USA 94:12366-12371.

The structure of a polymerase with a given nucleotide analogue incorporated into the active site can, as noted, be directly determined, e.g., by x-ray crystallography or NMR spectroscopy, or the structure can be modeled based on the structure of the polymerase and/or a structure of a polymerase with a natural nucleotide bound. The active site region of the polymerase can be identified, for example, by homology with other polymerases, examination of polymerase-template or polymerase-nucleotide co-complexes, biochemical analysis of mutant polymerases, and/or the like. The position of a nucleotide analogue in the active site can be modeled, for example, by projecting the location of non-natural features of the analogue (e.g., additional phosphate or phosphonate groups in the phosphorus containing chain linked to the nucleotide, e.g., tetra, penta or hexa phosphate groups, detectable labeling groups, e.g., fluorescent dyes, or the like) based on the previously determined location of another nucleotide or nucleotide analogue in the active site.

Such modeling of the nucleotide analogue in the active site can involve simple visual inspection of a model of the polymerase, for example, using molecular graphics software such as the PyMOL viewer (open source, freely available on the World Wide Web at www(dot)pymol(dot)org) or Insight II (commercially available from Accelrys at (www (dot) accelrys (dot) com/products/insight). Alternatively, modeling of the nucleotide analogue in the active site of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at (www (dot) usm (dot) maine (dot) edu/~rhodes/SPVTut/index (dot) html; and Methods for Protein Simulations and Drug Design at (www (dot) dddc (dot) ac (dot) cn/embo04; and references therein. Software to facilitate such modeling is widely available, for example, the CHARMm simulation package, available academically from Harvard University or commercially from Accelrys (at www (dot) accelrys (dot) com), the Discover simulation package (included in Insight II, supra), and Dynama (available at (www(dot) cs (dot) gsu (dot) edu/~cscrwh/progs/progs (dot) html). See also an extensive list of modeling software at (www (dot) netsci (dot) org/Resources/Software/Modeling/MMMD/top (dot) html.

Visual inspection and/or computational analysis of a polymerase model can identify relevant features of the active site region, including, for example, residues that can sterically inhibit entry of a nucleotide analogue into the active site (e.g., residues undesirably close to the projected location of one or more atoms within the analogue when the analogue is bound to the polymerase). Such a residue can, for example, be deleted or replaced with a residue having a smaller side chain; for example, many residues can be conveniently replaced with a residue having similar characteristics but a shorter amino acid side chain, or, e.g., with alanine. Similarly, residues that can be altered to introduce desirable interactions with the nucleotide analogue can be identified. Such a residue can be replaced with a residue that is complementary with a non-natural feature of the analogue, for example, with a residue that can hydrogen bond to the analogue (e.g., serine, threonine, histidine, asparagine, or glutamine), a hydrophobic residue that can interact with a hydrophobic group on the analogue, an aromatic residue that can provide favorable hydrophobic interactions with a group on the analogue (e.g., a fluorophore), an aromatic residue that can engage in a π-π or edge-face stacking interaction with an aromatic group in the analogue, a residue that can engage in a cation-π interaction with the analogue, or a charged residue (e.g., aspartic or glutamic acid, or lysine, arginine, or histidine) that can electrostatically interact with an oppositely charged moiety on the analogue (e.g., an additional phosphate group).

As just one specific example of such structure-based design, inspection of a model of the Φ29 polymerase identified the Δ505-525 domain and residues K135, E486, and K512 as potentially sterically inhibiting entry of an analogue into the active site, and suggested that mutation of E375 to histidine, lysine, or arginine would introduce a positive charge complementary to a non-natural tetra phosphate on the analogue. Similarly, inspection of the model suggested that mutation of E375 to an aromatic residue such as tryptophan, tyrosine, or phenylalanine would improve hydrophobic interactions with a fluorophore on the analogue. See Examples 2 and 3 below for additional details.

Thus, in addition to methods of using the polymerases and other compositions herein, the present invention also includes methods of making the polymerases. As described, methods of making a recombinant DNA polymerase can include structurally modeling a first polymerase, e.g., using any available crystal structure and molecular modeling software or system. Based on the modeling, one or more steric inhibition feature or complementarity feature affecting nucleotide access to the active site and/or binding of a nucleotide analogue within the active site region is identified, e.g., in the active site or proximal to it. The first DNA polymerase is mutated to reduce or remove at least one steric inhibition feature or to add the complementarity feature.

Mutating Active Site Regions

Various types of mutagenesis are optionally used in the present invention, e.g., to modify polymerases to produce variants comprising complementarity features and or to reduce steric hindrance features, e.g., in accordance with polymerase models and model predictions as discussed above. In general, any available mutagenesis procedure can be used for making such mutants. Such mutagenesis procedures optionally include selection of mutant nucleic acids and polypeptides for one or more activity of interest (e.g., improved $K_m$, $V_{max}$, $k_{cat}$ etc., for a nucleotide analogue). Procedures that can be used include, but are not limited to: site-directed point mutagenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill.

Optionally, mutagenesis can be guided by known information from a naturally occurring polymerase molecule, or of a known altered or mutated polymerase (e.g., using an existing mutant polymerase that displays reduced exonuclease activity), e.g., sequence, sequence comparisons, physical properties, crystal structure and/or the like as discussed above. However, in another class of embodiments, modification can be essentially random (e.g., as in classical DNA shuffling).

Additional information on mutation formats is found in: Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2006) ("Ausubel")) and *PCR Protocols A Guide to Methods and Applications* (Innis et al. eds) Academic Press Inc. San Diego, Calif. (1990) (Innis). The following publications and references cited within provide still additional detail on mutation formats: Arnold, *Protein engineering for unusual environments*, Current Opinion in Biotechnology 4:450-455 (1993); Bass et al., *Mutant Trp repressors with new DNA-binding specificities*, Science 242:240-245 (1988); Botstein & Shortle, *Strategies and applications of in vitro mutagenesis*, Science 229:1193-1201(1985); Carter et al., *Improved oligonucleotide site-directed mutagenesis using M13 vectors*, Nucl. Acids Res. 13: 4431-4443 (1985); Carter, *Site-directed mutagenesis*, Biochem. J. 237:1-7 (1986); Carter, *Improved oligonucleotide-directed mutagenesis using M13 vectors*, Methods in Enzymol. 154: 382-403 (1987); Dale et al., *Oligonucleotide-directed random mutagenesis using the phosphorothioate method*, Methods Mol. Biol. 57:369-374 (1996); Eghtedarzadeh & Henikoff, *Use of oligonucleotides to generate large deletions*, Nucl. Acids Res. 14: 5115 (1986); Fritz et al., *Oligonucleotide-directed construction of mutations: a gapped duplex DNA procedure without enzymatic reactions in vitro*, Nucl. Acids Res. 16: 6987-6999 (1988); Grundström et al., *Oligonucleotide-directed mutagenesis by microscale 'shot-gun' gene synthesis*, Nucl. Acids Res. 13: 3305-3316 (1985); Kunkel, *The efficiency of oligonucleotide directed mutagenesis, in Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection*, Proc. Natl. Acad. Sci. USA 82:488-492 (1985); Kunkel et al., *Rapid and efficient site-specific mutagenesis without phenotypic selection*, Methods in Enzymol. 154, 367-382 (1987); Kramer et al., *The gapped duplex DNA approach to oligonucleotide-directed mutation construction*, Nucl. Acids Res. 12: 9441-9456 (1984); Kramer & Fritz *Oligonucleotide-directed construction of mutations via gapped duplex DNA*, Methods in Enzymol. 154:350-367 (1987); Kramer et al., *Point Mismatch Repair*, Cell 38:879-887 (1984); Kramer et al., *Improved enzymatic in vitro reactions in the gapped duplex DNA approach to oligonucleotide-directed construction of mutations*, Nucl. Acids Res. 16: 7207 (1988); Ling et al., *Approaches to DNA mutagenesis: an overview*, Anal Biochem. 254(2): 157-178 (1997); Lorimer and Pastan Nucleic Acids Res. 23, 3067-8 (1995); Mandecki, *Oligonucleotide-directed double-strand break repair in plasmids of Escherichia coli: a method for site-specific mutagenesis*, Proc. Natl. Acad. Sci. USA, 83:7177-7181 (1986); Nakamaye & Eckstein, *Inhibition of restriction endonuclease Nci I cleavage by phosphorothioate groups and its application to oligonucleotide-directed mutagenesis*, Nucl. Acids Res. 14: 9679-9698 (1986); Nambiar et al., *Total synthesis and cloning of a gene coding for the ribonuclease S protein*, Science 223: 1299-1301 (1984); Sakamar and Khorana, *Total synthesis and expression of a gene for the a-subunit of bovine rod outer segment guanine nucleotide-binding protein (transducin)*, Nucl. Acids Res. 14: 6361-6372 (1988); Sayers et al., *Y-T Exonucleases in phosphorothioate-based oligonucleotide-directed mutagenesis*, Nucl. Acids Res. 16:791-802 (1988); Sayers et al., *Strand specific cleavage of phosphorothioate-containing DNA by reaction with restriction endonucleases in the presence of ethidium bromide*, (1988) Nucl. Acids Res. 16: 803-814; Sieber, et al., Nature Biotechnology, 19:456-460 (2001); Smith, *In vitro mutagenesis*, Ann. Rev. Genet. 19:423-462(1985); Methods in Enzymol. 100: 468-500 (1983); Methods in Enzymol. 154: 329-350 (1987); Stemmer, Nature 370, 389-91 (1994); Taylor et al., *The use of phosphorothioate-modified DNA in restriction enzyme reactions to prepare nicked DNA*, Nucl. Acids Res. 13: 8749-8764 (1985); Taylor et al., *The rapid generation of oligonucleotide-directed mutations at high frequency using phosphorothioate-modified DNA*, Nucl. Acids Res. 13: 8765-8787 (1985); Wells et al., *Importance of hydrogen-bond formation in stabilizing the transition state of subtilisin*, Phil. Trans. R. Soc. Lond. A 317: 415-423 (1986); Wells et al., *Cassette mutagenesis: an efficient method for generation of multiple mutations at defined sites*, Gene 34:315-323 (1985); Zoller & Smith, *Oligonucleotide-directed mutagen-* esis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100: 468-500 (1983); and Zoller & Smith, Oligonucleotide-directed mutagenesis: a simple method using two oligonucleotide primers and a single-stranded DNA template, Methods in Enzymol. 154:329-350 (1987). Additional details on many of the above methods can be found in Methods in Enzymology Volume 154, which also describes useful controls for trouble-shooting problems with various mutagenesis methods.

Determining Kinetic Parameters

The polymerases of the invention can be screened or otherwise tested to determine whether the polymerase displays a modified activity for or with a nucleotide analogue as compared to the first DNA polymerase (e.g., a corresponding wild-type polymerase from which the recombinant polymerase was derived). For example, $k_{cat}$, $K_m$, $V_{max}$, $k_{cat}/K_m$, $V_{max}/K_m$, $k_{pol}$, and/or $K_d$ of the recombinant DNA polymerase for the nucleotide analogue can be determined. Further, $k_{cat}$, $K_m$, $V_{max}$, $V_{max}/K_m$, $k_{cat}/K_m$, $k_{pol}$, and/or $K_d$ of the recombinant DNA polymerase for a natural nucleotide can also be determined (e.g., where the polymerase desirably includes both analogue and natural nucleotide incorporation activity).

As is well-known in the art, for enzymes obeying simple Michaelis-Menten kinetics, kinetic parameters are readily derived from rates of catalysis measured at different substrate concentrations. The Michaelis-Menten equation, $V=V_{max}[S]([S]+K_m)^{-1}$, relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V).

For many enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher $K_m$ represents a complex with weaker binding. The ratio $k_{cat}/K_m$, sometimes called the specificity constant, represents the apparent rate constant for combination of substrate with free enzyme. The larger the specificity constant, the more efficient the enzyme is in binding the substrate and converting it to product.

The $k_{cat}$ (also called the turnover number of the enzyme) can be determined if the total enzyme concentration ($[E_T]$, i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics.

In one embodiment, using presteady-state kinetics, the nucleotide concentration dependence of the rate $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the burst equation; Product=$A[1-\exp(-k_{obs}*t)]+k_{ss}*t$ where A represents amplitude an estimate of the concentration of the enzyme active sites, $k_{ss}$ is the observed steady-state rate constant and t is the reaction incubation time. The $K_m$ for dNTP binding to the polymerase-DNA complex and the $k_{pol}$ are calculated by fitting the dNTP concentration dependent change in the $k_{obs}$ using the equation $k_{obs}=(k_{pol}*[S])*(K_m+[S])-1$ where [S] is the substrate concentration. Results are optionally obtained from a rapid-quench experiment (also called a quench-flow measurement), for example, based on the methods described in Johnson (1986) "Rapid kinetic analysis of mechanochemical adenosinetriphosphatases" Methods Enzymol. 134:677-705, Patel et al. (1991) "Pre-steady-state kinetic analysis of processive DNA replication including complete characterization of an exonuclease-deficient mutant" Biochemistry 30(2):511-25, and Tsai and Johnson (2006) "A new paradigm for DNA polymerase specificity" Biochemistry 45(32):9675-87.

Parameters such as rate of binding of a nucleotide analogue by the recombinant polymerase, rate of product release by the recombinant polymerase, or branching rate of the recombinant polymerase (the "branching rate" is the rate of dissociation of a nucleotide or nucleotide analogue from the polymerase active site without incorporation of the nucleotide or nucleotide analogue, where the nucleotide or nucleotide analogue if it were incorporated would correctly base-pair with a complementary nucleotide or nucleotide analogue in the template) can also be determined, and optionally compared to that of the first polymerase (e.g., a corresponding wild-type polymerase). See, e.g., Example 3 herein.

For a more thorough discussion of enzyme kinetics, see, e.g., Berg, Tymoczko, and Stryer (2002) Biochemistry, Fifth Edition, W. H. Freeman; Creighton (1984) Proteins: Structures and Molecular Principles, W. H. Freeman; and Fersht (1985) Enzyme Structure and Mechanism, Second Edition, W. H. Freeman.

As discussed above, the relevant DNA polymerase has a modified active site region that is homologous to a wild-type active site region of a wild-type DNA polymerase e.g., that includes one or more structural modification relative to the wild type active site region that increases the relative activity of the enzyme to one or more of natural nucleotides and/or nucleotide analogues, with increases in activity to nucleotide analogues being a preferred goal. In at least one aspect, without being bound to any particular theory of operation, the modifications are targeted to reduce steric inhibition for entry of the nucleotide analogue into the modified active site and/or that is complementary with one or more non-natural features of the nucleotide analogue. A $K_m$ value of the recombinant polymerase for the nucleotide analogue is typically lower than a $K_m$ for a corresponding homologous wild-type polymerase for the nucleotide analogue.

In one aspect, the improved activity of the enzymes of the invention is measured with reference to a model analogue or analogue set and compared with a given parental enzyme.

For example, in the case of enzymes derived from a Φ29 parental enzyme, an improved enzyme of the invention would have a lower Km than the parental enzyme, e.g., wild type Φ29 or N62D Φ29, toward a given analogue. In general, for purposes of discussion, examples of improved enzymes of the invention will be characterizable as having lower $K_m$s toward A488dC4P and/or A568dC4P, two analogs that have been reasonably well processed and reasonably poorly processed by Φ29 derived enzymes, respectively, that are, e.g., from about 5% or less to about 90% or less of the $K_m$ possessed by N62D Φ29 toward the same analogs. For example, as set forth in more detail in the examples below, e.g., at Table 2, His-375H-N62D Φ29 displays a $K_m$ that is about 40% of $K_m$ of N62D Φ29 for A488dC4P, while His-375S-N62D Φ29 displays a $K_m$ that is about 75% of the $K_m$ of N62D Φ29 for A488dC4P. Similarly, His-375H-N62D Φ29 displays a $K_m$ that is about 15% of the $K_m$ of N62D Φ29 for A568dC4P, while His-375S-N62D Φ29 displays a $K_m$ that is about 38% of the $K_m$ of N62D Φ29 for A568dC4P. While the foregoing may be used as a characterization tool, it in no way is intended as a specifically limiting reaction of the invention.

Screening Polymerases

Screening or other protocols can be used to determine whether a polymerase displays a modified activity for a nucleotide analogue as compared to the first DNA polymerase. For example, $k_{cat}$, $K_m$, $V_{max}$, or $k_{cat}/K_m$ of the recombinant DNA polymerase for the nucleotide analogue can be determined as discussed above. Further, $k_{cat}$, $K_m$, $V_{max}$, or $k_{cat}/K_m$ of the recombinant DNA polymerase for a natural nucleotide can also be similarly determined (e.g., where the polymerase desirably includes both analogue and natural nucleotide incorporation activity).

In one desirable aspect, a library of recombinant DNA polymerases can be made and screened for these properties. For example, a plurality of members of the library can be made to include one or more putative steric inhibition feature mutation an/or a mutation to putatively produce complementary with one or more non-natural features of the nucleotide analogue, that is then screened for the properties of interest. In general, the library can be screened to identify at least one member comprising a modified activity of interest.

Libraries of polymerases can be either physical or logical in nature. Moreover, any of a wide variety of library formats can be used. For example, polymerases can be fixed to solid surfaces in arrays of proteins. Similarly, liquid phase arrays of polymerases (e.g., in microwell plates) can be constructed for convenient high-throughput fluid manipulations of solutions comprising polymerases. Liquid, emulsion, or gel-phase libraries of cells that express recombinant polymerases can also be constructed, e.g., in microwell plates, or on agar plates. Phage display libraries of polymerases or polymerase domains (e.g., including the active site region) can be produced. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. Furthermore, the patent and technical literature includes many examples of microfluidic systems which can interface directly with microwell plates for fluid handling.

Desirable Properties

The polymerases of the invention can include any of a variety of modified properties towards natural or nucleotide analogues or analogues, depending on the application, including increased speed, increased retention time (or decreased speed) for incorporated bases, greater processivity, etc. For example, where a higher level of nucleotide analogue incorporation is desired, the polymerase of the invention is selected to have a lower $K_m$, a higher Vmax and/or a higher $k_{cat}$ than a corresponding homologous wild-type polymerase with respect to a given nucleotide analogue. In certain embodiments, it is desirable to slow or quicken the overall nucleotide incorporation speed of the polymerase (e.g., depending on the resolution of the equipment used to monitor incorporation), or to improve processivity, specificity, or the like. In certain embodiments, the recombinant polymerase has an increased rate of binding of a nucleotide analogue, an increased rate of product release, and/or a decreased branching rate, as compared to a corresponding homologous wild-type polymerase. Any of these features can be screened for or against in selecting a polymerase of the invention.

For example, the polymerases of the invention can typically incorporate natural nucleotides (e.g., A, C, G and T) into a growing copy nucleic acid. For example, the recombinant polymerase optionally displays a specific activity for a natural nucleotide that is at least about 5% as high (e.g., 5%, 10%, 25%, 50%, 75%, 100% or higher) as a corresponding homologous wild-type polymerase and a processivity with natural nucleotides in the presence of a template that is at least 5% as high (e.g., 5%, 10%, 25%, 50%, 75%, 100% or higher) as the wild-type polymerase in the presence of the natural nucleotide. Optionally, the recombinant polymerase also displays a $k_{cat}/K_m$ or $V_{max}/K_m$ for a naturally occurring nucleotide that is at least about 10% as high (e.g., 10%, 25%, 50%, 75% or 100% or higher) as the wild-type polymerase.

Additional Example Details

A number of specific examples of modified active site regions are described herein. An "active site region" is a portion of the polymerase that includes or is proximal to the active site (e.g., within about 2 nm of the active site) in a three dimensional structure of a folded polymerase. Specific examples of structural modifications within or proximal to the active site of Φ29 DNA polymerase are described herein. For example, relative to a wild-type Φ29 DNA polymerase, these modification can include any of: a deletion of Δ505-525, a deletion within the Δ505-525 domain, a K135A mutation, an L384R mutation (e.g., in combination with another mutation herein), an E375H mutation, an E375S mutation, an E375K mutation, an E375R mutation, an E375A mutation, an E375Q mutation, an E375W mutation, an E375Y mutation, an E375F mutation, an E486A mutation, an E486D mutation, a K512A mutation, a mutation listed in Table 8, and combinations thereof. For example, the polymerase can include a combination of mutations selected from the list of combinations in Table 8.

The polymerase optionally further includes one or more mutations/deletions relative to the wild-type polymerase that reduce or eliminate endogenous exonuclease activity. For example, relative to the wild-type Φ29 DNA polymerase, N62 is optionally mutated or deleted to reduce exonuclease activity; e.g., the polymerase can include an N62D mutation. Other example mutations that reduce exonuclease activity include D12A, T15I, E14I, and/or D66A; accordingly, the polymerases of the invention optionally comprise one or more of these mutations.

As will be appreciated, the numbering of amino acid residues is with respect to the wild-type sequence of the Φ29 polymerase, and actual position within a molecule of the invention may vary based upon the nature of the various modifications that the enzyme includes relative to the wild type Φ29 enzyme, e.g., deletions and/or additions to the molecule, either at the termini or within the molecule itself.

Affinity Tags and Other Optional Polymerase Features

The recombinant DNA polymerase optionally includes additional features exogenous or heterologous to the polymerase. For example, the recombinant polymerase optionally includes one or more exogenous affinity tags, e.g., purification or substrate binding tags, such as a 6 His tag sequence, a GST tag, an HA tag sequence, a plurality of 6 His tag sequences, a plurality of GST tags, a plurality of HA tag sequences, a SNAP-tag, or the like. These and other features useful in the context of binding a polymerase to a surface are optionally included, e.g., to orient and/or protect the polymerase active site when the polymerase is bound to a surface. Other useful features include recombinant dimer domains of the enzyme, and, e.g., large extraneous polypeptide domains coupled to the polymerase distal to the active site. For example, for Φ29, the active site is in the C terminal region of the protein, and added surface binding elements (extra domains, His tags, etc.) are typically located in the N-terminal region to avoid interfering with the active site when the polymerase is coupled to a surface.

In general, surface binding elements and purification tags that can be added to the polymerase (recombinantly or, e.g., chemically) include, e.g., polyhistidine tags, HIS-6 tags, biotin, avidin, GST sequences, BiTag sequences, S tags, SNAP-tags, enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Additional details on fixing a polymerase to a surface are found in U.S. patent application 60/753,446 "PROTEIN ENGINEERING STRATEGIES TO OPTIMIZE ACTIVITY OF SURFACE ATTACHED PROTEINS" by Hanzel et al. and U.S. patent application 60/753,515 "ACTIVE SURFACE COUPLED POLYMERASES" by Hanzel et al., both filed Dec. 22, 2005 and incorporated herein by reference for all purposes, and in U.S. patent application Ser. No. 11/645,135 "PROTEIN ENGINEERING STRATEGIES TO OPTIMIZE ACTIVITY OF SURFACE ATTACHED PROTEINS" by Hanzel et al. and U.S. patent application Ser. No. 11/645,125 "ACTIVE SUR- FACE COUPLED POLYMERASES" by Hanzel et al. both co-filed herewith and incorporated herein by reference for all purposes.

Applications for Enhanced Incorporation of Nucleotide Analogues by a DNA Polymerase Polymerases of the invention, natural and/or nucleotide analogues and nucleic acid templates (DNA or RNA) are optionally used to copy the template nucleic acid. That is, a mixture of the polymerase, nucleotide analogues, and optionally natural nucleotides and other reagents, the template and a replication initiating moiety is reacted such that the polymerase extends the primer in a template-dependent manner. The moiety can be a standard oligonucleotide primer, or, alternatively, a component of the template, e.g., the template can be a self-priming single stranded DNA, a nicked double stranded DNA, or the like. Similarly, a terminal protein can serve as a initiating moiety. At least one nucleotide analogue can be incorporated into the DNA. The template DNA can be a linear or circular DNA, and in certain applications, is desirably a circular template (e.g., for rolling circle replication or for sequencing of circular templates). Optionally, the composition can be present in an automated DNA replication and/or sequencing system.

Incorporation of labeled nucleotide analogues by the polymerases of the invention are particularly useful in a variety of different nucleic acid analyses, including real-time monitoring of DNA polymerization. The label can itself be incorporated, or more preferably, can be released during incorporation. For example, analogue incorporation can be monitored in real-time by monitoring label release during incorporation of the analogue by the polymerase. The portion of the analogue that is incorporated can be the same as a natural nucleotide, or can include features of the analogue that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analogue, e.g., in a solid phase assay, or can arise upon the incorporation reaction. For example, in the case of FRET labels where a bound label is quenched and a free label is not, release of a label group from the incorporated analogue can give rise to a fluorescent signal. Alternatively, the enzyme may be labeled with one member of a FRET pair proximal to the active site, and incorporation of an analogue bearing the other member will allow energy transfer upon incorporation. The use of enzyme bound FRET components in nucleic acid sequencing applications is described, e.g., in Published U.S. Patent application No. 2003-0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analogue that is readily distinguishable from non-incorporated nucleotide analogs. In a preferred aspect, such small observation volumes are provided by immobilizing the polymerase enzyme within an optical confinement, such as a Zero Mode Waveguide. For a description of ZMWs and their application in single molecule analyses, and particularly nucleic acid sequencing, see, e.g., Published U.S. Patent Application No. 2003/0044781, and U.S. Pat. No. 6,917,726, each of which is incorporated herein by reference in its entirety for all purposes.

In general, a polymerase enzyme is complexed with the template strand in the presence of one or more nucleotides and/or one or more nucleotide analogue of the invention. For example, in certain embodiments, labeled analogues are present representing analogous compounds to each of the four natural nucleotides, A, T, G and C, e.g., in separate polymerase reactions, as in classical Sanger sequencing, or multiplexed together in a single reaction, as in multiplexed sequencing approaches. When a particular base in the template strand is encountered by the polymerase during the polymerization reaction, it complexes with an available analogue that is complementary to such nucleotide, and incorporates that analogue into the nascent and growing nucleic acid strand. In one aspect, incorporation can result in a label being released, e.g., in polyphosphate analogues, cleaving between the at and 3 phosphorus atoms in the analogue, and consequently releasing the labeling group (or a portion thereof). The incorporation event is detected, either by virtue of a longer presence of the analogue and, thus, the label, in the complex, or by virtue of release of the label group into the surrounding medium. Where different labeling groups are used for each of the types of analogs, e.g., A, T, G or C, identification of a label of an incorporated analogue allows identification of that analogue and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a Zero Mode Waveguide. In addition to their use in sequencing, the analogs of the invention are also equally useful in a variety of other genotyping analyses, e.g., SNP genotyping using single base extension methods, real time monitoring of amplification, e.g., RT-PCR methods, and the like.

Further details regarding sequencing and nucleic acid amplification can be found in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2006) ("Ausubel")) and *PCR Protocols A Guide to Methods and Applications* (Innis et al. eds) Academic Press Inc. San Diego, Calif. (1990) ("Innis").

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention, e.g., a mutant polymerase that, without being bound to a particular theory, reduces steric hindrance for a nucleotide analogue of the invention and/or that includes a complementarity feature. Recombinant methods for making nucleic acids, expression and isolation of expressed products are described, e.g., in Sambrook, Ausubel and Innis.

In addition, a plethora of kits are commercially available for the purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, *Gene* 8:81 (1979); Roberts, et al., *Nature*, 328:731 (1987); Schneider, B., et al., *Protein Expr. Purif* 6435:10 (1995); Ausubel, Sambrook, Berger (above). A catalogue of Bacteria and Bacteriophages useful for cloning is provided, e.g., by the ATCC, e.g., *The ATCC Catalogue of Bacteria and Bacteriophage* published yearly by the ATCC. Additional basic procedures for sequencing, cloning and other aspects of molecular biology and underlying theoretical considerations are also found in Watson et al. (1992) *Recombinant DNA Second Edition, Scientific American Books, NY.*

In addition, systems of orthogonal components are available that can incorporate any of a variety of unnatural amino acids into a recombinant protein (e.g., polymerase of the invention). In brief, a cell or other translation system (e.g., an in vitro translation system) is constructed that includes an orthogonal tRNA ("OtRNA"; a tRNA not recognized by the cell's endogenous translation machinery, such as an amber or 4-base tRNA) and an orthogonal tRNA synthetase ("ORS"; this is a synthetase that does not aminoacylate any endogenous tRNA of the cell, but which can aminoacylate the OtRNA in response to a selector codon). A nucleic acid encoding the enzyme is constructed to include a selector codon at a selected site that is specifically recognized by the OtRNA. The ORS specifically incorporates an unnatural amino acid with a desired chemical functionality at one or more selected site(s) (e.g., distal to the active site). This chemical functional group can be unique as compared to those ordinarily found on amino acids, e.g., that incorporate keto or other functionalities. Further information on orthogonal systems can be found, e.g., in Wang et al., (2001), *Science* 292:498-500; Chin et al., (2002) *Journal of the American Chemical Society* 124:9026-9027; Chin and Schultz, (2002), *ChemBioChem* 11:1135-1137; Chin, et al., (2002), *PNAS United States of America* 99:11020-11024; and Wang and Schultz, (2002), *Chem. Comm.*, 1-10. See also, International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; and WO 2005/007624, filed Jul. 7, 2004.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York)

and Atlas and Parks (eds) *The Handbook of Microbiological Media* (1993) CRC Press, Boca Raton, Fla.

In addition, essentially any nucleic acid can be custom or standard ordered from any of a variety of commercial sources, such as Operon Technologies Inc. (Alameda, Calif.).

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

Kits

The present invention also provides kits that incorporate the polymerases of the invention, e.g., with one or more nucleotide analogues, e.g., for sequencing, nucleic acid amplification, or the like. Such kits can include the polymerase of the invention packaged in a fashion to enable use of the polymerase, a set of different nucleotide analogs of the invention, e.g., those that are analogous to A, T, G, and C, e.g., where at least one of the analogues bears a detectable moiety, and in preferred aspects more than one, and in many cases, each bears a detectably different labeling group, optionally to permit identification in the presence of the other analogues. Depending upon the desired application, the kits of the invention optionally include additional reagents, such as natural nucleotides, a control template, and other reagents, such as buffer solutions and/or salt solutions, including, e.g., divalent metal ions, i.e., $Mg^{++}$, $Mn^{++}$ and/or $Fe^{++}$, standard solutions, e.g., dye standards for detector calibration. Such kits also typically include instructions for use of the compounds and other reagents in accordance with the desired application methods, e.g., nucleic acid sequencing, amplification and the like.

Nucleic Acid and Polypeptide Sequence and Variants

As described herein, the invention provides polynucleotide sequences encoding, e.g., a polymerase as described herein. Examples of polymerase sequences that include steric hindrance or complementarity features are found herein, e.g., in Table 3. However, one of skill in the art will immediately appreciate that the invention is not limited to those sequences. For example, one of skill will appreciate that the invention also provides, e.g., many related sequences with the functions described herein, e.g., polynucleotides and polypeptides encoding conservative variants of a polymerase of Table 3.

Accordingly, the invention provides a variety of polypeptides (polymerases) and polynucleotides (nucleic acids that encode polymerases). Example polynucleotides of the invention include, e.g., a polynucleotide comprising a nucleotide sequence as set forth in Table 3 or a polynucleotide that is complementary to or that encodes a polynucleotide sequence thereof (e.g., where the given sequence is a DNA, an RNA is one example of a sequence that encodes the DNA, e.g., via reverse transcription). A polynucleotide of the invention also optionally includes any polynucleotide that encodes a polymerase of Table 3. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes an altered steric hindrance or nucleotide analogue complementarity feature.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant reduced steric hindrance or nucleotide analogue complementarity feature (for example, the conservative substitution can be of a residue distal to the active site region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

In one aspect, the conservative substitution includes one or more deletion or substitution of a residue at an amino acid residue of the polymerase corresponding to amino acid residue 375.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE A

Conservative Amino Acid Substitutions

| Nonpolar and/ or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention. In addition, target nucleic acids which hybridize to a nucleic acid represented in Table 3 under high, ultra-high and ultra-ultra high stringency conditions, where the nucleic acids are other than a naturally occurring Φ29, or an N62D mutant, are a feature of the invention. Examples of such nucleic acids include those with one or a few silent or conservative nucleic acid substitutions as compared to a given nucleic acid sequence of Table 3.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 1×, 20×, 50×, 100×, or 500× or more as high as that observed for hybridization to any of the unmatched target nucleic acids. A target nucleic acid which hybridizes to a probe under such conditions, with a signal to noise ratio of at least 2 that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid that encodes a polymerase of Table 3. The unique subsequence may be unique as compared to a nucleic acid corresponding to wild type Φ29, or to an N62D mutation thereof. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polymerase of Table 3. Here, the unique subsequence is unique as compared to, e.g., wild type Φ29, or to an N62D mutation thereof.

The invention also provides for target nucleic acids which hybridize under stringent conditions to a unique coding oligonucleotide which encodes a unique subsequence in a polypeptide selected from the sequences of Table 3, wherein the unique subsequence is unique as compared to a polypeptide corresponding to wild type Φ29, or to an N62D mutation (e.g., parental sequences from which polymerases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Computer-Implemented Methods of Modeling Kinetics

In an additional aspect, the invention includes computer-implemented methods, e.g., for modeling enzyme kinetics. In the methods, a plurality of polymerase state transitions are defined for discrete time steps during a template-based polymerization reaction. In the smallest discrete time step, many polymerase state transitions are forbidden according to the enzymatic kinetics being modeled. A plurality of rate transition rates are defined between the states and a multidimensional probability matrix of possible state transitions is defined for the smallest discrete time step, based upon a given nucleic acid template sequence, nucleotides in a reaction mixture and the polymerase state transitions. The resulting multidimensional probability matrix is stored in a computer readable medium.

A variety of features of the method can vary. For example, the polymerase state transitions are optionally user-selectable. The transition rates between the states optionally vary depending on nucleotide concentration, polymerase concentration, template concentration, template sequence, position of the polymerase along the template, characteristics of the current Watson-Crick template-nucleotide pair, characteristics of the previous Watson-Crick template-nucleotide pair, or characteristics of the nucleotide being incorporated. The nucleotides in the reaction mixture optionally comprise one or more analogue nucleotides. The transition rates between states optionally include complete orthogonality between every combination of multidimensional dependencies listed above. The multidimensional probability matrix is optionally automatically generated based upon the template sequence, a standardized matrix of probability states, and the nucleotides in the reaction mixture. The probability matrix is optionally simplified by assuming that all possible Watson-Crick base pairings are equivalent in all state transitions. The probability matrix is further optionally simplified by assuming that certain state transitions (eg. polymerase translocation along DNA) are equivalent between different dimensions of the probability matrix (eg. certain characteristics of nucleotide previously incorporated).

Similarly, a second reagent concentration matrix is optionally generated to account for reagent concentration changes that result from position of the polymerase along a template, based on an output of the probability matrix. The probability matrix is optionally vectorized for multiple templates and the resulting vectorized probability matrix can be multiplied by the multidimensional probability matrix to provide a state distribution matrix. An exponential time factor for the probability matrix can be used to account for repeated sequences within the template sequence. A polymerase nucleotide mismatch fraction using either a continuum model or a counting model can be defined.

EXAMPLES

It is understood that the examples and embodiments described herein are for illustrative purposes only and that various modifications or changes in light thereof will be suggested to persons skilled in the art. Accordingly, the following examples are offered to illustrate, but not to limit, the claimed invention.

The following sets forth a series of experiments that demonstrate construction and characterization of a variety of recombinant DNA polymerases having modified active site regions and modified properties for nucleotide analogues.

Example 1: Expression of Recombinant Polymerase

A vector for expression of Phi 29 polymerase was constructed and is schematically illustrated in FIG. 1. An N62D mutation was introduced into wild-type Phi 29 (SEQ ID NO:1) to reduce exonuclease activity, and GST (glutathione-S-transferase), His, and S tags were added. The resulting tagged N62D Phi 29 amino acid sequence is presented as SEQ ID NO:2. The sequence of the vector is presented as SEQ ID NO: 14. The tagged N62D Phi 29 polymerase is encoded by nucleotides 4839-7428 of the vector sequence, with the polymerase at nucleotides 5700-7428 and the N62D mutation at nucleotides 5883-5885. Other features of the vector include the GST-His-S tag sequences (nucleotides 4838-5699), ribosome binding site (nucleotides 4822-4829), T7 promoter (nucleotides 4746-4758), and kanamycin resistance marker (complement of nucleotides 563-1375).

Additional mutations are readily introduced into this construct as desired, for example, to facilitate expression of recombinant Phi 29 polymerases having modified active site regions. See, e.g., SEQ ID NOs:15-23. The recombinant proteins can be expressed in *E. coli*, for example, and purified using the GST, His, and/or S tags and standard techniques. The tags are optionally removed by digestion with an appropriate protease (e.g., thrombin or enterokinase).

Example 2: Exemplary Recombinant Polymerases

A variety of recombinant Phi 29 polymerases with modified active site regions have been constructed. Without intending to be limited to any particular mechanism, the following examples illustrate structural modifications that can reduce steric inhibition for entry of nucleotide analogues into the modified active site regions, coordinate extra phosphate groups by providing features that complement these groups (e.g., positively charged amino acid side chains), and/or otherwise enhance the ability of the polymerase to incorporate nucleotide analogues.

FIG. 2 A shows a sequence alignment of Phi 29-like polymerases in the region surrounding residues 505-525, whose position is indicated by the bracket. Amino acid residues differing from Phi 29 are underlined. The majority of this domain is missing in the cp-1 DNA polymerase (which, like G1, is more distantly related to Phi 29). In addition, there is notably less sequence conservation within the domain than in the flanking sequence. These observations suggest that removal of the domain is unlikely to be deleterious.

Figure 2D:
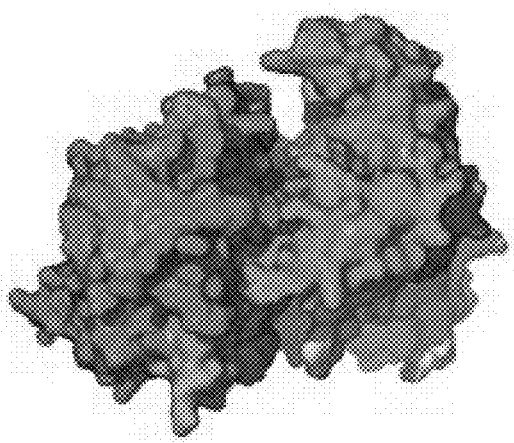
FIGS. 2B-2G illustrate the structure of Phi 29 with (FIGS. 2B-2D) and without (FIGS. 2E-2G) residues 505-525. Views of the structures from three different angles are shown.
Figure 2G:
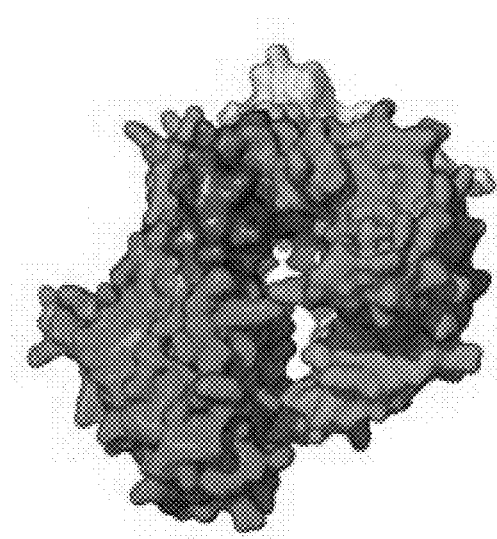
Figure 2C:
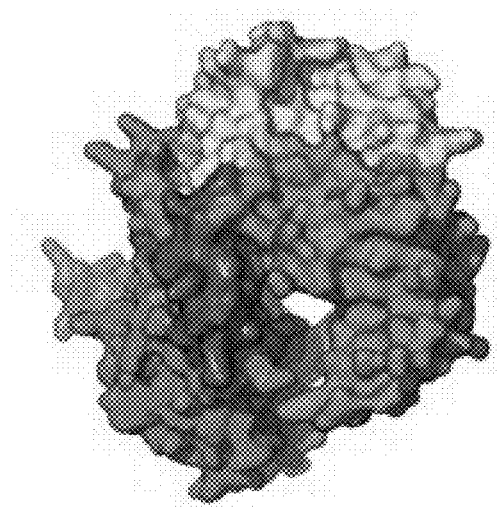
Figure 2F:
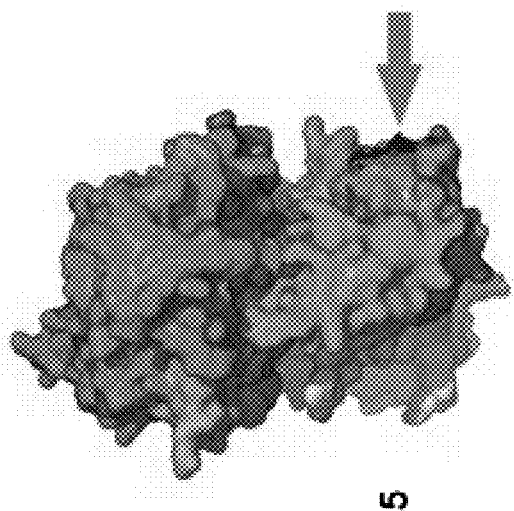
Figure 2B:
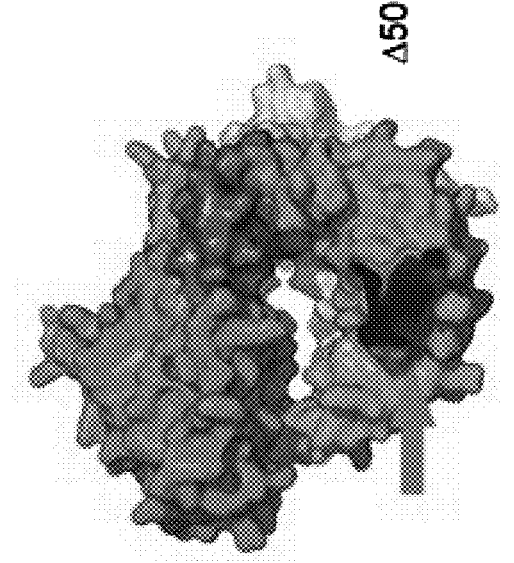
Figure 2E:
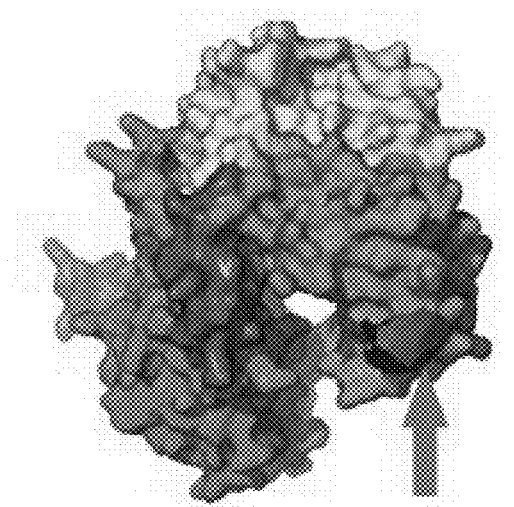

FIGS. 2B-2D illustrate the structure of the Phi 29 polymerase (see, e.g., Kamtekar et al. (2004) "Insights into strand displacement and processivity from the crystal structure of the protein-primed DNA polymerase of bacteriophage Φ29" Mol. Cell 16(4): 609-618). FIGS. 2E-2G show the polymerase with residues 505-525 removed, illustrating that removal of this domain opens up the nucleotide binding pocket. See, e.g., SEQ ID NOs: 12 and 13 or 33 and 34, which remove this domain using different turns.

Figure 3A:
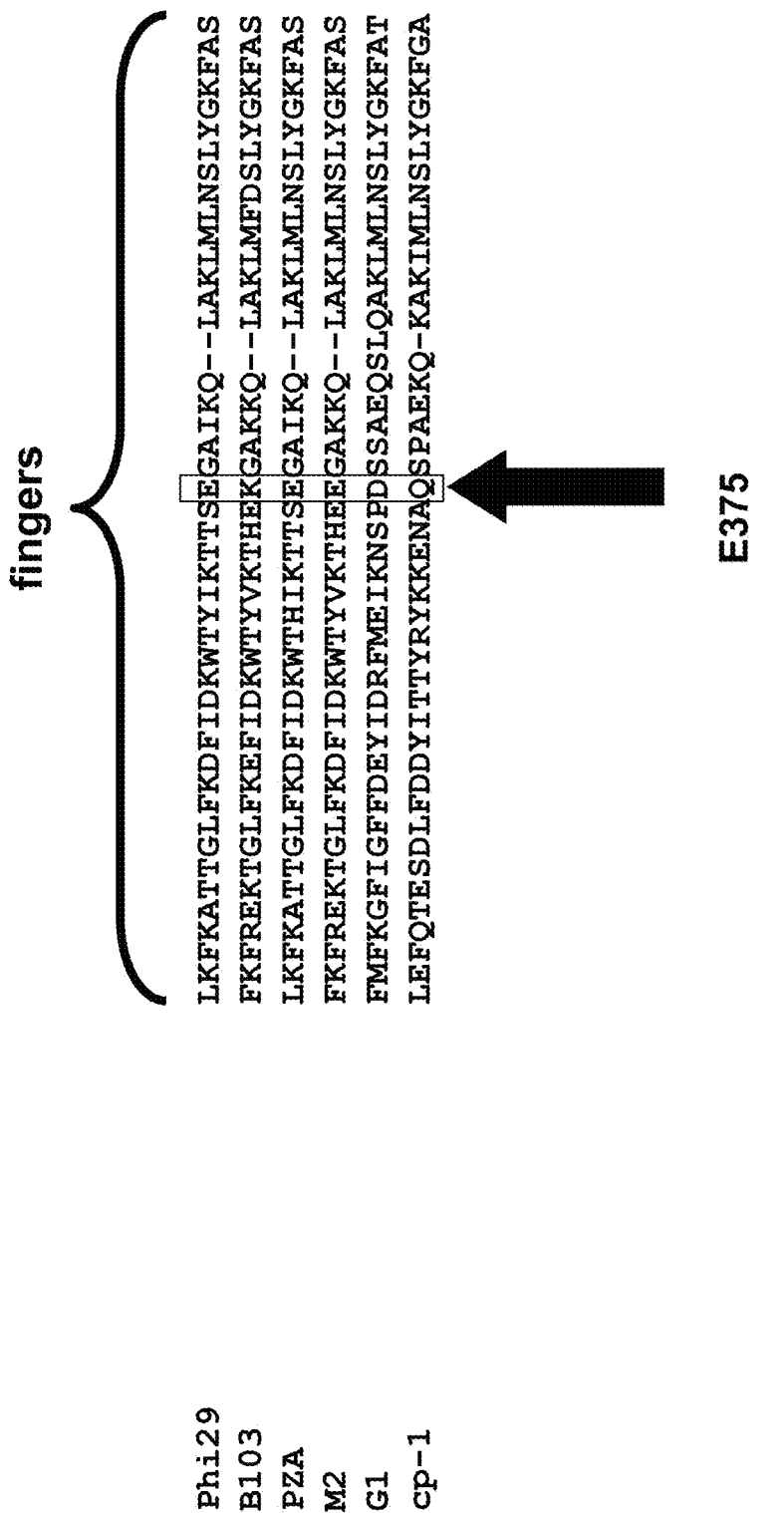
FIG. 3A presents a sequence alignment for Phi 29-like polymerases in the region surrounding E375 of Phi 29 (Phi29 SEQ ID NO:41, B103 SEQ ID NO:42, PZA SEQ ID NO:43, M2 SEQ ID NO:44, G1 SEQ ID NO:45, cp-1 SEQ ID NO:46).

FIG. 3A shows a sequence alignment of Phi 29-like polymerases in the region surrounding E375 of Phi 29. FIGS. 3B-3D illustrate the structure of the Phi 29 polymerase. The glutamate at position 375 (indicated by the arrow) is located proximal to the positively charged residues (K371, K379, K383; depicted in green with blue knobs) that contact the triphosphate moiety of the incoming dNTP. As illustrated in FIGS. 3E-3G, this negatively charged amino acid (E) was replaced with a positive one (H) in an attempt to coordinate the extra phosphate in the tetraphosphate nucleotide analogues. Additionally, the extra positive charge at this site may help coordinate triphosphate analogs. Analysis of the recombinant polymerase suggests that the E375H mutation has improved the kinetics of the enzyme for incorporating phosphate labeled nucleotide analogues (see Example 3 below). Mutant E375S was also constructed to introduce a neutral residue at this location and/or, e.g., to facilitate conformational change to enable function. See also SEQ ID NOs:4-7 and 25-28.

Figure 4D:
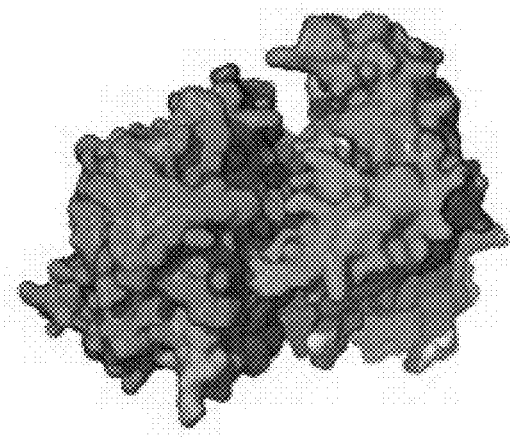
FIGS. 4B-4G illustrate the structure of Phi 29 (FIGS. 4B-4D) and an E486A mutant (FIGS. 4E-4G). Views of the structures from three different angles are shown.
Figure 4G:
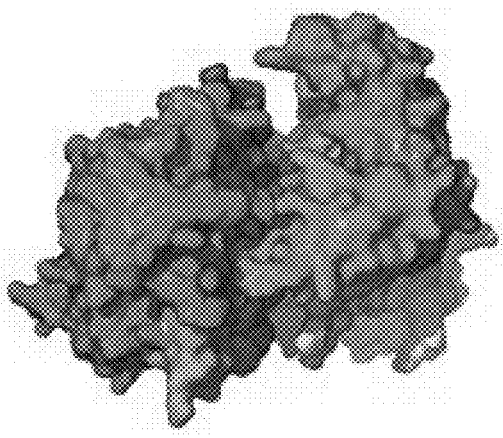
Figure 4C:
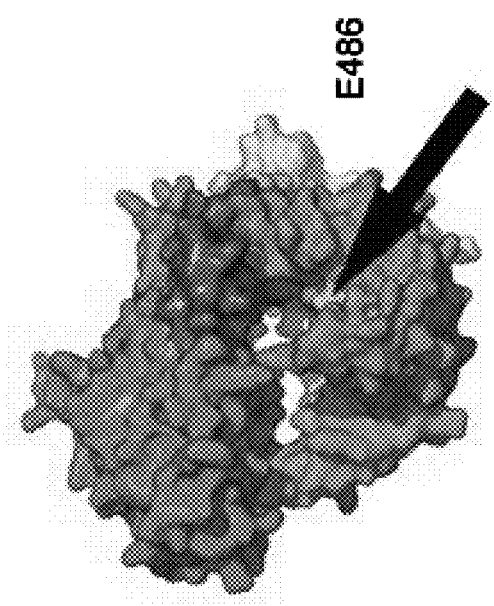
Figure 4F:
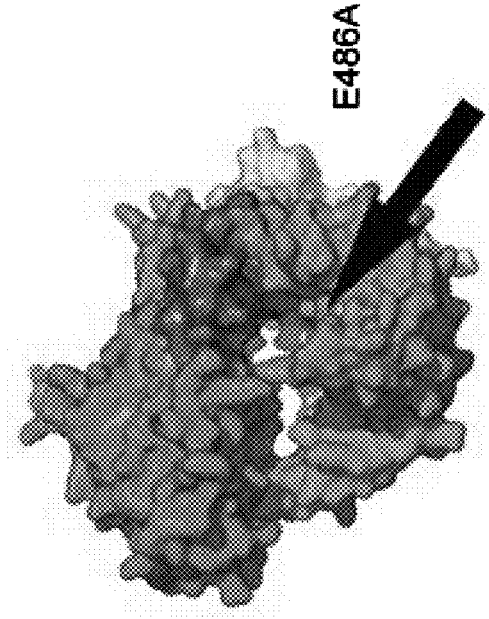
Figure 4B:
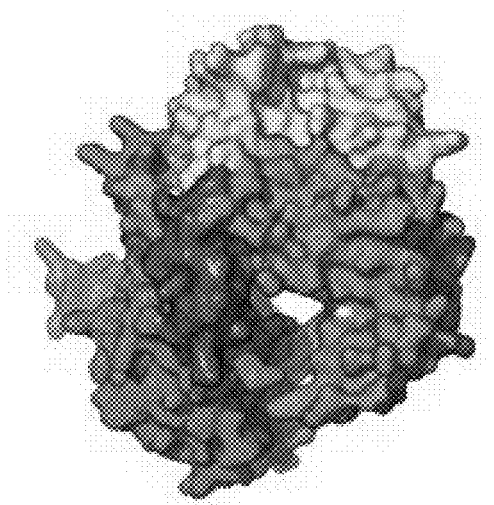
Figure 4E:
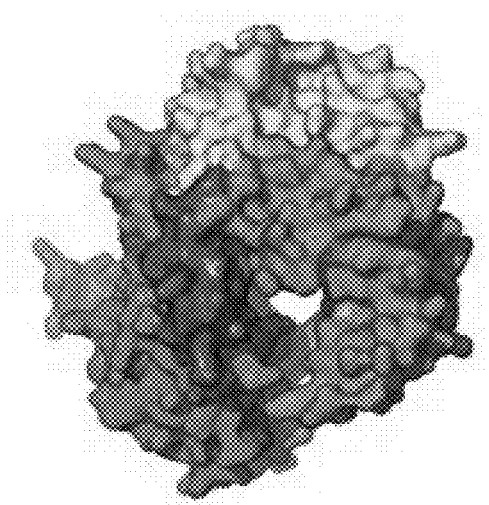

FIG. 4A shows a sequence alignment of Phi 29-like polymerases in the region surrounding E486 of Phi 29. FIGS. 4B-4D illustrate the structure of the Phi 29 polymerase; the location of E486 is indicated by an arrow. As illustrated in FIGS. 4E-4G, replacement of E486 by an alanine residue creates more room in the active site region near the catalytic carboxylates (D249 and D458, depicted in white) and removes a negative charge. As another example, replacement of E486 by an aspartic acid residue removes a carbon, decreasing steric interference with nucleotide analogue binding while retaining the negative charge. See also SEQ ID NOs:9-10 and 30-31.

Figure 5A:
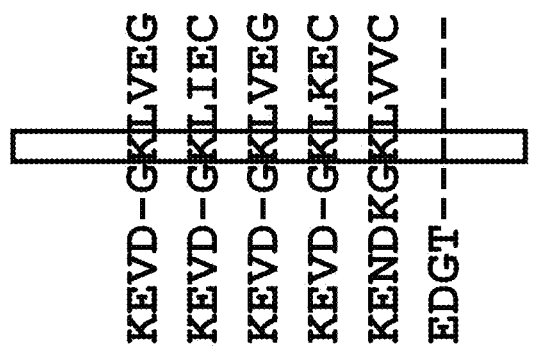
FIG. 5A shows a sequence alignment for Phi 29-like polymerases in the region surrounding K512 of Phi 29 (Phi29 SEQ ID NO:53, B103 SEQ ID NO:54, PZA SEQ ID NO:55, M2 SEQ ID NO:56, G1 SEQ ID NO:57, cp-1 SEQ ID NO:58).
Figure 5B:
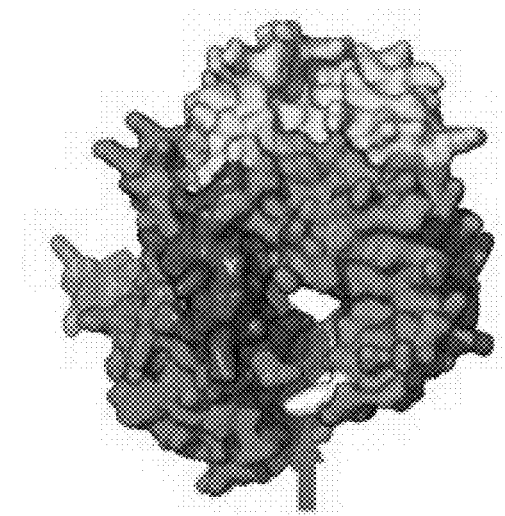
FIGS. 5B-5G illustrate the structure of Phi 29 (FIGS. 5B-5D) and a K512A mutant (FIGS. 5E-5G). Views of the structures from three different angles are shown.
Figure 5C:
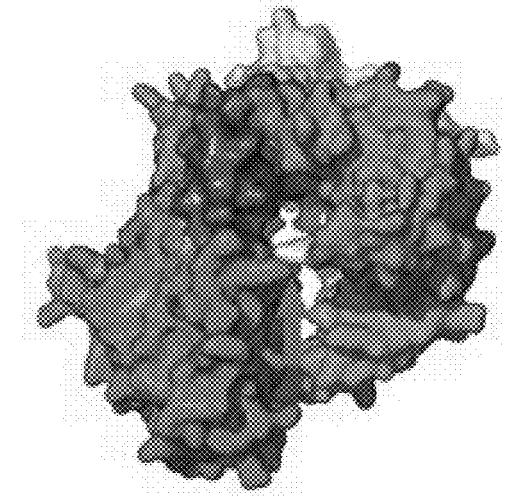
Figure 5D:
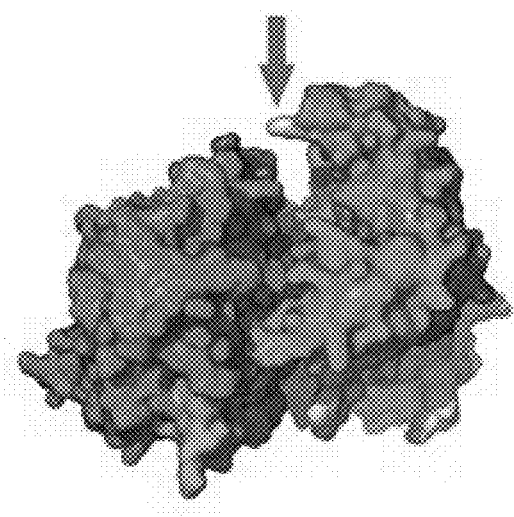
Figure 5E:
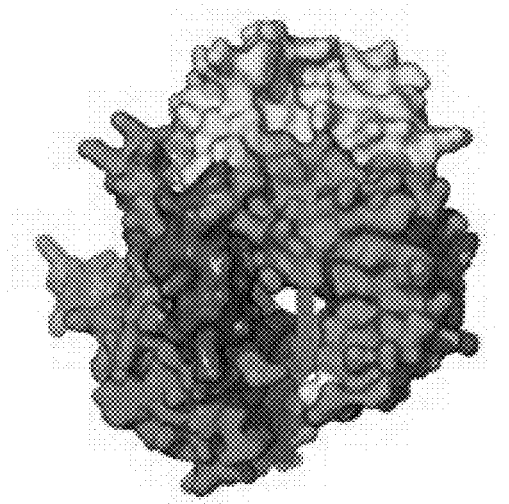
Figure 5F:
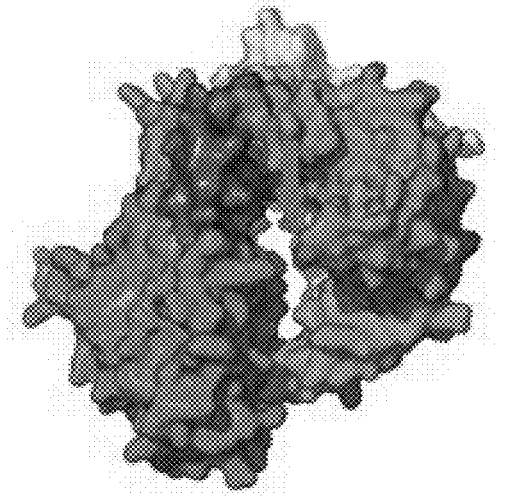
Figure 5G:
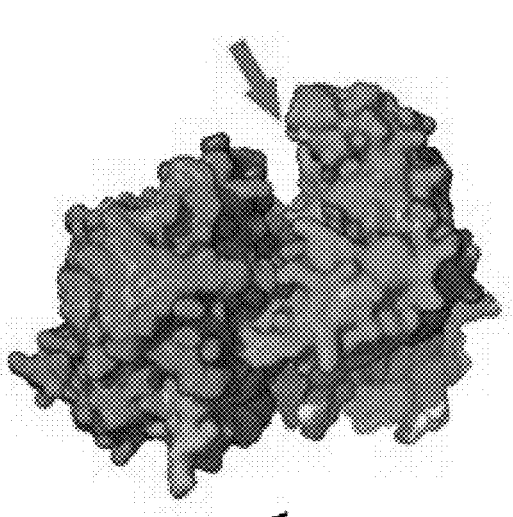

FIG. 5A shows a sequence alignment of Phi 29-like polymerases in the region surrounding K512 of Phi 29. FIGS. 5B-5D illustrate the structure of the Phi 29 polymerase. K512 (indicated by an arrow) juts out from the residue 505-525 domain and partially blocks the opening to the incoming dNTP binding site. As illustrated in FIGS. 5E-5G, replacement of K512 by an alanine residue reduces steric inhibition for entry of nucleotide analogues into the active site region, providing more space for them to get into the binding pocket. See also SEQ ID NOs:11 and 32.

Figure 6D:
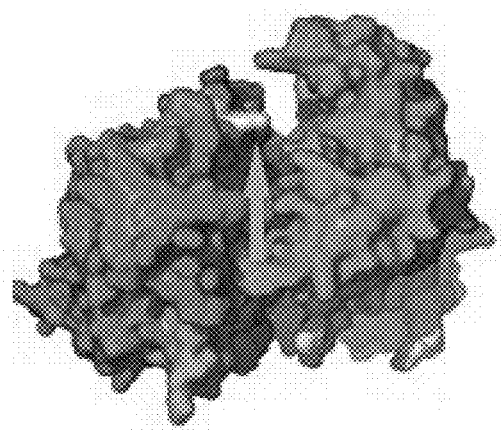
FIGS. 6B-6G illustrate the structure of Phi 29 (FIGS. 6B-6D) and a K135A mutant (FIGS. 6E-6G). Views of the structures from three different angles are shown.
Figure 6G:
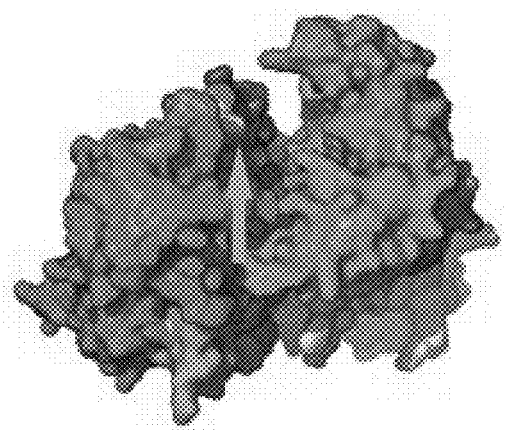
Figure 6C:
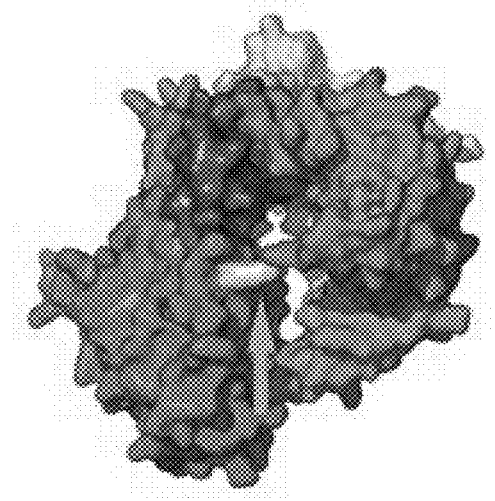
Figure 6F:
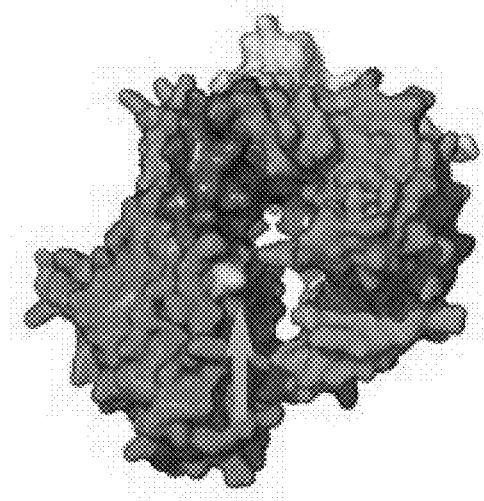
Figure 6B:
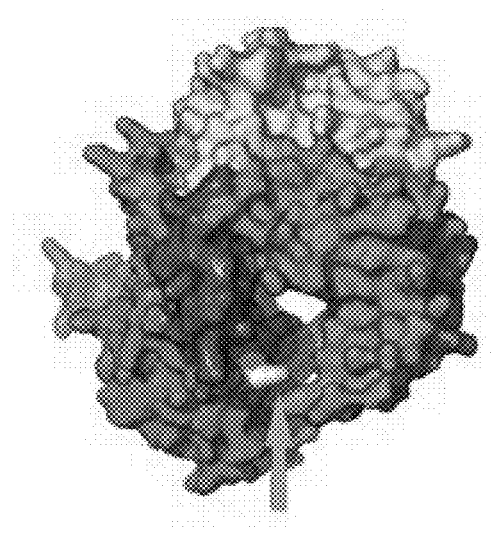
Figure 6E:
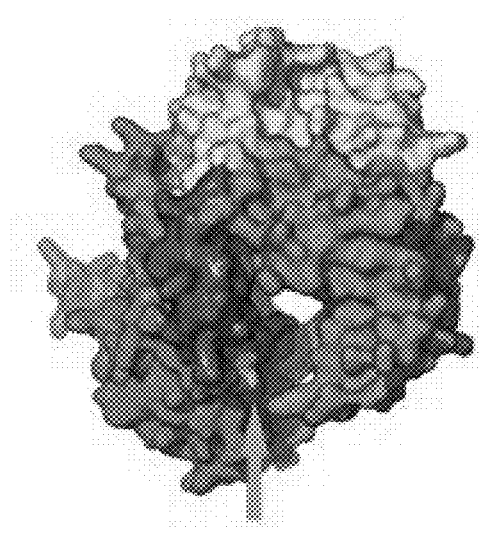

FIG. 6A shows a sequence alignment of Phi 29-like polymerases in the region surrounding K135 of Phi 29. FIGS. 6B-6D illustrate the structure of the Phi 29 polymerase. K135 (indicated by an arrow) juts into the opening to the incoming dNTP binding site. As illustrated in FIGS. 6E-6G, replacement of K135 by an alanine residue reduces steric inhibition for entry of nucleotide analogues into the active site region, providing more space for them to get into the binding pocket. See also SEQ ID NOs:3 and 24.

Example 3: Screening and Characterization of Recombinant Polymerases

Recombinant polymerases generated as in Example 2, or through essentially any other rational or random mutagenesis strategy, are optionally characterized to determine their properties for various natural and/or nucleotides. One exemplary five-step protocol for characterizing recombinant polymerases follows.

The recombinant polymerase is initially evaluated on the quality of the protein preparation and basic catalytic activity. The polymerase's activity is analyzed with natural (native) nucleotides, and its specific activity (units/mg) is determined. Only catalytically competent mutants are selected for the next steps.

The processivity (dissociation/kb) of the polymerase is estimated in a primer extension reaction performed in the presence of "Trap" (unlabeled competitor DNA or heparin). The processivity assay is designed to select mutants that retain the capability to synthesize a long DNA product in a continuous polymerization run (without polymerization reinitiation) with natural nucleotides. Mutants with a significant decrease in processivity are not selected for the next step.

Polymerization rate (bases/min) with four analogues at 10 μM (A488dA4P, A633dC4P, A546dG4P and A594dT4P) and circular template (AGTC, a 72mer circular template largely consisting of a repeating AGTC motif) is determined.

The most promising polymerase mutants are characterized by determination of the polymerization rate and Km for A488dC4P and A568dC4P and a subset of natural nucleotides (dATP, dGTP and dTTP), using a circular template (AGTC). Velocity is measured at several different concentrations of the analogs, A488dC4P (a representative good substrate) and A568dC4P (a representative less preferred substrate).

An initial selection for polymerase mutants with improved kinetics for terminal phosphate labeled nucleotide analogues is performed, using a primer extension assay with nucleotide analogues to determine rate with analogues under experimental conditions. Two separate experiments are typically performed, one in the presence of 10 M A488dC4P, 20 μM 3dNTPs-dCTP, and circular template (AGTC), and one in the presence of 10 M A568dC4P, 20 μM 3dNTPs-dCTP, and circular template (AGTC).

Other characteristics of the recombinant polymerase are optionally examined, including, for example, fidelity, residence time ($1/V_{max}$), exonuclease activity (e.g., at 10 μM, via extension of mismatched primer), active fraction (burst frequency), rate with dNTPs, dN5Ps, linker-only analogs, and/or FRET analogs, kinetics (ability to utilize analogs) with $Mg^{2+}$ vs. $Mn^{2+}$, sensitivity to photodamage, single-stranded DNA binding, monomeric state (e.g., using gel filtration or native gels), and/or shelf-life.

Results of protein quality evaluation and polymerization rate and kinetic constant determination for exemplary recombinant Phi 29 polymerases are presented in Tables 1 and 2, respectively.

TABLE 1

Initial characterization.

| Description | Concentration; Yield of Purified Polymerase | Specific Activity (units/mg) |
| --- | --- | --- |
| His-K135A-N62D | 3.7 uM; 1 mg | 12,454,000 |
| His-E375H-N62D | 7.4 uM; 1 mg | 10,945,000 |

TABLE 1-continued

Initial characterization.

| Description | Concentration; Yield of Purified Polymerase | Specific Activity (units/mg) |
| --- | --- | --- |
| His-E375S-N62D | 109 uM; 7 mg | 10,961,000 |
| His-E486A-N62D | 40 uM; 3.5 mg | 4,133,000 |
| His-E486D-N62D | 36 uM; 3.1 mg | 11,634,000 |
| His-K512A-N62D | 34 uM; 10 mg | 16,073,000 |
| His-NipTuck_1-N62D | 32 uM; 2.5 mg | 12,400,000 |
| His-NipTuck_2-N62D | 4.4 uM; 0.3 mg | 7,960,000 |

TABLE 2

Characterization of polymerization rate with natural and analogue nucleotides.

| A | B | C | D | E | F | G | H | I | J |
| --- | --- | --- | --- | --- | --- | --- | --- | --- | --- |
| GST-N62D | 780 | 1200 | 20 | 1660 | 74 | 346 | 236 | 65 | 0.9799 |
| His-N62D | 750 | 1020 | 21 | | | 391 | 237 | 68 | 0.9754 |
| His-K135A-N62D | 840 | 880 | 24 | | | 292 | 154 | 43 | 0.9801 |
| His-E375H-N62D | 780 | 950 | 8 | 930 | 11 | 411 | 366 | 123 | 0.9510 |
| His-E375S-N62D | 940 | 1190 | 15 | 1300 | 28 | 420 | 332 | 74 | 0.9815 |
| His-E486A-N62D | 1690 | | | | | 303 | 118 | 15 | 0.9875 |
| His-E486D-N62D | | | | | | 220 | 134 | 15 | 0.9885 |
| His-K512A-N62D | 1590 (630) | | | | | 359 | 196 | 34 | 0.9821 |
| His-NipTuck_1-N62D | 660 | 520 | 24 | | | 153 | 116 | 24 | 0.9585 |
| His-NipTuck_2-N62D | 540 (1840) | | | | | 147 | 129 | 28 | 0.9520 |

Column A: Description.
Column B: dTTP, dATP, dGTP (no G fork) V at 20 μM; determined by an assay with three native nucleotides (dGTP, dTTP and dATP).
Column C: A488dC4P, $k_{el}$ (bp/min); determined by examining the nucleotide analogue concentration dependence of the polymerization rate.
Column D: A488dC4P, Km; determined by examining the nucleotide analogue concentration dependence of the polymerization rate.
Column E: A568dC4P, $k_{el}$; determined by examining the nucleotide analogue concentration dependence of the polymerization rate.
Column F: A568dC4P, Km; determined by examining the nucleotide analogue concentration dependence of the polymerization rate.
Column G: A488dC4P, V at 10 μM; determined by an assay with a single analogue at low concentration (10uM) and three native nucleotides.
Column H: A568dC4P, V at 10 μM; determined by an assay with a single analogue at low concentration (10uM) and three native nucleotides.
Column I: A488dA4P, A633dC4P, A546dG4P, A594dT4P, V at 10 μM; determined by an assay with four terminally labeled nucleotide analogs.
Column J: Processivity ($kb^{-1}$); determined by a processivity assay.

Assay with a Single Analogue at Low Concentration (10 μM) and Three Native Nucleotides The Φ29 DNA polymerase (parental enzyme or mutant) was preincubated with DNA template (72 nucleotide circular DNA including mostly repetitive sequence AGTC) with annealed DNA primer. The preincubation mix includes three native nucleotides (dTTP, dATP and dGTP) and a terminal labeled nucleotide analogue (A488dC4P or A568dC4P) at 10 μM concentration. After a short preincubation, the reaction was started with MnCl$_2$. The reaction was stopped with EDTA, and the products were separated using agarose gel electrophoresis and stained with SYBR Gold (Invitrogen). The average length of the DNA generated with DNA polymerase was determined and used to estimate the polymerization rate. See, e.g., Table 2 Columns G and H.

Assay with Four Terminally Labeled Nucleotide Analogs

The procedure is basically as described above in the section entitled "Assay with a single analogue at low concentration (10 μM) and three native nucleotides," with the exception that in this assay all nucleotides are terminally labeled (A488dA4P, A633dC4P, A546dG4P, A594dT4P all at 10 μM). See, e.g., Table 2 Column I.

Assay with Three Native Nucleotides (dGTP, dTTP and dATP)

The Φ29 DNA polymerase (parental enzyme or mutant) was preincubated with DNA template (circular DNA including mostly repetitive sequence CAT, no G residues) with annealed DNA primer; the preincubation mix includes three native nucleotides (dTTP, dATP and dGTP). All subsequent steps were basically as described above in the section entitled "Assay with a single analogue at low concentration (10 μM) and three native nucleotides." See, e.g., Table 2 Column B.

The Nucleotide Analogue Concentration Dependence of the Polymerization Rate

The Φ29 DNA polymerase (parental enzyme or mutant) was preincubated with a DNA template (72 nucleotide circular DNA including mostly repetitive sequence AGTC) with annealed primer. The preincubation mix includes also three native nucleotides (dTTP, dATP and dGTP 20 μM each) and various concentrations of the terminally labeled analogue (A488dC4P or A568dC4P). All subsequent steps were basically as described above in the section entitled "Assay with a single analogue at low concentration (10 μM) and three native nucleotides." An average length of the DNA products generated with DNA polymerase at an individual analogue concentration was determined, and the results were fitted with the equation $k = k_{el} * [S] * (K_d + [S])^{-1}$ where k is the observed polymerization rate, $k_{el}$ is the polymerization rate at saturating substrate concentration ($k_{el}$ measures incorporation of multiple residues), and [S] is substrate concentration. See, e.g., Table 2 Columns C, D, E, and F.

Processivity Assay

The Φ29 DNA polymerase (parental enzyme or mutant) was preincubated with DNA template (72 nucleotide circular DNA including mostly repetitive sequence AGTC) with annealed DNA primer. After a short preincubation, the reaction was started with a starting mix including MnCl$_2$, dNTP and heparin. Including the heparin in the reaction prevents polymerization from reinitiating after the polymerase dissociates from the template/primer, so that all generated DNA products are a result of continuous polymerization runs. After 20 min incubation, the reaction was stopped with EDTA and the products were separated using agarose gel electrophoresis and stained with SYBR Gold (Invitrogen). The DNA products were analyzed basically as described in Bibillo A, Eickbush T H. *J Biol Chem.* 2002 Sep. 20; 277(38):34836-45, Epub 2002 Jul. 5. The results were fitted with single exponential equation A*exp(-P$_{off}$*kb) where A is amplitude, P$_{off}$ is the probability of premature polymerase dissociation, and kb is DNA length (1000 nucleotides). The probability of chain elongation (processivity) can be readily calculated by subtracting the P$_{off}$ value from 1.0. See, e.g., Table 2 Column J.

Sequences of Exemplary Recombinant Polymerases

Amino acid and polynucleotide sequences of wild-type Phi 29 and exemplary recombinant polymerases are presented in Table 3.

TABLE 3

Sequences.

| SEQ ID NO: | Notes | Sequence |
|---|---|---|
| 1 | wild-type Phi 29 amino acid sequence | mkhmprkmys cdfetttkve dcrvwaygym niedhseyki gnsldefmaw vlkvqadlyf hnlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttsegaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdiymkevd gklvegspdd ytdikfsvkc agmtdkikke vtfenfkvgf srkmkpkpvq vpggvvlvdd tftik |
| 2 | N62D amino acid sequence (tagged) | mspilgywki kglvqptrll leyleekyee hlyerdegdk wrnkkfelgl efpnlpyyid gdvkltqsma iiryiadkhn mlggcpkera eismlegavl dirygvsria yskdfetlkv dflsklpeml kmfedrlchk tylngdhvth pdfmlydald vvlymdpmcl dafpklvcfk krieaipqid kylksskyia wplqgwqatf gggdhppksd gstsgsghhh hhhsaglvpr gstaigmket aaakferqhm dspdlgtggg sgddddkspm gyrgsefmkh mprkmyscdf etttkvedcr vwaygymnie dhseykigns ldefmawvlk vqadlyfhdl kfdgafiinw lerngfkwsa dglpntynti isrmgqwymi diclgykgkr kihtviydsl kklpfpvkki akdfkltvlk gdidyhkerp vgykitpeey ayikndiqii aealliqfkq gldrmtagsd slkgfkdiit tkkfkkvfpt lslgldkevr yayrggftwl ndrfkekeig egmvfdvnsl ypaqmysrll pygepivfeg kyvwdedypl hiqhircefe lkegyiptiq ikrsrfykgn eylkssggei adlwlsnvdl elmkehydly nveyisglkf kattglfkdf idkwtyiktt segaikqlak lmlnslygkf asnpdvtgkv pylkengalg frlgeeetkd pvytpmgvfi tawaryttit aaqacydrii ycdtdsihlt gteipdvikd ivdpkklgyw ahestfkrak ylrqktyiqd iymkevdgkl vegspddytd ikfsvkcagm tdkikkevtf enfkvgfsrk mkpkpvqvpg gvvlvddtft ik |
| 3 | K135A-N62D amino acid sequence (tagged) | mspilgywki kglvqptrll leyleekyee hlyerdegdk wrnkkfelgl efpnlpyyid gdvkltqsma iiryiadkhn mlggcpkera eismlegavl dirygvsria yskdfetlkv dflsklpeml kmfedrlchk tylngdhvth pdfmlydald vvlymdpmcl dafpklvcfk krieaipqid kylksskyia wplqgwqatf gggdhppksd gstsgsghhh hhhsaglvpr gstaigmket aaakferqhm dspdlgtggg sgddddkspm gyrgsefmkh mprkmyscdf etttkvedcr vwaygymnie dhseykigns ldefmawvlk vqadlyfhdl kfdgafiinw lerngfkwsa dglpntynti isrmgqwymi diclgykgkr kihtviydsl kklpfpvkki aadfkltvlk gdidyhkerp vgykitpeey ayikndiqii aealliqfkq gldrmtagsd slkgfkdiit tkkfkkvfpt lslgldkevr yayrggftwl ndrfkekeig egmvfdvnsl ypaqmysrll pygepivfeg kyvwdedypl hiqhircefe lkegyiptiq ikrsrfykgn eylkssggei adlwlsnvdl elmkehydly nveyisglkf kattglfkdf idkwtyiktt segaikqlak lmlnslygkf asnpdvtgkv pylkengalg frlgeeetkd pvytpmgvfi tawaryttit aaqacydrii ycdtdsihlt gteipdvikd ivdpkklgyw ahestfkrak ylrqktyiqd iymkevdgkl vegspddytd ikfsvkcagm tdkikkevtf enfkvgfsrk mkpkpvqvpg gvvlvddtft ik |
| 4 | E375H-N62D amino acid sequence (tagged) | mspilgywki kglvqptrll leyleekyee hlyerdegdk wrnkkfelgl efpnlpyyid gdvkltqsma iiryiadkhn mlggcpkera eismlegavl dirygvsria yskdfetlkv dflsklpeml kmfedrlchk tylngdhvth pdfmlydald vvlymdpmcl dafpklvcfk krieaipqid kylksskyia wplqgwqatf gggdhppksd gstsgsghhh hhhsaglvpr gstaigmket aaakferqhm dspdlgtggg sgddddkspm gyrgsefmkh mprkmyscdf etttkvedcr vwaygymnie dhseykigns ldefmawvlk vqadlyfhdl |

TABLE 3-continued

Sequences.

| SEQ ID NO: | Notes | Sequence |
|---|---|---|
| | | kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt shgaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgkl<br>vegspddytd ikfsvkcagm tdkikkevtf enfkvgfsrk mkpkpvqvpg<br>gvvlvddtft ik |
| 5 | E375S-<br>N62D amino<br>acid<br>sequence<br>(tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt ssgaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgkl<br>vegspddytd ikfsvkcagm tdkikkevtf enfkvgfsrk mkpkpvqvpg<br>gvvlvddtft ik |
| 6 | E375K-<br>N62D amino<br>acid<br>sequence<br>(tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt skgaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgkl<br>vegspddytd ikfsvkcagm tdkikkevtf enfkvgfsrk mkpkpvqvpg<br>gvvlvddtft ik |
| 7 | E375R-<br>N62D amino<br>acid<br>sequence<br>(tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt srgaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgkl<br>vegspddytd ikfsvkcagm tdkikkevtf enfkvgfsrk mkpkpvqvpg<br>gvvlvddtft ik |
| 8 | L384R-<br>N62D amino<br>acid | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth |

TABLE 3-continued

Sequences.

| SEQ ID NO: | Notes | Sequence |
| --- | --- | --- |
| | sequence (tagged) | pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak rmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgkl<br>vegspddytd ikfsvkcagm tdkikkevtf enfkvgfsrk mkpkpvqvpg<br>gvvlvddtft ik |
| 9 | E486A-N62D amino acid sequence (tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahastfkrak ylrqktyiqd iymkevdgkl<br>vegspddytd ikfsvkcagm tdkikkevtf enfkvgfsrk mkpkpvqvpg<br>gvvlvddtft ik |
| 10 | E486D-N62D amino acid sequence (tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak lmlnslygkf asnpdvtgkv pylkengalg<br>frlgeeetkd pvytpmgvfi tawaryttit aaqacydrii ycdtdsihlt<br>gteipdvikd ivdpkklgyw andstfkrak ylrqktyiqd iymkevdgkl<br>vegspddytd ikfsvkcagm tdkikkevtf enfkvgfsrk mkpkpvqvpg<br>gvvlvddtft ik |
| 11 | K512A-N62D amino acid sequence (tagged) | mspilgywki kglvqptrll leyleekyee hlyerdegdk wrnkkfelgl<br>efpnlpyyid gdvkltqsma iiryiadkhn mlggcpkera eismlegavl<br>dirygvsria yskdfetlkv dflsklpeml kmfedrlchk tylngdhvth<br>pdfmlydald vvlymdpmcl dafpklvcfk krieaipqid kylksskyia<br>wplqgwqatf gggdhppksd gstsgsghhh hhhsaglvpr gstaigmket<br>aaakferqhm dspdlgtggg sgddddkspm gyrgsefmkh mprkmyscdf<br>etttkvedcr vwaygymnie dhseykigns ldefmawvlk vqadlyfhdl<br>kfdgafiinw lerngfkwsa dglpntynti isrmgqwymi diclgykgkr<br>kihtviydsl kklpfpvkki akdfkltvlk gdidyhkerp vgykitpeey<br>ayikndiqii aealliqfkq gldrmtagsd slkgfkdiit tkkfkkvfpt<br>lslgldkevr yayrggftwl ndrfkekeig egmvfdvnsl ypaqmysrll<br>pygepivfeg kyvwdedypl hiqhircefe lkegyiptiq ikrsrfykgn<br>eylkssggei adlwlsnvdl elmkehydly nveyisglkf kattglfkdf<br>idkwtyiktt segaikqlak lmlnslygkf asnpdvtgkv pylkengalg<br>frlgeeetkd pvytpmgvfi tawaryttit aaqacydrii ycdtdsihlt<br>gteipdvikd ivdpkklgyw ahestfkrak ylrqktyiqd iymkevdgal<br>vegspddytd ikfsvkcagm tdkikkevtf enfkvgfsrk mkpkpvqvpg<br>gvvlvddtft ik |

TABLE 3-continued

Sequences.

| SEQ ID NO: | Notes | Sequence |
|---|---|---|
| 12 | NipTuck_1-N62D amino acid sequence (deletion of residues 505-525) (tagged) | mspilgywki kglvqptrll leyleekyee hlyerdegdk wrnkkfelgl efpnlyyid gdvkltqsma iiryiadkhn mlggcpkera eismlegavl dirygvsria yskdfetlkv dflsklpeml kmfedrlchk tylngdhvth pdfmlydald vvlymdpmcl dafpklvcfk krieaipqid kylksskyia wplqgwqatf gggdhppksd gstsgsghhh hhhsaglvpr gstaigmket aaakferqhm dspdlgtggg sgddddkspm gyrgsefmkh mprkmyscdf etttkvedcr vwaygymnie dhseykigns ldefmawvlk vqadlyfhdl kfdgafiinw lerngfkwsa dglpntynti isrmgqwymi diclgykgkr kihtviydsl kklpfpvkki akdfkltvlk gdidyhkerp vgykitpeey ayikndiqii aealliqfkq gldrmtagsd slkgfkdiit tkkfkkvfpt lslgldkevr yayrggftwl ndrfkekeig egmvfdvnsl ypaqmysrll pygepivfeg kyvwdedypl hiqhircefe lkegyiptiq ikrsrfykgn eylkssggei adlwlsnvdl elmkehydly nveyisglkf kattglfkdf idkwtyiktt segaikqlak lmlnslygkf asnpdvtgkv pylkengalg frlgeeetkd pvytpmgvfi tawaryttit aaqacydrii ycdtdsihlt gteipdvikd ivdpkklgyw ahestfkrak ylrqktyiqd ikdgefsvkc agmtdkikke vtfenfkvgf srkmkpkpvq vpggvvlvdd tftik |
| 13 | NipTuck_2-N62D amino acid sequence (deletion of residues 505-525) (tagged) | mspilgywki kglvqptrll leyleekyee hlyerdegdk wrnkkfelgl efpnlyyid gdvkltqsma iiryiadkhn mlggcpkera eismlegavl dirygvsria yskdfetlkv dflsklpeml kmfedrlchk tylngdhvth pdfmlydald vvlymdpmcl dafpklvcfk krieaipqid kylksskyia wplqgwqatf gggdhppksd gstsgsghhh hhhsaglvpr gstaigmket aaakferqhm dspdlgtggg sgddddkspm gyrgsefmkh mprkmyscdf etttkvedcr vwaygymnie dhseykigns ldefmawvlk vqadlyfhdl kfdgafiinw lerngfkwsa dglpntynti isrmgqwymi diclgykgkr kihtviydsl kklpfpvkki akdfkltvlk gdidyhkerp vgykitpeey ayikndiqii aealliqfkq gldrmtagsd slkgfkdiit tkkfkkvfpt lslgldkevr yayrggftwl ndrfkekeig egmvfdvnsl ypaqmysrll pygepivfeg kyvwdedypl hiqhircefe lkegyiptiq ikrsrfykgn eylkssggei adlwlsnvdl elmkehydly nveyisglkf kattglfkdf idkwtyiktt segaikqlak lmlnslygkf asnpdvtgkv pylkengalg frlgeeetkd pvytpmgvfi tawaryttit aaqacydrii ycdtdsihlt gteipdvikd ivdpkklgyw ahestfkrak ylrqktyiqd idgfsvkcag mtdkikkevt fenfkvgfsr kmkpkpvqvp ggvvlvddtf tik |
| 14 | N62D nucleotide sequence - pET41 N62D 1 plasmid | tggcgaatgggacgcgccctgtagcggcgcattaagcgcggcgggtgtgg tggttacgcgcagcgtgaccgctacacttgccagcgccctagcgcccgct cctttcgctttcttcccttcctttctcgccacgttcgccggctttcccg tcaagctctaaatcgggggctccctttagggttccgatttagtgctttac ggcacctcgaccccaaaaaacttgattagggtgatggttcacgtagtggg ccatcgccctgatagacggtttttcgccctttgacgttggagtccacgtt ctttaatagtggactcttgttccaaactggaacaacactcaaccctatct cggtctattcttttgatttataagggattttgccgatttcggcctattgg ttaaaaaatgagctgatttaacaaaaatttaacgcgaattttaacaaaat attaacgtttacaatttcaggtggcacttttcggggaaatgtgcgcggaa cccctatttgtttatttttctaaatacattcaaatatgtatccgctcatg aattaattcttagaaaaactcatcgagcatcaaatgaaactgcaatttat tcatatcaggattatcaataccatatttttgaaaaagccgtttctgtaat gaaggagaaaactcaccgaggcagttccataggatggcaagatcctggta tcggtctgcgattccgactcgtccaacatcaatacaacctattaatttcc cctcgtcaaaataaggttatcaagtgagaaatcaccatgagtgacgact gaatccggtgagaatggcaaaagtttatgcatttctttccagacttgttc aacaggccagccattacgctcgtcatcaaaatcactcgcatcaaccaaac cgttattcattcgtgattgcgcctgagcgagacgaaatacgcgatcgctg ttaaaaggacaattacaaacaggaatcgaatgcaacggcgcaggaacac tgccagcgcatcaacaatattttcacctgaatcaggatattcttctaata cctggaatgctgttttcccggggatcgcagtggtgagtaaccatgcatca tcaggagtacggataaaatgcttgatggtcggaagaggcataaattccgt cagccagtttagtctgaccatctcatctgtaacatcattggcaacgctac ctttgccatgtttcagaaacaactctggcgcatcgggcttcccatacaat cgatagattgtcgcacctgattgcccgacattatcgcgagcccatttata cccatataaatcagcatccatgttggaatttaatcgcggcctagagcaag acgtttcccgttgaatatggctcataacaccccttgtattactgtttatg taagcagacagttttattgttcatgaccaaaatcccttaacgtgagtttt cgttccactgagcgtcagaccccgtagaaaagatcaaaggatcttcttga gatcctttttttctgcgcgtaatctgctgcttgcaaacaaaaaaaccacc gctaccagcggtggtttgtttgccggatcaagagctaccaactctttttc cgaaggtaactggcttcagcagagcgcagataccaaatactgtccttcta gtgtagccgtagttaggccaccacttcaagaactctgtagcaccgcctac atacctcgctctgctaatcctgttaccagtggctgctgccagtggcgata agtcgtgtcttaccgggttggactcaagacgatagttaccggataaggcg cagcggtcgggctgaacggggggttcgtgcacacagcccagcttggagcg aacgacctacaccgaactgagatacctacagcgtgagctatgagaaagcg |

TABLE 3-continued

Sequences.

| SEQ ID NO: | Notes | Sequence |
|---|---|---|
| | | ccacgcttcccgaagggagaaaggcggacaggtatccggtaagcggcagg |
| | | gtcggaacaggagagcgcacgagggagcttccaggggggaaacgcctggta |
| | | tctttatagtcctgtcgggtttcgccacctctgacttgagcgtcgatttt |
| | | tgtgatgctcgtcaggggggcggagcctatggaaaaacgccagcaacgcg |
| | | gccttttacggttcctggccttttgctggccttttgctcacatgttctt |
| | | tcctgcgttatcccctgattctgtggataaccgtattaccgcctttgagt |
| | | gagctgataccgctcgccgcagccgaacgaccgagcgcagcgagtcagtg |
| | | agcgaggaagcggaagagcgcctgatgcggtattttctccttacgcatct |
| | | gtgcggtatttcacaccgcatatatggtgcactctcagtacaatctgctc |
| | | tgatgccgcatagttaagccagtatacactccgctatcgctacgtgactg |
| | | ggtcatggctgcgccccgacaccgccaacacccgctgacgcgccctgac |
| | | gggcttgtctgctcccggcatccgcttacagacaagctgtgaccgtctcc |
| | | gggagctgcatgtgtcagaggttttcaccgtcatcaccgaaacgcgcgag |
| | | gcagctgcggtaaagctcatcagcgtggtcgtgaagcgattcacagatgt |
| | | ctgcctgttcatccgcgtccagctcgttgagtttctccagaagcgttaat |
| | | gtctggcttctgataaagcgggccatgttaagggcggttttttcctgttt |
| | | ggtcactgatgcctccgtgtaaggggatttctgttcatgggggtaatga |
| | | taccgatgaaacgagagaggatgctcacgatacgggttactgatgatgaa |
| | | catgcccggttactggaacgttgtgagggtaaacaactggcggtatggat |
| | | gcggcgggaccagagaaaaatcactcagggtcaatgccagcgcttcgtta |
| | | atacagatgtaggtgttccacagggtagccagcagcatcctgcgatgcag |
| | | atccggaacataatggtgcagggcgctgacttccgcgtttccagacttta |
| | | cgaaacacggaaaccgaagaccattcatgttgttgctcaggtcgcagacg |
| | | ttttgcagcagcagtcgcttcacgttcgctcgcgtatcggtgattcattc |
| | | tgctaaccagtaaggcaaccccgccagcctagccgggtcctcaacgacag |
| | | gagcacgatcatgctagtcatgccccgcgcccaccggaaggagctgactg |
| | | ggttgaaggctctcaagggcatcggtcgagatcccggtgcctaatgagtg |
| | | agctaacttacattaattgcgttgcgctcactgcccgctttccagtcggg |
| | | aaacctgtcgtgccagctgcattaatgaatcggccaacgcgcggggagag |
| | | gcggtttgcgtattgggcgccagggtggtttttcttttcaccagtgagac |
| | | gggcaacagctgattgcccttcaccgcctggccctgagagagttgcagca |
| | | agcggtccacgctggtttgccccagcaggcgaaaatcctgtttgatggtg |
| | | gttaacggcgggatataacatgagctgtcttcggtatcgtcgtatcccac |
| | | taccgagatgtccgcaccaacgcgcagcccggactcggtaatggcgcgca |
| | | ttgcgcccagcgccatctgatcgttggcaaccagcatcgcagtgggaacg |
| | | atgccctcattcagcatttgcatggtttgttgaaaaccggacatggcact |
| | | ccagtcgccttcccgttccgctatcggctgaatttgattgcgagtgagat |
| | | atttatgccagccagccagacgcagacgcgccgagacagaacttaatggg |
| | | cccgctaacagcgcgatttgctggtgacccaatgcgaccagatgctccac |
| | | gcccagtcgcgtaccgtcttcatgggagaaaataatactgttgatgggtg |
| | | tctggtcagagacatcaagaaataacgccggaacattagtgcaggcagct |
| | | tccacagcaatggcatcctggtcatccagcggatagttaatgatcagccc |
| | | actgacgcgttgcgcgagaagattgtgcaccgccgctttacaggcttcga |
| | | cgccgcttcgttctaccatcgacaccaccacgctggcacccagttgatcg |
| | | gcgcgagatttaatcgccgcgacaatttgcgacggcgcgtgcagggccag |
| | | actggaggtggcaacgccaatcagcaacgactgtttgcccgccagttgtt |
| | | gtgccacgcggttgggaatgtaattcagctccgccatcgccgcttccact |
| | | ttttcccgcgttttcgcagaaacgtggctggcctggttcaccacgcggga |
| | | aacggtctgataagagacaccggcatactctgcgacatcgtataacgtta |
| | | ctggtttcacattcaccaccctgaattgactctcttccgggcgctatcat |
| | | gccataccgcgaaaggttttgcgccattcgatggtgtccgggatctcgac |
| | | gctctcccttatgcgactcctgcattaggaagcagcccagtagtaggttg |
| | | aggccgttgagcaccgccgccgcaaggaatggtgcatgcaaggagatggc |
| | | gcccaacagtcccccggccacggggcctgccaccatacccacgccgaaac |
| | | aagcgctcatgagcccgaagtggcgagcccgatcttccccatcggtgatg |
| | | tcggcgatataggcgccagcaaccgcacctgtggcgccggtgatgccggc |
| | | cacgatgcgtccggcgtagaggatcgagatcgatctcgatcccgcgaaat |
| | | taatacgactcactatagggggaattgtgagcggataacaattcccctcta |
| | | gaaataattttgtttaactttaagaaggagatatacatatgtcccctata |
| | | ctaggttattggaaaattaagggccttgtgcaacccactcgacttcttt |
| | | ggaatatcttgaagaaaaatatgaagagcatttgtatgagcgcgatgaag |
| | | gtgataaatggcgaaacaaaagtttgaattgggtttggagtttcccaat |
| | | cttccttattatattgatggtgatgttaaattaacacagtctatggccat |
| | | catacgttatatagctgacaagcacaacatgtgggtggttgtccaaaag |
| | | agcgtgcagagatttcaatgcttgaaggagcggttttggatattagatac |
| | | ggtgtttcgagaattgcatatagtaaagactttgaaactctcaaagttga |
| | | ttttcttagcaagctacctgaaatgctgaaaatgttcgaagatcgtttat |
| | | gtcataaaacatatttaaatggtgatcatgtaacccatcctgacttcatg |
| | | ttgtatgacgctcttgatgttgttttatacatgaccaatgtgcctgga |
| | | tgcgttcccaaaattagtttgttttaaaaaacgtattgaagctatcccac |
| | | aaaattgataagtacttgaaatccagcaagtatatagcatggcctttgcag |
| | | ggctggcaagccacgtttggtggtggcgaccatcctccaaaatcggatgg |
| | | ttcaactagtggttctggtcatcaccatcaccatcactccgcgggtctgg |
| | | tgccacgcggtagtactgcaattggtatgaaagaaaccgctgctgctaaa |

TABLE 3-continued

Sequences.

| SEQ ID NO: | Notes | Sequence |
|---|---|---|
| | | ttcgaacgccagcacatggacagcccagatctgggtaccggtggtggctc cggtgatgacgacgacaagagtcccatgggatatcggggatccgaattca tgaagcatatgccgagaaagatgtatagttgtgactttgagacaactact aaagtggaagactgtagggtatgggcgtatggttatatgaatatagaaga tcacagtgagtacaaaataggtaatagcctggatgagtttatggcgtggg tgttgaaggtacaagctgatctatatttccatgatctcaaatttgacgga gcttttatcattaactggttggaacgtaatggttttaagtggtcggctga cggattgccaaacacatataatacgatcatatctcgcatgggacaatggt acatgattgatatatgtttaggctacaaagggaaacgtaagatacataca gtgatatatgacagcttaaagaaactaccgtttcctgttaagaagatagc taaagactttaaactaactgttcttaaaggtgatattgattaccacaaag aaagaccagtcggctataagataacacccgaagaatacgcctatattaaa aacgatattcagattattgcggaagctctgttaattcagtttaagcaagg tttagaccggatgacagcaggcagtgacagtctaaaaggtttcaaggata ttataaccactaagaaattcaaaaaggtgtttcctacattggtctcttgga ctcgataaggaagtgagatacgcctatagaggtggttttacatggttaaa tgataggttcaaagaaaaagaaatcggagaaggcatggtcttcgatgtta atagtctatatcctgcacagatgtatagtcgtctccttccatatggtgaa cctatagtattcgagggtaaatacgtttgggacgaagattacccactaca catacagcatatcagatgtgagttcgaattgaaagagggctatatacccca ctatacagataaaaagaagtaggttttataaaggtaatgagtacctaaaa agtagcggcggggagatagccgacctctggttgtcaaatgtagacctaga attaatgaaagaacactacgatttatataacgttgaatatatcagcggct taaaatttaaagcaactacaggtttgtttaaagatttatagataaatgg acgtacatcaagacgacatcagaaggagcgatcaagcaactagcaaaact gatgttaaacagtctatacggtaaattcgctagtaaccctgatgttacag ggaaagtcccttatttaaaagagaatggggcgctaggtttcagacttgga gaagaggaaacaaaagaccctgtttatacacctatgggcgttttcatcac tgcatgggctagatacacgacaattacagcggcacaggcttgttatgatc ggataatatactgtgatactgacagcatacatttaacgggtacagagata cctgatgtaataaaagatatagttgaccctaagaaatttgggatactgggc acatgaaagtacattcaaaagagctaaatatctgagacagaagacctata tcaagacatctatatgaaagaagtagatggtaagttagtagaaggtagt ccagatgattacactgatataaaatttagtgttaaatgtgcgggaatgac tgacaagattaagaaagaggttacgtttgagaatttcaaagtcggattca gtcggaaaatgaagcctaagcctgtgcaagtgccgggcggggtggttctg gttgatgacacattcacaatcaaataagaattctgtacaggccttggcgc gcctgcaggcgagctccgtcgacaagcttgcggccgcactcgagcaccac caccaccaccaccactaattgattaatacctaggctgctaaacaaag cccgaaaggaagctgagttggctgctgccaccgctgagcaataactagca taaccccttgggcctctaaacgggtcttgaggggttttttgctgaaagg aggaactatatccggat |
| 15 | K135A-N62D nucleotide sequence | atgaagcacatgccgagaaagatgtatagttgtgactttgagacaactactaaagtggaagactgtaggg tatgggcgtatggttatatgaatatagaagatcacagtgagtacaaaataggtaatagcctggatgagtt tatggcgtgggtgttgaaggtacaagctgatctatatttccatgatctcaaatttgacggagcttttatc attaactggttggaacgtaatggttttaagtggtcggctgacggattgccaaacacatataatacgatca tatctcgcatgggacaatggtacatgattgatatatgtttaggctacaaagggaaacgtaagatacatac agtgatatgacagcttaaagaaactaccgtttcctgttaagaagatagctgccgactttaaactaact gttcttaaaggtgatattgattaccacaaagaaagaccagtcggctataagataacacccgaagaatacg cctatattaaaaacgatattcagattattgcggaagctctgttaattcagtttaagcaaggtttagaccg gatgacagcaggcagtgacagtctaaaaggtttcaaggatattataaccactaagaaattcaaaaaggtg tttcctacattgagtcttggactcgataaggaagtgagatacgcctatagaggtggttttacatggttaa atgataggttcaaagaaaaagaaatcggagaaggcatggtcttcgatgttaatagtctatatcctgcaca gatgtatagtcgtctccttccatacggtgaacctatagtattcgagggtaaatacgtttgggacgaagat tacccactacacatacagcatatcagatgtgagttcgaattgaaagagggctatatacccactatacaga taaaaagaagtaggttttataaaggtaatgagtacctaaaaagtagcggcggggagatagccgacctctg gttgtcaaatgtagacctagaattaatgaaagaacactacgatttatataacgttgaatatatcagcggc ttaaaatttaaagcaactacaggtttgtttaaagattttatagataaatggacgtacatcaagacgacat cagaaggagcgatcaagcaactagcaaaactgatgttaaacagtctatacggtaaattcgctagtaaccc tgatgttacagggaaagtcccttatttaaaagagaatggggcgctaggtttcagacttggagaagaggaa acaaaagaccctgtttatacacctatgggcgttttcatcactgcatgggctagatacacgacaattacag cggcacaggcttgttatgatcggataatatactgtgatactgacagcatacatttaacgggtacagagat acctgatgtaataaaagatatagttgaccctaagaaatttgggatactgggcacatgaaagtacattcaa agagctaaatatctgagacagaagacctatatcaagacatctatatgaaagaagtagatggtaagttagt agaaggtagtccagatgattacactgatataaaatttagtgttaaatgtgcgggaatgactgacaagatt aagaaagaggttacgtttgagaatttcaaagtcggattcagtcggaaaatgaagcctaagcctgtgcaa gtgccgggcggggtggttctggttgatgacacattcacaatcaaataa |
| 16 | E375H-N62D nucleotide sequence | atgaagcacatgccgagaaagatgtatagttgtgactttgagacaactactaaagtggaagactgtaggg tatgggcgtatggttatatgaatatagaagatcacagtgagtacaaaataggtaatagcctggatgagtt tatggcgtgggtgttgaaggtacaagctgatctatatttccatgatctcaaatttgacggagcttttatc attaactggttggaacgtaatggttttaagtggtcggctgacggattgccaaacacatataatacgatca tatctcgcatgggacaatggtacatgattgatatatgtttaggctacaaagggaaacgtaagatacatac |

TABLE 3-continued

Sequences.

| SEQ ID NO: | Notes | Sequence |
|---|---|---|
| | | agtgatatatgacagcttaaagaaactaccgtttcctgttaagaagatagctaaagactttaaactaact gttcttaaaggtgatattgattaccacaaagaaagaccagtcggctataagataacacccgaagaatacg cctatattaaaaacgatattcagattattgcggaagctctgttaattcagtttaagcaaggtttagaccg gatgacagcaggcagtgacagtctaaaaggtttcaaggatattataaccactaagaaattcaaaaaggtg tttcctacattgagtcttggactcgataaggaagtgagatacgcctatagaggtggttttacatggttaa atgataggttcaaagaaaaagaaatcggagaaggcatggtcttcgatgttaatagtctatatcctgcaca gatgtatagtcgtctccttccatacggtgaacctatagtattcgagggtaaatacgtttgggacgaagat tacccactacacatacagcatatcagatgtgagttcgaattgaaagagggctatatacccactatacaga taaaaagaagtaggttttataaaggtaatgagtacctaaaaagtagcggcggggagatagccgacctctg gttgtcaaatgtagacctagaattaatgaaagaacactacgatttatataacgttgaatatatcagcggc ttaaaatttaaagcaactacaggtttgtttaaagatatttatagataaatggacgtacatcaagacgacat cacacggagcgatcaagcaactagcaaaactgatgttaaacagtctatacggtaaattcgctagtaaccc tgatgttacagggaaagtcccttatttaaaagagaatggggcgctaggtttcagacttggagaagaggaa acaaaagaccctgtttatacacctatgggcgttttcatcactgcatgggctagatacacgacaattacag cggcacaggcttgttatgatcggataatatactgtgatactgacagcatacatttaacgggtacagagat acctgatgtaataaaagatatagttgaccctaagaaattgggatactgggcacatgaaagtacattcaaa agagctaaatatctgagacagaagacctatatacaagacatctatatgaaagaagtagatggtaagttag tagaaggtagtccagatgattacactgatataaaatttagtgttaaatgtgcgggaatgactgacaagat taagaaagaggttacgtttgagaatttcaaagtcggattcagtcggaaaatgaagcctaagcctgtgcaa gtgccgggcggggtggttctggttgatgacacattcacaatcaaataa |
| 17 | E375S-N62D nucleotide sequence | atgaagcacatgccgagaaagatgtatagttgtgactttgagacaactactaaagtggaagactgtaggg tatgggcgtatggttatatgaatatagaagatcacagtgagtacaaaataggtaatagcctggatgagtt tatggcgtgggtgttgaaggtacaagctgatctatatttccatgatctcaaatttgacggagcttttatc attaactggttggaacgtaatggttttaagtggtcggctgacggattgccaaacacatataatacgatca tatctcgcatgggacaatggtacatgattgatatatgtttaggctacaaagggaaacgtaagatacatac agtgatatatgacagcttaaagaaactaccgtttcctgttaagaagatagctaaagactttaaactaact gttcttaaaggtgatattgattaccacaaagaaagaccagtcggctataagataacacccgaagaatacg cctatattaaaaacgatattcagattattgcggaagctctgttaattcagtttaagcaaggtttagaccg gatgacagcaggcagtgacagtctaaaaggtttcaaggatattataaccactaagaaattcaaaaaggtg tttcctacattgagtcttggactcgataaggaagtgagatacgcctatagaggtggttttacatggttaa atgataggttcaaagaaaaagaaatcggagaaggcatggtcttcgatgttaatagtctatatcctgcaca gatgtatagtcgtctccttccatacggtgaacctatagtattcgagggtaaatacgtttgggacgaagat tacccactacacatacagcatatcagatgtgagttcgaattgaaagagggctatatacccactatacaga taaaaagaagtaggttttataaaggtaatgagtacctaaaaagtagcggcggggagatagccgacctctg gttgtcaaatgtagacctagaattaatgaaagaacactacgatttatataacgttgaatatatcagcggc ttaaaatttaaagcaactacaggtttgtttaaagatttatagataaatggacgtacatcaagacgacat caagcggagcgatcaagcaactagcaaaactgatgttaaacagtctatacggtaaattcgctagtaaccc tgatgttacagggaaagtcccttatttaaaagagaatggggcgctaggtttcagacttggagaagaggaa acaaaagaccctgtttatacacctatgggcgttttcatcactgcatgggctagatacacgacaattacag cggcacaggcttgttatgatcggataatatactgtgatactgacagcatacatttaacgggtacagagat acctgatgtaataaaagatatagttgaccctaagaaattgggatactgggcacatgaaagtacattcaaa agagctaaatatctgagacagaagacctatatacaagacatctatatgaaagaagtagatggtaagttag tagaaggtagtccagatgattacactgatataaaatttagtgttaaatgtgcgggaatgactgacaagat taagaaagaggttacgtttgagaatttcaaagtcggattcagtcggaaaatgaagcctaagcctgtgcaa gtgccgggcggggtggttctggttgatgacacattcacaatcaaataa |
| 18 | L384R-N62D nucleotide sequence | atgaagcacatgccgagaaagatgtatagttgtgactttgagacaactactaaagtggaagactgtaggg tatgggcgtatggttatatgaatatagaagatcacagtgagtacaaaataggtaatagcctggatgagtt tatggcgtgggtgttgaaggtacaagctgatctatatttccatgatctcaaatttgacggagcttttatc attaactggttggaacgtaatggttttaagtggtcggctgacggattgccaaacacatataatacgatca tatctcgcatgggacaatggtacatgattgatatatgtttaggctacaaagggaaacgtaagatacatac agtgatatatgacagcttaaagaaactaccgtttcctgttaagaagatagctaaagactttaaactaact gttcttaaaggtgatattgattaccacaaagaaagaccagtcggctataagataacacccgaagaatacg cctatattaaaaacgatattcagattattgcggaagctctgttaattcagtttaagcaaggtttagaccg gatgacagcaggcagtgacagtctaaaaggtttcaaggatattataaccactaagaaattcaaaaaggtg tttcctacattgagtcttggactcgataaggaagtgagatacgcctatagaggtggttttacatggttaa atgataggttcaaagaaaaagaaatcggagaaggcatggtcttcgatgttaatagtctatatcctgcaca gatgtatagtcgtctccttccatacggtgaacctatagtattcgagggtaaatacgtttgggacgaagat tacccactacacatacagcatatcagatgtgagttcgaattgaaagagggctatatacccactatacaga taaaaagaagtaggttttataaaggtaatgagtacctaaaaagtagcggcggggagatagccgacctctg gttgtcaaatgtagacctagaattaatgaaagaacactacgatttatataacgttgaatatatcagcggc ttaaaatttaaagcaactacaggtttgtttaaagatttatagataaatggacgtacatcaagacgacat cagaaggagcgatcaagcaactagcaaaacggatgttaaacagtctatacggtaaattcgctagtaaccc tgatgttacagggaaagtcccttatttaaaagagaatggggcgctaggtttcagacttggagaagaggaa acaaaagaccctgtttatacacctatgggcgttttcatcactgcatgggctagatacacgacaattacag cggcacaggcttgttatgatcggataatatactgtgatactgacagcatacatttaacgggtacagagat acctgatgtaataaaagatatagttgaccctaagaaattgggatactgggcacatgaaagtacattcaaa agagctaaatatctgagacagaagacctatatacaagacatctatatgaaagaagtagatggtaagttag tagaaggtagtccagatgattacactgatataaaatttagtgttaaatgtgcgggaatgactgacaagat taagaaagaggttacgtttgagaatttcaaagtcggattcagtcggaaaatgaagcctaagcctgtgcaa gtgccgggcggggtggttctggttgatgacacattcacaatcaaataa |

TABLE 3-continued

Sequences.

| SEQ ID NO: | Notes | Sequence |
|---|---|---|
| 19 | E486A-N62D nucleotide sequence | atgaagcacatgccgagaaagatgtatagttgtgactttgagacaactactaaagtggaagactgtaggg<br>tatgggcgtatggttatatgaatatagaagatcacagtgagtacaaaataggtaatagcctggatgagtt<br>tatggcgtgggtgttgaaggtacaagctgatctatatttccatgatctcaaatttgacggagcttttatc<br>attaactggttggaacgtaatggttttaagtggtcggctgacggattgccaaacacatataatacgatca<br>tatctcgcatgggacaatggtacatgattgatatatgtttaggctacaaagggaaacgtaagatacatac<br>agtgatatatgacagcttaaagaaactaccgtttcctgttaagaagatagctaaagactttaaactaact<br>gttcttaaaggtgatattgattaccacaaagaaagaccagtcggctataagataacacccgaagaatacg<br>cctatattaaaaacgatattcagattattgcggaagctctgttaattcagtttaagcaaggtttagaccg<br>gatgacagcaggcagtgacagtctaaaaggtttcaaggatattataaccactaagaaattcaaaaaggtg<br>tttcctacattgagtcttggactcgataaggaagtgagatacgcctatagaggtggttttacatggttaa<br>atgataggttcaaagaaaaagaaatcggagaaggcatggtcttcgatgttaatagtctatatcctgcaca<br>gatgtatagtcgtctccttccatacggtgaacctatagtattcgagggtaaatacgtttgggacgaagat<br>tacccactacacatacagcatatcagatgtgagttcgaattgaaagagggctatatacccactatacaga<br>taaaaagaagtaggttttataaaggtaatgagtacctaaaaagtagcggcggggagatagccgacctctg<br>gttgtcaaatgtagacctagaattaatgaaagaacactacgatttatataacgttgaatatatcagcggc<br>ttaaaatttaaagcaactacaggtttgtttaaagattttatagataaatggacgtacatcaagacgacat<br>cagaaggagcgatcaagcaactagcaaaactgatgttaaacagtctatacggtaaattcgctagtaaccc<br>tgatgttacagggaaagtcccttatttaaaagagaatggggcgctaggtttcagacttggagaagaggaa<br>acaaaagaccctgtttatacacctatgggcgttttcatcactgcatgggctagatacacgacaattacag<br>cggcacaggcttgttatgatcggataatatactgtgatactgacagcatacatttaacgggtacagagat<br>acctgatgtaataaaagatatagttgaccctaagaaatgggatactgggcacatgccagtacattcaaa<br>agagctaaatatctgagacagaagacctatatacaagacatctatatgaaagaagtagatggtaagttag<br>tagaaggtagtccagatgattacactgatataaaatttagtgttaaatgtgcgggaatgactgacaagat<br>taagaaagagggttacgtttgagaatttcaaagtcggattcagtcggaaaatgaagcctaagcctgtgcaa<br>gtgccgggcggggtggttctggttgatgacacattcacaatcaaataa |
| 20 | E486D-N62D nucleotide sequence | atgaagcacatgccgagaaagatgtatagttgtgactttgagacaactactaaagtggaagactgtaggg<br>tatgggcgtatggttatatgaatatagaagatcacagtgagtacaaaataggtaatagcctggatgagtt<br>tatggcgtgggtgttgaaggtacaagctgatctatatttccatgatctcaaatttgacggagcttttatc<br>attaactggttggaacgtaatggttttaagtggtcggctgacggattgccaaacacatataatacgatca<br>tatctcgcatgggacaatggtacatgattgatatatgtttaggctacaaagggaaacgtaagatacatac<br>agtgatatatgacagcttaaagaaactaccgtttcctgttaagaagatagctaaagactttaaactaact<br>gttcttaaaggtgatattgattaccacaaagaaagaccagtcggctataagataacacccgaagaatacg<br>cctatattaaaaacgatattcagattattgcggaagctctgttaattcagtttaagcaaggtttagaccg<br>gatgacagcaggcagtgacagtctaaaaggtttcaaggatattataaccactaagaaattcaaaaaggtg<br>tttcctacattgagtcttggactcgataaggaagtgagatacgcctatagaggtggttttacatggttaa<br>atgataggttcaaagaaaaagaaatcggagaaggcatggtcttcgatgttaatagtctatatcctgcaca<br>gatgtatagtcgtctccttccatacggtgaacctatagtattcgagggtaaatacgtttgggacgaagat<br>tacccactacacatacagcatatcagatgtgagttcgaattgaaagagggctatatacccactatacaga<br>taaaaagaagtaggttttataaaggtaatgagtacctaaaaagtagcggcggggagatagccgacctctg<br>gttgtcaaatgtagacctagaattaatgaaagaacactacgatttatataacgttgaatatatcagcggc<br>ttaaaatttaaagcaactacaggtttgtttaaagattttatagataaatggacgtacatcaagacgacat<br>cagaaggagcgatcaagcaactagcaaaactgatgttaaacagtctatacggtaaattcgctagtaaccc<br>tgatgttacagggaaagtcccttatttaaaagagaatggggcgctaggtttcagacttggagaagaggaa<br>acaaaagaccctgtttatacacctatgggcgttttcatcactgcatgggctagatacacgacaattacag<br>cggcacaggcttgttatgatcggataatatactgtgatactgacagcatacatttaacgggtacagagat<br>acctgatgtaataaaagatatagttgaccctaagaaatgggatactgggcacatgacagtacattcaaa<br>agagctaaatatctgagacagaagacctatatacaagacatctatatgaaagaagtagatggtaagttag<br>tagaaggtagtccagatgattacactgatataaaatttagtgttaaatgtgcgggaatgactgacaagat<br>taagaaagagggttacgtttgagaatttcaaagtcggattcagtcggaaaatgaagcctaagcctgtgcaa<br>gtgccgggcggggtggttctggttgatgacacattcacaatcaaataa |
| 21 | K512A-N62D nucleotide sequence | atgaagcacatgccgagaaagatgtatagttgtgactttgagacaactactaaagtggaagactgtaggg<br>tatgggcgtatggttatatgaatatagaagatcacagtgagtacaaaataggtaatagcctggatgagtt<br>tatggcgtgggtgttgaaggtacaagctgatctatatttccatgatctcaaatttgacggagcttttatc<br>attaactggttggaacgtaatggttttaagtggtcggctgacggattgccaaacacatataatacgatca<br>tatctcgcatgggacaatggtacatgattgatatatgtttaggctacaaagggaaacgtaagatacatac<br>agtgatatatgacagcttaaagaaactaccgtttcctgttaagaagatagctaaagactttaaactaact<br>gttcttaaaggtgatattgattaccacaaagaaagaccagtcggctataagataacacccgaagaatacg<br>cctatattaaaaacgatattcagattattgcggaagctctgttaattcagtttaagcaaggtttagaccg<br>gatgacagcaggcagtgacagtctaaaaggtttcaaggatattataaccactaagaaattcaaaaaggtg<br>tttcctacattgagtcttggactcgataaggaagtgagatacgcctatagaggtggttttacatggttaa<br>atgataggttcaaagaaaaagaaatcggagaaggcatggtcttcgatgttaatagtctatatcctgcaca<br>gatgtatagtcgtctccttccatacggtgaacctatagtattcgagggtaaatacgtttgggacgaagat<br>tacccactacacatacagcatatcagatgtgagttcgaattgaaagagggctatatacccactatacaga<br>taaaaagaagtaggttttataaaggtaatgagtacctaaaaagtagcggcggggagatagccgacctctg<br>gttgtcaaatgtagacctagaattaatgaaagaacactacgatttatataacgttgaatatatcagcggc<br>ttaaaatttaaagcaactacaggtttgtttaaagattttatagataaatggacgtacatcaagacgacat<br>cagaaggagcgatcaagcaactagcaaaactgatgttaaacagtctatacggtaaattcgctagtaaccc<br>tgatgttacagggaaagtcccttatttaaaagagaatggggcgctaggtttcagacttggagaagaggaa<br>acaaaagaccctgtttatacacctatgggcgttttcatcactgcatgggctagatacacgacaattacag<br>cggcacaggcttgttatgatcggataatatactgtgatactgacagcatacatttaacgggtacagagat<br>acctgatgtaataaaagatatagttgaccctaagaaatgggatactgggcacatgaagtacattcaaa<br>agagctaaatatctgagacagaagacctatatacaagacatctatatgaaagaagtagatggtgccttag |

TABLE 3-continued

Sequences.

| SEQ ID NO: | Notes | Sequence |
|---|---|---|
| | | tagaaggtagtccagatgattacactgatataaaatttagtgtttaaatgtgcgggaatgactgacaagat<br>taagaaagaggttacgtttgagaatttcaaagtcggattcagtcggaaaatgaagcctaagcctgtgcaa<br>gtgccgggcggggtggttctggttgatgacacattcacaatcaaataa |
| 22 | NipTuck_1-<br>N62D<br>nucleotide<br>sequence | atgaagcacatgccgagaaagatgtatagttgtgactttgagcaactactaaagtggaagactgtaggg<br>tatgggcgtatggttatatgaatatagaagatcacagtgagtacaaaataggtaatagcctggatgagtt<br>tatggcgtgggtgtttgaaggtacaagctgatctatatttccatgatctcaaatttgacggagcttttatc<br>attaactggttggaacgtaatggttttaagtggtcggctgacggattgccaaacacatataatacgatca<br>tatctcgcatgggacaatggtacatgattgatatatgtttaggctacaaagggaaacgtaagatacatac<br>agtgatatatgacagcttaaagaaactaccgtttcctgttaagaagatagctaaagactttaaactaact<br>gttcttaaaggtgatattgattaccacaaagaaagaccagtcggctataagataacacccgaagaatacg<br>cctatattaaaaacgatattcagattattgcggaagctctgttaattcagtttaagcaaggtttagaccg<br>gatgacagcaggcagtgacagtctaaaaggtttcaaggatattataaccactaagaaattcaaaaaggtg<br>tttcctacattgagtcttggactcgataaggaagtgagatacgcctatagaggtggttttacatggttaa<br>atgataggttcaaagaaaaagaaatcggagaaggcatggtcttcgatgttaatagtctatatcctgcaca<br>gatgtatagtcgtctccttccatacggtgaacctatagtattcgagggtaaatacgtttgggacgaagat<br>tacccactacacatacagcatatcagatgtgagttcgaattgaaagagggctatatacccactatacaga<br>taaaaagaagtaggttttataaaggtaatgagtacctaaaaagtagcggcggggagatagccgacctctg<br>gttgtcaaatgtagacctagaattaatgaaagaactacgattttatataacgttaatatatcagcggc<br>ttaaaatttaaagcaactacaggtttgtttaaagattttatagataaatggacgtacatcaagacgacat<br>cagaaggagcgatcaagcaactagcaaaactgatgttaaacagtctatacggtaaattcgctagtaaccc<br>tgatgttacagggaaagtccctatttaaaagagaatggggcgctaggtttcagacttggagaagaggaa<br>acaaaagaccctgtttatacacctatgggcgtttttcatcactgcatgggctagatacagacaattacag<br>cggcacaggcttgttatgatcggataatactgtgatactgacagcatacattttaacgggtacagagat<br>acctgatgtaataaaaagatatagttgaccctaagaaatttgggatactgggcacatgaaagtacattcaaa<br>agagctaaatatctgagacagaagacctatatacaagacatcaaggatggagagtttagtgtttaaatgtg<br>cgggaatgactgacaagattaagaaagaggttacgtttgagaatttcaaagtcggattcagtcggaaaat<br>gaagcctaagcctgtgcaagtgccgggcggggtggttctggttgatgacacattcacaatcaaataa |
| 23 | NipTuck_2-<br>N62D<br>nucleotide<br>sequence | atgaagcacatgccgagaaagatgtatagttgtgactttgagcaactactaaagtggaagactgtaggg<br>tatgggcgtatggttatatgaatatagaagatcacagtgagtacaaaataggtaatagcctggatgagtt<br>tatggcgtgggtgtttgaaggtacaagctgatctatatttccatgatctcaaatttgacggagcttttatc<br>attaactggttggaacgtaatggttttaagtggtcggctgacggattgccaaacacatataatacgatca<br>tatctcgcatgggacaatggtacatgattgatatatgtttaggctacaaagggaaacgtaagatacatac<br>agtgatatatgacagcttaaagaaactaccgtttcctgttaagaagatagctaaagactttaaactaact<br>gttcttaaaggtgatattgattaccacaaagaaagaccagtcggctataagataacacccgaagaatacg<br>cctatattaaaaacgatattcagattattgcggaagctctgttaattcagtttaagcaaggtttagaccg<br>gatgacagcaggcagtgacagtctaaaaggtttcaaggatattataaccactaagaaattcaaaaaggtg<br>tttcctacattgagtcttggactcgataaggaagtgagatacgcctatagaggtggttttacatggttaa<br>atgataggttcaaagaaaaagaaatcggagaaggcatggtcttcgatgttaatagtctatatcctgcaca<br>gatgtatagtcgtctccttccatacggtgaacctatagtattcgagggtaaatacgtttgggacgaagat<br>tacccactacacatacagcatatcagatgtgagttcgaattgaaagagggctatatacccactatacaga<br>taaaaagaagtaggttttataaaggtaatgagtacctaaaaagtagcggcggggagatagccgacctctg<br>gttgtcaaatgtagacctagaattaatgaaagaactacgattttatataacgttaatatatcagcggc<br>ttaaaatttaaagcaactacaggtttgtttaaagattttatagataaatggacgtacatcaagacgacat<br>cagaaggagcgatcaagcaactagcaaaactgatgttaaacagtctatacggtaaattcgctagtaaccc<br>tgatgttacagggaaagtccctatttaaaagagaatggggcgctaggtttcagacttggagaagaggaa<br>acaaaagaccctgtttatacacctatgggcgtttttcatcactgcatgggctagatacagacaattacag<br>cggcacaggcttgttatgatcggataatactgtgatactgacagcatacattttaacgggtacagagat<br>acctgatgtaataaaaagatatagttgaccctaagaaatttgggatactgggcacatgaaagtacattcaaa<br>agagctaaatatctgagacagaagacctatatacaagacatcgacggctttagtgtttaaatgtgcgggaa<br>tgactgacaagattaagaaagaggttacgtttgagaatttcaaagtcggattcagtcggaaaatgaagcc<br>taagcctgtgcaagtgccgggcggggtggttctggttgatgacacattcacaatcaaataa |
| 24 | K135A-<br>N62D amino<br>acid<br>sequence | mkhmprkmys cdfetttkve dcrvwaygym niedhseyki gnsldefmaw<br>vlkvqadlyf hdlkfdgafi inwlerngfk wsadglpnty ntiisrmgqw<br>ymidiclgyk gkrkihtviy dslkklpfpv kkiaadfklt vlkgdidyhk<br>erpvgykitp eeyayikndi qiiaealliq fkqgldrmta gsdslkgfkd<br>iittkkfkkv fptlslgldk evryayrggf twlndrfkek eigegmvfdv<br>nslypaqmys rllpygepiv fegkyvded yplhiqhirc efelkegyip<br>tiqikrsrfy kgneylkssg geiadlwlsn vdlelmkehy dlynveyisg<br>lkfkattglf kdfidkwtyi kttsegaikq laklmlnsly gkfasnpdvt<br>gkvpylkeng algfrlgeee tkdpvytpmg vfitawaryt titaaqacyd<br>riiycdtdsi hltgteipdv ikdivdpkkl gywahestfk rakylrqkty<br>iqdiymkevd gklvegspdd ytdikfsvkc agmtdkikke vtfenfkvgf<br>srkmkpkpvq vpggvvlvdd tftik |
| 25 | E375H-<br>N62D amino<br>acid<br>sequence | mkhmprkmys cdfetttkve dcrvwaygym niedhseyki gnsldefmaw<br>vlkvqadlyf hdlkfdgafi inwlerngfk wsadglpnty ntiisrmgqw<br>ymidiclgyk gkrkihtviy dslkklpfpv kkiakdfklt vlkgdidyhk<br>erpvgykitp eeyayikndi qiiaealliq fkqgldrmta gsdslkgfkd<br>iittkkfkkv fptlslgldk evryayrggf twlndrfkek eigegmvfdv<br>nslypaqmys rllpygepiv fegkyvded yplhiqhirc efelkegyip<br>tiqikrsrfy kgneylkssg geiadlwlsn vdlelmkehy dlynveyisg |

TABLE 3-continued

Sequences.

| SEQ ID NO: | Notes | Sequence |
|---|---|---|
| | | lkfkattglf kdfidkwtyi kttshgaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdiymkevd gklvegspdd ytdikfsvkc agmtdkikke vtfenfkvgf srkmkpkpvq vpggvvlvdd tftik |
| 26 | E375S-N62D amino acid sequence | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttssgaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdiymkevd gklvegspdd ytdikfsvkc agmtdkikke vtfenfkvgf srkmkpkpvq vpggvvlvdd tftik |
| 27 | E375K-N62D amino acid sequence | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttskgaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdiymkevd gklvegspdd ytdikfsvkc agmtdkikke vtfenfkvgf srkmkpkpvq vpggvvlvdd tftik |
| 28 | E375R-N62D amino acid sequence | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttsrgaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdiymkevd gklvegspdd ytdikfsvkc agmtdkikke vtfenfkvgf srkmkpkpvq vpggvvlvdd tftik |
| 29 | L384R-N62D amino acid sequence | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttsegaikq lakrmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdiymkevd gklvegspdd ytdikfsvkc agmtdkikke vtfenfkvgf srkmkpkpvq vpggvvlvdd tftik |
| 30 | E486A-N62D amino acid sequence | mkhmprkmys cdfetttkve dcrvwaygym niedhseyki gnsldefmaw vlkvqadlyf hdlkfdgafi inwlerngfk wsadglpnty ntiisr TABLE 3-continued Sequences.

| SEQ ID NO: | Notes | Sequence |
|---|---|---|
| 31 | E486D-N62D amino acid sequence | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttsegaikq laklmlnsly gkfasnpdvt gkvpylkeng algfrlgeee tkdpvytpmg vfitawaryt titaaqacyd riiycdtdsi hltgteipdv ikdivdpkkl gywahdstfk rakylrqkty iqdiymkevd gklvegspdd ytdikfsvkc agmtdkikke vtfenfkvgf srkmkpkpvq vpggvvlvdd tftik |
| 32 | K512A-N62D amino acid sequence | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttsegaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdiymkevd galvegspdd ytdikfsvkc agmtdkikke vtfenfkvgf srkmkpkpvq vpggvvlvdd tftik |
| 33 | NipTuck_1-N62D amino acid sequence (deletion of residues 505-525) | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttsegaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdikdgefs vkcagmtdki kkevtfenfk vgfsrkmkpk pvqvpggvvl vddtftik |
| 34 | NipTuck_2-N62D amino acid sequence (deletion of residues 505-525) | mkhmprkmys cdfetttkve dcrvwaygym niedhseyki gnsldefmaw vlkvqadlyf hdlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd iittkkfkkv fptlslgldk evryayrggf twlndrfkek eigegmvfdv nslypaqmys rllpygepiv fegkyvwded yplhiqhirc efelkegyip tiqikrsrfy kgneylkssg geiadlwlsn vdlelmkehy dlynveyisg lkfkattglf kdfidkwtyi kttsegaikq laklmlnsly gkfasnpdvt gkvpylkeng algfrlgeee tkdpvytpmg vfitawaryt titaaqacyd riiycdtdsi hltgteipdv ikdivdpkkl gywahestfk rakylrqkty iqdidgfsvk cagmtdkikk evtfenfkvg fsrkmkpkpv qvpggvvlvd dtftik |

Characterization of Recombinant Polymerases with Nucleotide Analogues $K_m$ and $V_{max}$ were determined for exemplary recombinant Phi29 polymerases and various nucleotide analogues. Results are presented in Table 4.

TABLE 4

$K_m$ and $V_{max}$ versus analogues.

| Mutation | Km[1] | Vmax[1] | Km[2] | Vmax[2] | Km[3] | Vmax[3] | Km[4] | Vmax[4] |
|---|---|---|---|---|---|---|---|---|
| N62D | 23 | 610 | 20 | 540 | 838 | 2500 | 68 | 1620 |
| N62D: E375H | 17 | 800 | 15 | 526 | 433 | 1250 | | |
| N62D: E375S | 16.5 | 1158 | | | | | 40 | 1981 |
| N62D: E375K | 12 | 595 | | | | | | |
| N62D: E375Y | 2.5 | 773 | 6.6 | 471 | 440 | 1430 | 18 | 1292 |
| N62D: E375W | 1.8 | 889 | 5.0 | 595 | 248 | 1428 | 16 | 1585 |

[1]Measured for Alexa633-O-dC4P (also referred to as A633dC4P herein)
[2]Measured for Alexa555-C2-dT4P. This analogue has a 2-carbon linker ("C2") between the delta phosphate and the label moiety and has the following structure:

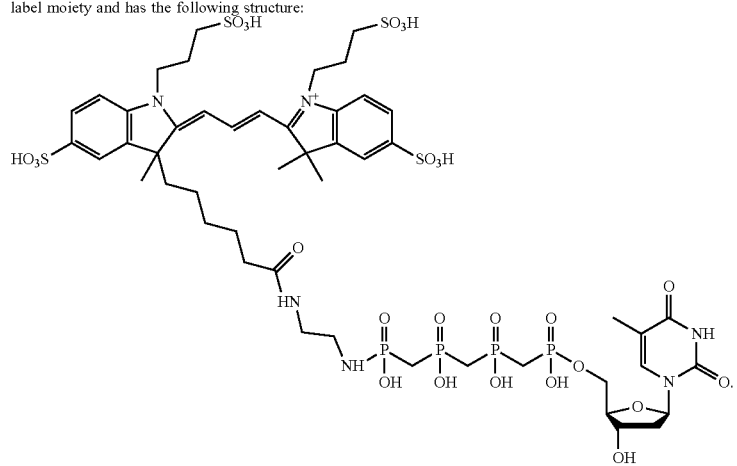

[3]Measured for Alexa555-C2-dTTP
[4]Measured for Alexa532-O-dG4P

A set of exemplary recombinant Phi29 polymerases were characterized with various nucleotides and/or nucleotide analogues. Results are presented in Table 5.

TABLE 5

Screening data.

| Mutation | Ratio (Low/High)[1] | Rate High[2] | Hz Rate[3] | Mutation 2[4] | Tag(s)[5] |
|---|---|---|---|---|---|
| E375W | 0.677 | 699.4 | 19.1 | N62D | His |
| E375Y | 0.694 | 498.5 | 12.1 | N62D | His |
| E375H | 0.445 | 510.1 | 9.4 | N62D | His |
| E375Q | 0.356 | 531.6 | 6.3 | N62D | His |
| E375K | 0.425 | 516.1 | 6.2 | N62D | His |
| E375S | 0.335 | 528.4 | 5.9 | N62D | His |
| E375A | 0.383 | 465.9 | 5.8 | N62D | His |
| T15I | 0.355 | 416.5 | 3.0 | | His |
| N62D | 0.355 | 349.3 | 2.8 | | GST-His |
| N62D | 0.362 | 373.2 | 2.7 | | His |
| K135A | 0.412 | 272.0 | 1.6 | N62D | His |
| K512A | 0.335 | 347.7 | 1.4 | N62D | His |
| NipTuck1 | 0.508 | 192.4 | 1.3 | N62D | His |
| D12A | 0.888 | 55.3 | 1.2 | | GST-His |
| E486A | 0.441 | 152.5 | 1.0 | N62D | His |
| E486D | 0.467 | 142.0 | 0.9 | N62D | His |
| T15I | 0.726 | 105.9 | 0.0 | N62D | His |
| NipTuck2 | 0.635 | 156.3 | 0.0 | N62D | His |
| L384R | 0.768 | 79.6 | −0 | N62D | His |

Figure 7A:
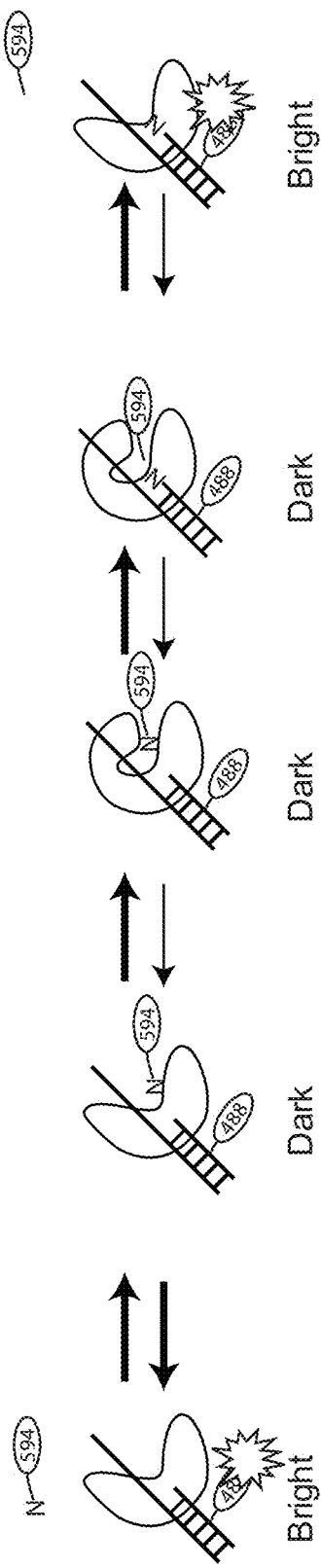
FIG. 7A schematically illustrates a FRET stopped flow assay used to determine rates of binding and product release. Results of the assay are shown in FIGS. 7B-7D, for Phi29 N62D (FIG. 7B), N62D:E375Y (FIG. 7C), and N62D: E375W (FIG. 7D).
Figure 7B:
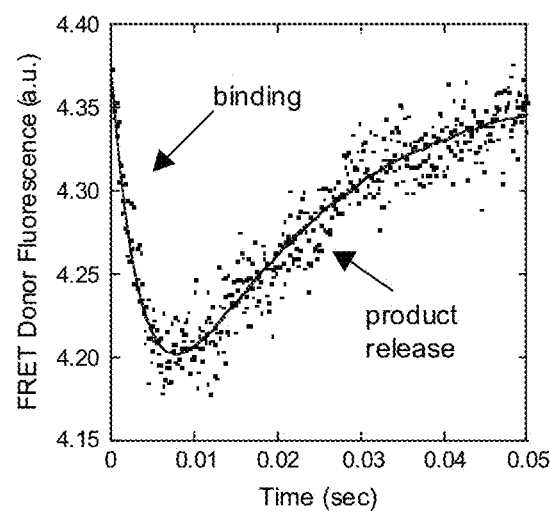
Figure 7C:
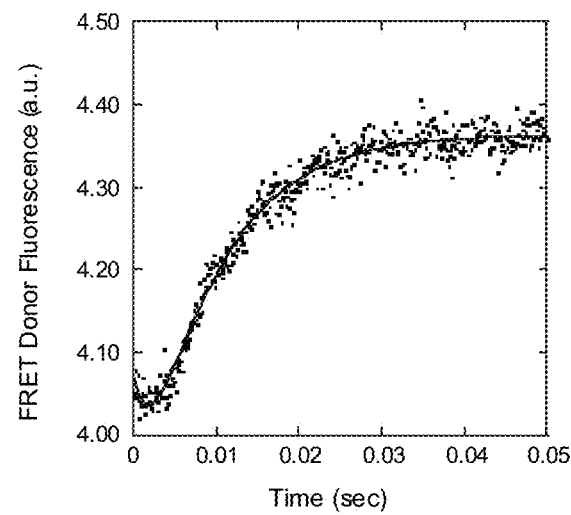
Figure 7D:
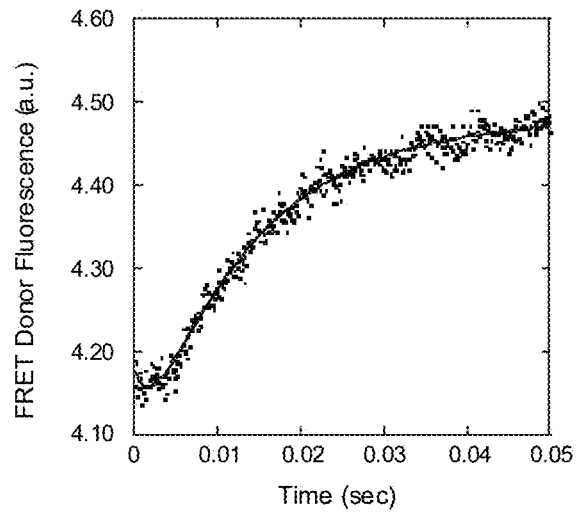

[1]Ratio = (rate at 5 μM A633dC4P with 20 μM dA, dG, dTTP)/(rate at 25 μM A633dC4P with 20 μM dA, dG, dTTP) at 1 mM MnCl₂. A higher ratio corresponds to a lower Km.
[2]Rate at 25 μM A633dC4P with 20 μM dA, dG, dTTP
[3]Rate at 10 μM Alexa488-O-dA4P, 10 μM FAM-Alexa532-O-dG4P, 10 μM FAM-Alexa594-O-dT4P, 10 μM Alexa633-O-dC4P with 1 mM MnCl₂. Provides a measure of both Km and Vmax, with a representative set of four nucleotide analogues.
[4]Background mutation (if any). The recombinant polymerase corresponds to wild type Phi29 polymerase plus mutation 1 plus mutation 2.
[5]Tag for immobilization and or purification Rates of binding and product release were determined for exemplary recombinant Phi29 polymerases with nucleotide analogue A594-dT4P using a FRET stopped flow assay as schematically illustrated in FIG. 7A. Results are depicted graphically in FIGS. 7B-D for Phi29 N62D (FIG. 7B), N62D:E375Y (FIG. 7C), and N62D:E375W (FIG. 7D). Product release rates are shown in Table 6.

The E375Y and E375W mutant polymerases demonstrated increased rates of binding and product release, indicating they utilize the analogue better than does the parent enzyme.

TABLE 6

Product release rate

| Enzyme | Product Release Rate |
|---|---|
| N62D | 55 s$^{-1}$ |
| N62D:E375Y | 117 s$^{-1}$ |
| N62D:E375W | 76 s$^{-1}$ |

Figure 8A:
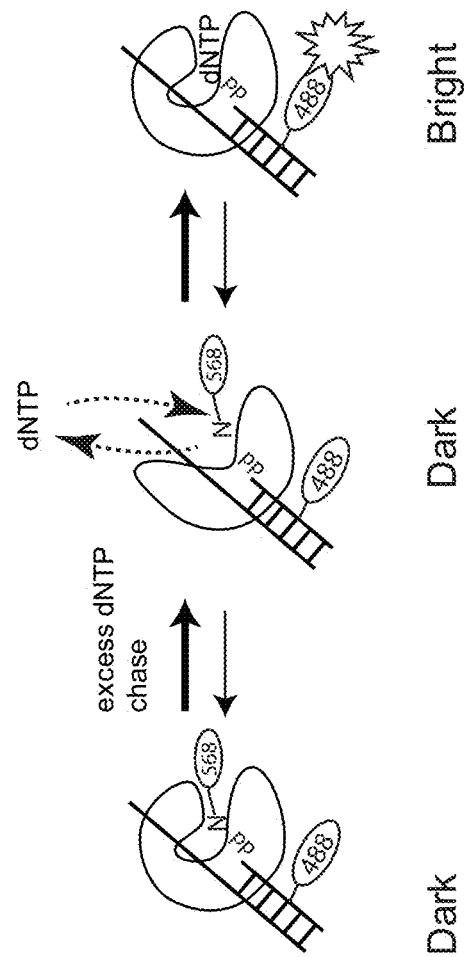
FIG. 8A schematically illustrates a FRET stopped flow assay used to determine branching rate. Results of the assay are shown in FIGS. 8B-8D, for Phi29 N62D (FIG. 8B), N62D:E375Y (FIG. 8C), and N62D:E375W (FIG. 8D).

Relative branching rate (dissociation of the analogue without incorporation, i.e., substrate dissociation) was also determined for exemplary recombinant Phi29 polymerases with nucleotide analogue Alexa568-dA4P (also called A568-dA4P), using a FRET stopped flow assay as schematically illustrated in FIG. 8A. In this technique, a template with a FRET donor dye compatible for FRET with the corresponding dye on the nucleotide analogue is employed. The primer has a dideoxy-termination at the 3' end to prevent incorporation. The analogue is pre-mixed with the enzyme-template-dideoxy primer complex. In the stopped flow apparatus, this preformed complex is rapidly mixed with the corresponding native nucleotide (native dATP, in this example) in excess which serves as a "trap" to prevent rebinding of the analogue after it dissociates. The increase in donor dye fluorescence is monitored as a means of monitoring the dissociation/branching rate of the analogue.

Figure 8B:
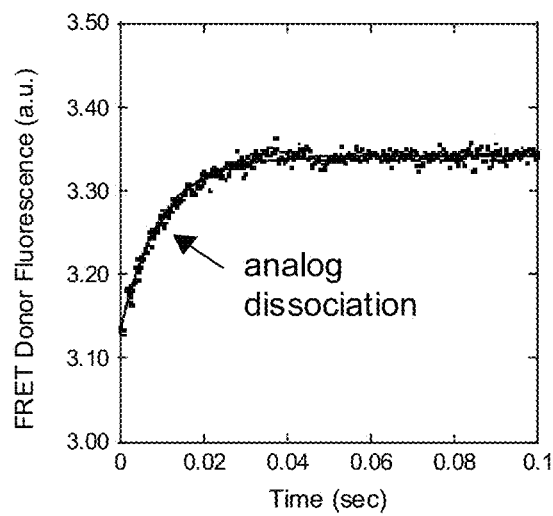
Figure 8C:
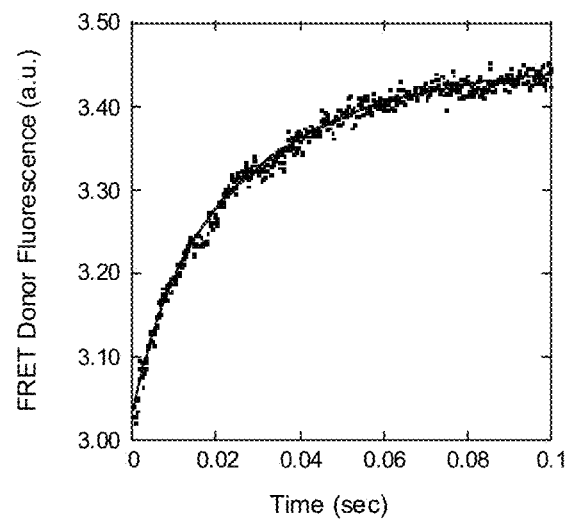
Figure 8D:
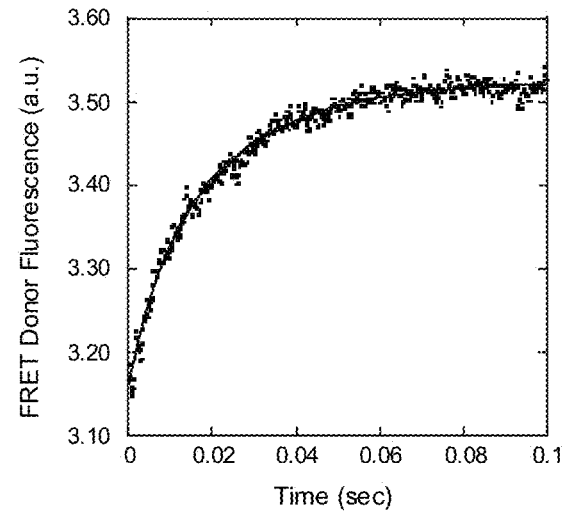

Results are depicted graphically in FIGS. 8B-D for Phi29 N62D (FIG. 8B), N62D:E375Y (FIG. 8C), and N62D:E375W (FIG. 8D). Branching rates are shown in Table 7.

TABLE 7

Branching rate.

| Enzyme | Branching Rate |
|---|---|
| N62D | 90 s$^{-1}$ |
| N62D:E375Y | 31 s$^{-1}$ |
| N62D:E375W | 43 s$^{-1}$ |

Additional Exemplary Recombinant Polymerases

Polymerases of the invention can include a Phi29 polymerase (or homolog thereof) including any of the mutations listed in Table 8, singly or in combination with other mutations (e.g., other mutations described herein). For example, polymerases of the invention optionally include a Phi29 polymerase (or homolog thereof) that includes a combination of mutations as specified in Table 8.

TABLE 8

Exemplary mutations.

D12A E375W T372D
D12A E375W T372E
D12A E375W T372R K478D
D12A E375W T372R K478E
D12A E375W T372K K478D
D12A E375W T372K D478E
D12A E375W K135D
D12A E375W K135E
D12A E375W K512D
D12A E375W K512E
D12A E375W E408K
D12A E375W E408R
D12A E375W T368D L480K
D12A E375W T368E L480K
D12A D456N
N62D D456N
D12A D456A
N62D D456A
D12A D456S
N62D D456S
N62D E375M
N62D E375L
N62D E375I
N62D E375F
N62D E375D
D12A K512W
N62D K512W
D12A K512Y
N62D K512Y
D12A K512F
N62D K512F
D12A E375W K512L
N62D E375W K512L
D12A E375W K512Y
N62D E375W K512Y
D12A E375W K512F
N62D E375W K512F
D12A E375Y K512L
N62D E375Y K512L
D12A E375Y K512Y
N62D E375Y K512Y
D12A E375Y K512F
N62D E375Y K512F
D12A E375W K512H
N62D E375W K512H
D12A E375Y K512H
N62D E375Y K512H
D12A D510F

TABLE 8-continued

Exemplary mutations.

N62D D510F
D12A D510Y
N62D D510Y
D12A D510W
N62D D510W
D12A E375W D510F
N62D E375W D510F
D12A E375W D510Y
N62D E375W D510Y
D12A E375W D510W
N62D E375W D510W
D12A E375W D510W K512L
N62D E375W D510W K512L
D12A E375W D510W K512F
N62D E375W D510W K512F
D12A E375W D510H
N62D E375W D510H
D12A E375W D510H K512H
N62D E375W D510H K512H
D12A E375W D510H K512F
N62D E375W D510H K512F
D12A V509Y
N62D V509Y
D12A V509W
N62D V509W
D12A V509F
N62D V509F
D12A V514Y
N62D V514Y
D12A V514W
N62D V514W
D12A V514F
N62D V514F
D12S
D12N
D12Q
D12K
D12A
N62D Y254F
N62D Y254V
N62D Y254A
N62D Y390F
N62D Y390A
N62D S252A
N62D N387A
N62D K157E
N62D I242H
N62D Y259S
N62D G320C
N62D L328V
N62D T368M
N62D T368G
N62D Y369R
N62D Y369H
N62D Y369E
N62D I370V
N62D I370K
N62D K371Q
N62D T372N
N62D T372D
N62D T372R
N62D T372L
N62D T373A
N62D T373H
N62D S374E
N62D I378K
N62D K379E
N62D K379T
N62D N387D
N62D Y405V
N62D L408D
N62D G413D
N62D D423V
N62D I442V
N62D Y449F
N62D D456V
N62D L480M
N62D V509K

TABLE 8-continued

Exemplary mutations.

N62D V509I
N62D D510A
N62D V514I
N62D V514K
N62D E515K
N62D D523T
N62D H149Y E375W M554S
M8S N62D M102S H116Y M188S E375W
N62D M97S E375W
M8S N62D M97S M102S M188S E375W M554S
M8A N62D M97A M102A M188A E375W M554A

A few mutations in the Phi29 polymerase have been previously described. For the N62D mutation, see de Vega et al. (1996) "Primer-terminus stabilization at the 3'-5' exonuclease active site of phi29 DNA polymerase. Involvement of two amino acid residues highly conserved in proofreading DNA polymerases" EMBO J. 15(5):1182-92. For the D12A mutation and mutations at positions E14, 66, 165, 169, 12 and 66, and 14 and 66, see Esteban et al. (1994) "3'→5' exonuclease active site of phi 29 DNA polymerase. Evidence favoring a metal ion-assisted reaction mechanism" J Biol Chem. 269(50):31946-54. For mutation of S252, see Blasco et al. (1993) "Phi 29 DNA polymerase active site. Residue ASP249 of conserved amino acid motif 'Dx2SLYP' is critical for synthetic activities" J Biol Chem. 268(32): 24106-13. For mutation of Y254, see Blasco et al. (1992) "Phi 29 DNA polymerase active site. Mutants in conserved residues Tyr254 and Tyr390 are affected in dNTP binding" J Biol Chem. 267(27):19427-34. For mutation of K371, see Truniger et al. (2002) "A positively charged residue of phi29 DNA polymerase, highly conserved in DNA polymerases from families A and B, is involved in binding the incoming nucleotide" Nucleic Acids Res. 30(7):1483-92. For mutation of K379, see Truniger et al. (2004) "Two Positively Charged Residues of φ29 DNA Polymerase, Conserved in Protein-primed DNA Polymerases, are Involved in Stabilisation of the Incoming Nucleotide" Journal of Molecular Biology 335(2):481-494. For mutation of N387, see Blasco et al. (1993) "Phi 29 DNA polymerase active site. The conserved amino acid motif 'Kx3NSxYG' is involved in template-primer binding and dNTP selection" J Biol Chem. 268(22): 16763-70. For mutation of Y390, see Blasco et al (1992) "Phi 29 DNA polymerase active site. Mutants in conserved residues Tyr254 and Tyr390 are affected in dNTP binding" J Biol Chem. 267(27):19427-34. For mutation of D456, see Bernad et al. (1990) "The highly conserved amino acid sequence motif Tyr-Gly-Asp-Thr-Asp-Ser in alpha-like DNA polymerases is required by phage phi 29 DNA polymerase for protein-primed initiation and polymerization" Proc Natl Acad Sci USA. 87(12):4610-4.

Example 4: A Computational Framework for Modeling and Testing the Enzymatic Kinetics of DNA Polymerase, Addressing all Kinetic Processes and Free Variables Simultaneously Polymerase kinetic state transitions are stored in a probability matrix for discrete time steps. A vector of probabilistic state distributions may describe the probability of finding a particular polymerase in a number of polymerase states according to a continuum model. Linear algebra multiplication of the state distribution vector with the state transition probability matrix gives a new vector of polymerase state distributions, describing the effect of the passage of time equal to the discrete time step of the state transition probability matrix.

$$\begin{bmatrix} \text{template 1} \\ \text{template 2} \\ \vdots \end{bmatrix} * [\text{kinetic\_matrix}] = \begin{bmatrix} \text{new state} \\ \text{distributions} \end{bmatrix}$$

By raising the state transition probability matrix to a particular exponential power (eg. 100), we simulate the passage of time of a particular number of discrete time steps (eg. 100 time steps). Using many discrete time steps we simulate DNA polymerization. Steady State Model.

$$1000 \left\{ \underbrace{\begin{bmatrix} \text{template 1} \\ \text{template 2} \\ \vdots \\ \text{template 1000} \end{bmatrix}}_{656} * \begin{bmatrix} 656 \times 656 \\ \text{kinetic\_matrix} \end{bmatrix}^{100} = \begin{bmatrix} 1000 \times 656 \\ \text{new state} \\ \text{distributions} \end{bmatrix} \right.$$

The transition rates are user-defined. The probability matrix is automatically generated using the template sequence and hard-coded state transition rules. A variety of parameters, such as reagent concentrations, kinetic rate values, and probability matrix organization can vary from those described in this example.

Figure 10A:
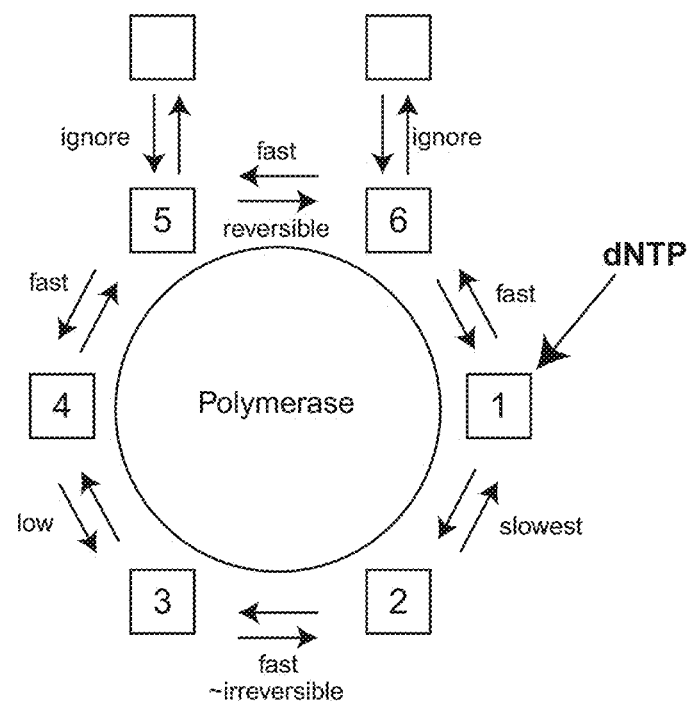
FIG. 10A schematically illustrates an example of a steady state polymerase kinetic model.

FIG. 10A schematically illustrates an example of a steady state polymerase kinetic model. With reference to FIG. 10A:

$$R_p = C_6 K_{61} - C_1 K_{16}$$
$$= C_1 K_{12} - C_2 K_{21}$$
$$= C_2 K_{23} - C_3 K_{32}$$
$$= C_3 K_{34} - C_4 K_{43}$$
$$= C_4 K_{45}$$
$$= C_5 K_{56} - C_6 K_{65}$$

$R_p$=rate of catalysis $C_6$=probability of finding polymerase in state 6

$K_{61}$=transition rate of polymerase in state 6 to state 1

$k_{ij}$=reaction rated $P_{ij}=k_{ij}\Delta t$ reaction rated $P_{ij}$=i→j probability

*$K_{54}\approx 0$ as concentration of pyrophosphate ↓

Figure 10B:
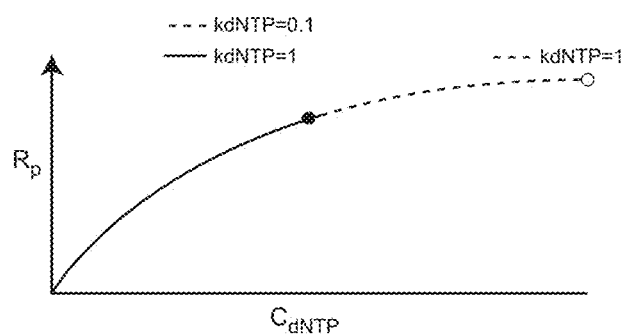
FIG. 10B schematically illustrates a graph that can be used to find $(R_p)_{max}$.

$R_p=C_6 K_{61}-C_1 K_{16}$=rate of catalysis $R_p=(R_p)_{max}$ @$K_{61}\to\infty$, $C_6\to 0$ as a condition of nucleotide concentration increasing to saturation To find $(R_p)_{max}$, refer to the graph shown in FIG. 10B.

*As $\Delta t \downarrow$, find asymptote of $R_p$

Mega Matrix

The following is a single 2-D matrix to capture all possible kinetic states of a polymerase-template-dNTP system (schematically illustrated in FIG. 10C):

| | | Variables | | |
|---|---|---|---|---|
| Pol State | Template Base | Nucleo. Base | Native/Analog | Previous Nucleo. Base |
| 1-4 | A-T | A-T | 0-1 | A-T |
| 5 | A-T | A-T | X | A-T |
| 6 | A-T | X | X | A-T |
| 7 | A-T | A-T | X | A-T |

*This results in a 656-state matrix, where the states are as follows:

| | | | | | |
|---|---|---|---|---|---|
| 1. | 1 | A | A | 0 | A |
| 2. | 1 | A | A | 0 | C |
| 3. | 1 | A | A | 0 | G |
| 4. | 1 | A | A | 0 | T |
| 5. | 1 | A | A | 1 | A |
| 6. | 1 | A | A | 1 | C |
| 7. | 1 | A | A | 1 | G |
| 8. | 1 | A | A | 1 | T |
| 9. | 1 | A | C | 0 | A |
| 652. | 7* | T | G | X | T |
| 653. | 7* | T | T | X | A |
| 654. | 7* | T | T | X | C |
| 655. | 7* | T | T | X | G |
| 656. | 7* | T | T | X | T |

*In this case the state 7 is dissociation of the polymerase from the template, which may optionally be simplified to never happen.

In this case the DNA template is the repeated sequence (ACGT.) For a longer template repeated sequence there will be proportionally more states, to the extent that the longer template repeated sequence does not contain the original template sequence. For example, the probability transition matrix generated for the sequence

. . . [ACGT]ACGT . . .

would be equivalent to the matrix generated for the sequence

. . . [ACGTACGT]ACGT . . .  SEQ ID NO: 65

However, the probability transition matrix generated for the sequence

. . . [AACCGGTT]AACC . . .  SEQ ID NO: 66 would be different, as it contains many state transitions not allowed in the original matrix (eg. polymerase translocation from an "A" to another "A" in the template sequence. Furthermore, since this repeated sequence contains eight Watson-Crick bases instead of four, it would generate a matrix of 1,312 states instead of 656.

Some states do not require all variables to be defined (see above table). For example, characteristics of a nucleotide which has not yet been incorporated in state 6 do not affect the identity of state 6.

| | | | | | |
|---|---|---|---|---|---|
| 577. | 6 | A | X | X | A |

*The Transition rate between two states will be defined as such:

| | | | | | |
|---|---|---|---|---|---|
| 562. | 5 | T | A | X | C |

$P56TAxC = k56TAxC * \text{time\_step}$

Where P56TAxC is the probability of the polymerase completing translocation from state 5 to state 6 with the additional nucleotide-template conditions described by "TAxC". K56TAxC is the transition rate of this translocation.

Currently in this 656 state system, there are 1568 transition rates to define. There are a number of approximations that can be made to reduce the number of inputs the user needs to enter.

The following combinations may be treated equivalently in all states transitions:
Template nucleotide: ACGT
TGCA
Likewise, all mismatches may be treated the same
K12AT0A=k12xZ0Z
K12CG0T=k12xZ0Z
K12CT0T=k12xY0Z
K12CT1C k12xY1Y
X=any variable
Y=any mismatch
Z=any match In this way the user input selection is reduced to ~100 unique transition rate variables. All the explicitly defined rates are automatically assigned the appropriate user inputs.

Building the Mega Matrix

FIG. 10D illustrates the relationship between the current state and the new state. To capitalize on symmetry for the purpose of inserting user defined transition rates into the matrix automatically, the organization of the 656-state matrix can be changed:

| Old | | | | | | New | | | | |
|---|---|---|---|---|---|---|---|---|---|---|
| 1. | 1 | A | A | 0 | A | 1. | A | 1 | A | 0 | A |
| 2. | 1 | A | A | 0 | C | 2. | A | 1 | A | 0 | C |
| ... | ... | ... | ... | ... | ... | ... | ... | ... | ... | ... |
| 656. | 7 | T | T | 1 | T | 656. | T | 7 | T | 1 | T |

This has two advantages:
(1.) the template can be extended with only slight modifications to the matrix. Every Template base in repeated sequence brings an additional 164 states. Previously, new states would have to be interwoven into matrix. See FIG. 10E, which illustrates expansion of the matrix.
(2) The matrix has a higher degree of symmetry than before, making it easier to construct the matrix using automated code:

```
for ii = 1:164
  eval (['...']);
  ...
end % ii
```

Seven "eval" statements (a function which evaluates an artificially constructed command) construct seven polymerase states.

This has been further enhanced to build the matrix for any given template sequence automatically.

A further automation of the generation of the state transition probability matrix is through the building of a concentration matrix, which contains the concentrations of all relevant reagents (polymerase, template, nucleotides, etc). This concentration matrix compliments the rate transition matrix such that (in the linear concentration limit).

kinetic_matrix=rate_transition_matrix.*conc_matrix state_transition_probability_matrix=kinetic_matrix*time_step where each element of the rate transition matrix has been multiplied by its corresponding dependent variable in the concentration matrix. In this way we capture the concentration dependent state transitions (eg. the rate of incorporation of nucleotides is dependent upon the concentration of nucleotides). Elements of the matrix which are not concentration dependent are not changed. Non-linear concentration dependencies may be addressed using a nonlinear formula defining the kinetic matrix.

The following describes the state transition probability matrix (see also FIG. 10D, which illustrates the relationship between the current state and the new state):

Matrix=zeros(656,656);

Matrix(1,[1,139,577])=[1−$p12AA0A$−$p16AA0A$, $p12AA0A$,$p16AA0A$];

. . .

Matrix(2,[2,130,578])=[1−$p12AA0C$−$p16AA0C$, $p12AA0C$,$p16AA0C$];

. . .

Matrix(129,[129,257,1])=[1−$p23AA0A$−$p21AA0A$, $p23AA0A$,$p21AA0A$];

. . .

Matrix(656,[656,580,576])=[1−$p76TTxT$−$p75TTxT$, $p76TTxT$,$p75TTxT$];

where each of the probability values inserted in the matrix have been calculated using user defined transition rates, concentration values, and a discrete time step. Note that the first element of a row is the probability of having no transition between states, and is thus the difference between 100% and the probabilities of all state transitions out of that particular state.

Increasing Efficiency of Simulation:

By raising the state transition probability matrix to a particular exponential power (eg. 100), we simulate the passage of time of a particular number of discrete time steps (eg. 100 time steps).

Further improvements to the efficiency of the simulation may be made through vectorization of many polymerase-template complexes simultaneously.

$$1000 \left\{ \begin{bmatrix} \text{template 1} \\ \text{template 2} \\ \vdots \\ \text{template 1000} \end{bmatrix} * \begin{bmatrix} 656 \times 656 \\ \text{kinetic\_matrix} \end{bmatrix}^{100} = \begin{bmatrix} 1000 \times 656 \\ \text{new state} \\ \text{distributions} \end{bmatrix} \right.$$
$$\underbrace{\hphantom{XXXXXXXXX}}_{656}$$

Figure 10F:
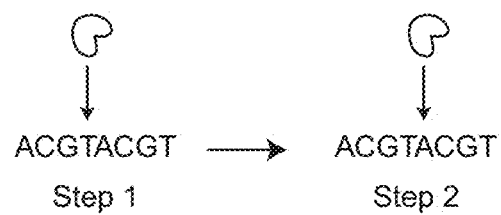
FIG. 10F schematically illustrates that DNA synthesis can be tracked by looking at where the polymerase is on the template.

Speed Limit:

DNA synthesis can be tracked by looking at where pol is on the template. With reference to FIG. 10F:
[1000]="A"
[0100]="C"
etc. . . .

If we move too fast (i.e. too many time steps in the transition matrix exponential), the polymerase may go from "A" straight to "G", making it unclear whether this was forward or reverse translocation. Therefore an error limit (~1e−6) is set that defines an exponential time factor on the kinetic_matrix. The speed limit is such that neither the probability of reverse translocation from "A" to "G" nor the probability of forward translocation from "A" to "T" exceeds the error rate limit. A longer DNA repeat sequence will allow us to move faster, but a repeat sequence which is too long will be computationally intensive.

A further application of this program can be the simulation of reagent consumption rate. Moving at very large step sizes, polymerase movment is simulated along template. This approach uses only one template in a continuous distribution of states (instead of 1000+ templates in discrete states). This tracks reagent consumption over time.

Find the concentration change of reagents based on the current population of the system and based on the transition rate constants:

$d(dTAP_o)_{per\ pol}=C_1\Delta tk16AA0A+C_2\Delta tk16AA0C+\ldots$
$C_{520}\Delta tk16T T0T-C_{145}\Delta tk61AA0A-$
$C_{146}\Delta tk61AA0C-\ldots =C_1p61AA0A+$
$C_{14c}p61AA0C+\ldots C_{145}p61AA0A-$
$C_{146}p61AA0C-\ldots$ Where these probabilities are for a $1e^{-6}$ sec time step from kinetic_matrix: concentration change (Molar) of reagent dTAP (native) in 1 loop cycle where elapsed time=num_steps*$1e^{-6}$ sec

[fast_matrix] = [kinetic_matrix]$^{num\_steps}$

Speed limit: $\dfrac{\Delta C_{max}}{C} < 1\%?$

Fast_matrix= kinetic_matrix$^t$

As N becomes large, the adjustment to concentrations each loop cycle becomes large and inaccurate. This is used to set an exponential time factor on the kinetic_matrix.

Figure 9:
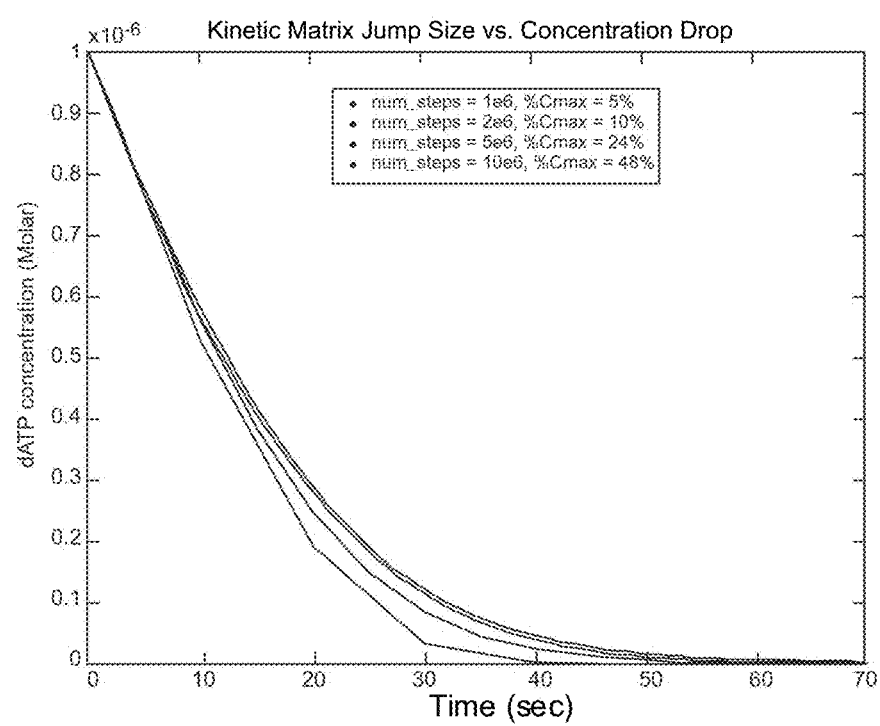
FIG. 9 depicts a plot of kinetic matrix jump size vs. concentration drop.

See FIG. 9, which plots the kinetic matrix jump size vs. concentration drop.

Even taking num_steps=1e6 may give accurate "enough" concentration curves (see the approach to smoothness as step size decreases).

The resulting (4096×4096 double matrix is a reasonable memory limit).

A further application of this program can be the estimation of the polymerase mismatch fraction using either a continuum model or counting model. Currently we say that the $2^{nd}$ previous template—nucleotide pair is always a match. (This is to reduce size of matrix by 4× . . . the error should be small unless there is lots of exonuclease activity).

Therefore, any forward translocation from state 5 with a previous mismatch becomes a permanent mismatch (it just won't look that way if we back up).

forward total translocation rate=$C_5.*C_6-C_6.*k_{65}$ reaction=(mismatch rate)/(total rate)

$C_5$ represents concentration of all matrix states with pol in state 5 (see pg. 128)
$k_{56}$ is the full set of all corresponding rates for forward translocation forward mismatch translocation=$C_5^{(m)}.*k_{56}^{(m)}-$
$C_6^{(m)}.*k_{65}^{(m)}$ (In reverse translocation, we never end up in pol state 5 with previous mismatch, see above).

We can also make a counting model which counts number of polymerase/template complexes which have previous template/nucleotide mismatch and which also do forward translocation (making mismatch permanent), and average this over all polymerase to get a mismatch fraction. This should be in the same ballpark as continuum model estimate above.

Figure 10G:
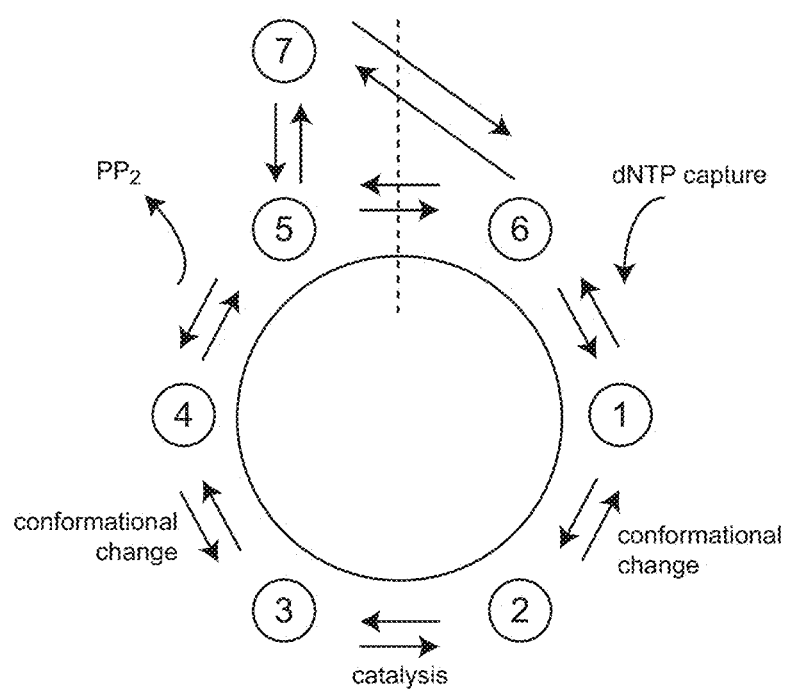
FIG. 10G schematically illustrates a kinetic model of replication by DNA polymerase.

1) First set all rate constants equal to T7 polymerase as shown by Patel, et al. (1991) "Pre-Steady-State Kinetic Analysis of Processive DNA Replication Including Complete Characterization of an Exonuclease-Deficient Mutant" Biochemistry 30:511-525. See the model illustrated in FIG. 10G.

Specific rate constants, etc.
$K_{61} \geq 50$ µm$^{-1}$ s$^{-1}$
$K_{12} = 300$ µm$^{-1}$ s$^{-1}$
$K_{23} \geq 9000$ µm$^{-1}$ s$^{-1}$
$K_{34} = 1200$ µm$^{-1}$ s$^{-1}$
$K_{645} \geq 1000$ µm$^{-1}$ s$^{-1}$
$K_{16} \geq 1000$ µm$^{-1}$ s$^{-1}$
$K_{21} = 1001$ µm$^{-1}$ s$^{-1}$
$K_{32} = 18,0001$ µm$^{-1}$ s$^{-1}$
$K_{43} = 18$ µm$^{-1}$ s$^{-1}$
$K_{54} \geq 0.5$ µm$^{-1}$ s$^{-1}$
$(V_{max})_{native} = 50$ bps
$(V_{max})_{analog} = 5$ bps
$(k_m)_{native} = 0.2$ m
$(k_m)_{analog} = 6$ m 2) Using dNTP concentration saturation ($\geq 1$ mM), set $V_{max} = 50$ bps by changing $k_{12}$ (primarily) and other rate constants (if necessary). Keep all analog transition rates the same as native dNTP transition rates. For now cut dissociation (rate—0)

3) Using analog-dNTP concentration saturation ($\geq 1$ mM), set $V_{max} = 5$ bp by changing $k_{45}$ for analogs only.

4) Set $(k_m)_{native} = 0.2$ µm by setting native dNTP concentration to 0.2 µm and changing $k_{61}$ (natives only) such that V=25 bps.

5) Set $(k_m)_{native} = 6$ µm by setting analog dNTP concentration to 6 µm and changing $k_{61}$ (analogs only) such that V—2.5 bps.

native dNTP's
$k_{61} = 365$ µm$^{-1}$ s$^{-1}$
$k_{12} = 60$ µm$^{-1}$ s$^{-1}$
$k_{23} = 9000$ µm$^{-1}$ s$^{-1}$
$k_{34} = 1200$ µm$^{-1}$ s$^{-1}$
$k_{45} = 1000$ µm$^{-1}$ s$^{-1}$
$k_{56} = 500$ µm$^{-1}$ s$^{-1}$
$k_{16} = 10$ µm$^{-1}$ s$^{-1}$
$k_{21} = 100$ µm$^{-1}$ s$^{-1}$
$k_{32} = 1800$ µm$^{-1}$ s$^{-1}$
$k_{43} = 18$ µm$^{-1}$ s$^{-1}$
$k_{54} = 0.5$ µm$^{-1}$ s$^{-1}$
$k_{65} = 100$ µm$^{-1}$ s$^{-1}$
analog dNTP's
$k_{61} = 1.1$ µm$^{-1}$ s$^{-1}$
$k_{12} = 60$ µm$^{-1}$ s$^{-1}$
$k_{23} = 9000$ µm$^{-1}$ s$^{-1}$
$k_{34} = 5.5$ µm$^{-1}$ s$^{-1}$
$k_{45} = 5.5$ µm$^{-1}$ s$^{-1}$
$k_{56} = 500$ µm$^{-1}$ s$^{-1}$
$k_{16} = 10$ µm$^{-1}$ s$^{-1}$
$k_{21} = 100$ µm$^{-1}$ s$^{-1}$
$k_{32} = 1800$ µm$^{-1}$ s$^{-1}$
$k_{43} = 18$ µm$^{-1}$ s$^{-1}$
$k_{54} = 0.1$ µm$^{-1}$ s$^{-1}$
$k_{65} = 100$ µm$^{-1}$ s$^{-1}$ All rates will be subject to calibration by future experiments as well.

pol_index.m: Initializes all necessary matrix index lists and pointers based on DNA sequence.

Pol_ratematrix.m: Takes excel file as input, which contains a list of all unique rate constants, produces transition rate matrix based on DNA sequence.

Pol_conmatrix.m: Takes reagent concentrations, builds concentration matrix such that:

Probability
matrix=time_step*rate_matrix*conc_matrix (for all non-diagonal elements)
Pol_dntp_concumption.m: Calculates reagent consumption rates based on continuum model.
POL_dna.m: Combines all former functions of POL_DNA, POL_REAGENTS, POL_CURVEMAP,
tracks all former consumption,
tracts length distribution of DNA synthesis,
tracks free template, completed dsDNA template, template currently being worked on,
multiple concentration runs possible
user defined repeating DNA sequence, finite length templates
pol_metal.m: Full embodiment of Mg+ depletion experiment, using stripped down version of POL_DNA.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A composition comprising a recombinant DNA polymerase, which recombinant polymerase comprises an amino acid sequence that is at least 80% identical to SEQ ID NO:1, which recombinant polymerase comprises an amino acid substitution at position K135, wherein identification of positions is relative to SEQ ID NO:1, and which recombinant polymerase exhibits polymerase activity.

2. The composition of claim 1, wherein the recombinant polymerase comprises one or more mutations selected from the group consisting of a K135A substitution, a K135D substitution, and a K135E substitution, wherein identification of positions is relative to SEQ ID NO:1.

3. The composition of claim 1, wherein the recombinant polymerase comprises an amino acid sequence that is at least 90% identical to SEQ ID NO:1.

4. The composition of claim 1, wherein the recombinant polymerase comprises a mutation that inhibits exonuclease activity of the polymerase.

5. The composition of claim 1, wherein the recombinant polymerase comprises one or more exogenous affinity tag sequences.

6. The composition of claim 5, wherein the affinity tag sequence is selected from: a 6 His tag sequence, a GST tag, an HA tag sequence, a plurality of 6 His tag sequences, a plurality of GST tags, a plurality of HA tag sequences and combinations thereof.

7. The composition of claim 1, comprising a phosphate-labeled nucleotide analog.

8. The composition of claim 7, wherein the nucleotide analog comprises a fluorophore.

9. The composition of claim 1, comprising a phosphate-labeled nucleotide analog and a DNA template, wherein the recombinant polymerase incorporates the nucleotide analog into a copy nucleic acid in response to the DNA template.

10. The composition of claim 9, wherein the template is a circular template.

11. The composition of claim 1, wherein the composition is present in a DNA sequencing system.

12. The composition of claim 11, wherein the sequencing system comprises a zero-mode waveguide.

13. The composition of claim 12, wherein the recombinant polymerase is immobilized on a surface of the zero-mode waveguide in an active form.

14. A method of sequencing a DNA template, the method comprising:
　a) providing a reaction mixture comprising:
　　the DNA template,
　　a replication initiating moiety that complexes with or is integral to the template,
　　the recombinant DNA polymerase of claim 1, wherein the polymerase is capable of replicating at least a portion of the template using the moiety in a template-dependent polymerization reaction, and
　　one or more nucleotides and/or nucleotide analogs;
　b) subjecting the reaction mixture to a polymerization reaction in which the recombinant polymerase replicates at least a portion of the template in a template-dependent manner, whereby the one or more nucleotides and/or nucleotide analogs are incorporated into the resulting DNA; and
　c) identifying a time sequence of incorporation of the one or more nucleotides and/or nucleotide analogs into the resulting DNA.

15. The method of claim 14, wherein the subjecting and identifying steps are performed in a zero mode waveguide.

16. A method of making a DNA, the method comprising:
　(a) providing a reaction mixture comprising:
　　a template,
　　a replication initiating moiety that complexes with or is integral to the template,
　　the recombinant DNA polymerase of claim 1, which polymerase is capable of replicating at least a portion of the template using the moiety in a template-dependent polymerase reaction, and one or more nucleotides and/or nucleotide analogs; and (b) reacting the mixture such that the polymerase replicates at least a portion of the template in a template-dependent manner, whereby the one or more nucleotides and/or nucleotide analogs are incorporated into the resulting DNA.

17. The method of claim 16, wherein the mixture is reacted in a zero mode waveguide.

18. The method of claim 16, the method comprising detecting incorporation of at least one of the nucleotides and/or nucleotide analogs.

* * * * *

SEQUENCE LISTING

<160> NUMBER OF SEQ ID NOS: 66

<210> SEQ ID NO 1
<211> LENGTH: 575
<212> TYPE: PRT
<213> ORGANISM: Bacteriophage phi-29

<400> SEQUENCE: 1

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
```

```
                420             425             430
Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 862
<212> TYPE: PRT
<213> ORGANISM: Artificial
<220> FEATURE:
<223> OTHER INFORMATION: GST, His, and S-tagged N62D mutant Phi29
      polymerase

<400> SEQUENCE: 2

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
            275                 280                 285

Lys His Met Pro Arg Lys Met Tyr Ser Cys Asp Phe Glu Thr Thr Thr
290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
            355                 360                 365

Ser Ala Asp Gly Leu Pro Asn Thr Tyr Asn Thr Ile Ile Ser Arg Met
370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Lys Asp Phe Lys Leu Thr Val Leu Lys Gly Asp
            420                 425                 430

Ile Asp Tyr His Lys Glu Arg Pro Val Gly Tyr Lys Ile Thr Pro Glu
            435                 440                 445

Glu Tyr Ala Tyr Ile Lys Asn Asp Ile Gln Ile Ile Ala Glu Ala Leu
450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
                485                 490                 495

Val Phe Pro Thr Leu Ser Leu Gly Leu Asp Lys Glu Val Arg Tyr Ala
            500                 505                 510

Tyr Arg Gly Gly Phe Thr Trp Leu Asn Asp Arg Phe Lys Glu Lys Glu
            515                 520                 525

Ile Gly Glu Gly Met Val Phe Asp Val Asn Ser Leu Tyr Pro Ala Gln
530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
                565                 570                 575

Cys Glu Phe Glu Leu Lys Glu Gly Tyr Ile Pro Thr Ile Gln Ile Lys
            580                 585                 590

Arg Ser Arg Phe Tyr Lys Gly Asn Glu Tyr Leu Lys Ser Ser Gly Gly
            595                 600                 605

Glu Ile Ala Asp Leu Trp Leu Ser Asn Val Asp Leu Glu Leu Met Lys
610                 615                 620

Glu His Tyr Asp Leu Tyr Asn Val Glu Tyr Ile Ser Gly Leu Lys Phe
```

```
                625                 630                 635                 640
Lys Ala Thr Thr Gly Leu Phe Lys Asp Phe Ile Asp Lys Trp Thr Tyr
                    645                 650                 655
Ile Lys Thr Thr Ser Glu Gly Ala Ile Lys Gln Leu Ala Lys Leu Met
                660                 665                 670
Leu Asn Ser Leu Tyr Gly Lys Phe Ala Ser Asn Pro Asp Val Thr Gly
            675                 680                 685
Lys Val Pro Tyr Leu Lys Glu Asn Gly Ala Leu Gly Phe Arg Leu Gly
        690                 695                 700
Glu Glu Glu Thr Lys Asp Pro Val Tyr Thr Pro Met Gly Val Phe Ile
705                 710                 715                 720
Thr Ala Trp Ala Arg Tyr Thr Thr Ile Thr Ala Ala Gln Ala Cys Tyr
                    725                 730                 735
Asp Arg Ile Ile Tyr Cys Asp Thr Asp Ser Ile His Leu Thr Gly Thr
                740                 745                 750
Glu Ile Pro Asp Val Ile Lys Asp Ile Val Asp Pro Lys Lys Leu Gly
            755                 760                 765
Tyr Trp Ala His Glu Ser Thr Phe Lys Arg Ala Lys Tyr Leu Arg Gln
        770                 775                 780
Lys Thr Tyr Ile Gln Asp Ile Tyr Met Lys Glu Val Asp Gly Lys Leu
785                 790                 795                 800
Val Glu Gly Ser Pro Asp Asp Tyr Thr Asp Ile Lys Phe Ser Val Lys
                    805                 810                 815
Cys Ala Gly Met Thr Asp Lys Ile Lys Lys Glu Val Thr Phe Glu Asn
                820                 825                 830
Phe Lys Val Gly Phe Ser Arg Lys Met Lys Pro Lys Pro Val Gln Val
            835                 840                 845
Pro Gly Gly Val Val Leu Val Asp Asp Thr Phe Thr Ile Lys
        850                 855                 860

<210> SEQ ID NO 3
<211> LENGTH: 862
<212> TYPE: PRT
<213> ORGANISM: Artificial
<220> FEATURE:
<223> OTHER INFORMATION: GST, His, and S-tagged K135A-N62D mutant Phi29
      polymerase

<400> SEQUENCE: 3

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
        50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
```

```
Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Gly Ser Thr Ser
210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
            275                 280                 285

Lys His Met Pro Arg Lys Met Tyr Ser Cys Asp Phe Glu Thr Thr Thr
290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
                340                 345                 350

Asp Gly Ala Phe Ile Ile Asn Trp Leu Glu Arg Asn Gly Phe Lys Trp
                355                 360                 365

Ser Ala Asp Gly Leu Pro Asn Thr Tyr Asn Thr Ile Ile Ser Arg Met
                370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Ala Asp Phe Lys Leu Thr Val Leu Lys Gly Asp
                420                 425                 430

Ile Asp Tyr His Lys Glu Arg Pro Val Gly Tyr Lys Ile Thr Pro Glu
                435                 440                 445

Glu Tyr Ala Tyr Ile Lys Asn Asp Ile Gln Ile Ile Ala Glu Ala Leu
450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
                485                 490                 495

Val Phe Pro Thr Leu Ser Leu Gly Leu Asp Lys Glu Val Arg Tyr Ala
                500                 505                 510

Tyr Arg Gly Gly Phe Thr Trp Leu Asn Asp Arg Phe Lys Glu Lys Glu
            515                 520                 525

Ile Gly Glu Gly Met Val Phe Asp Val Asn Ser Leu Tyr Pro Ala Gln
530                 535                 540

Met Tyr Ser Arg Leu Leu Pro Tyr Gly Glu Pro Ile Val Phe Glu Gly
```

```
            545                 550                 555                 560
Lys Tyr Val Trp Asp Glu Asp Tyr Pro Leu His Ile Gln His Ile Arg
                565                 570                 575

Cys Glu Phe Glu Leu Lys Glu Gly Tyr Ile Pro Thr Ile Gln Ile Lys
                580                 585                 590

Arg Ser Arg Phe Tyr Lys Gly Asn Glu Tyr Leu Lys Ser Ser Gly Gly
                595                 600                 605

Glu Ile Ala Asp Leu Trp Leu Ser Asn Val Asp Leu Glu Leu Met Lys
                610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                645                 650                 655

Ile Lys Thr Thr Ser Glu Gly Ala Ile Lys Gln Leu Ala Lys Leu Met
                660                 665                 670

Leu Asn Ser Leu Tyr Gly Lys Phe Ala Ser Asn Pro Asp Val Thr Gly
                675                 680                 685

Lys Val Pro Tyr Leu Lys Glu Asn Gly Ala Leu Gly Phe Arg Leu Gly
                690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                725                 730                 735

Asp Arg Ile Ile Tyr Cys Asp Thr Asp Ser Ile His Leu Thr Gly Thr
                740                 745                 750

Glu Ile Pro Asp Val Ile Lys Asp Ile Val Asp Pro Lys Lys Leu Gly
                755                 760                 765

Tyr Trp Ala His Glu Ser Thr Phe Lys Arg Ala Lys Tyr Leu Arg Gln
                770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
                805                 810                 815

Cys Ala Gly Met Thr Asp Lys Ile Lys Lys Glu Val Thr Phe Glu Asn
                820                 825                 830

Phe Lys Val Gly Phe Ser Arg Lys Met Lys Pro Lys Pro Val Gln Val
                835                 840                 845

Pro Gly Gly Val Val Leu Val Asp Asp Thr Phe Thr Ile Lys
                850                 855                 860

<210> SEQ ID NO 4
<211> LENGTH: 862
<212> TYPE: PRT
<213> ORGANISM: Artificial
<220> FEATURE:
<223> OTHER INFORMATION: GST, His, and S-tagged E375H-N62D mutant Phi29
      polymerase

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45
```

-continued

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
            275                 280                 285

Lys His Met Pro Arg Lys Met Tyr Ser Cys Asp Phe Glu Thr Thr Thr
290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
                340                 345                 350

Asp Gly Ala Phe Ile Ile Asn Trp Leu Glu Arg Asn Gly Phe Lys Trp
            355                 360                 365

Ser Ala Asp Gly Leu Pro Asn Thr Tyr Asn Thr Ile Ile Ser Arg Met
370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Lys Asp Phe Lys Leu Thr Val Leu Lys Gly Asp
                420                 425                 430

Ile Asp Tyr His Lys Glu Arg Pro Val Gly Tyr Lys Ile Thr Pro Glu
            435                 440                 445

Glu Tyr Ala Tyr Ile Lys Asn Asp Ile Gln Ile Ala Glu Ala Leu
450                 455                 460

Leu Ile Gln Phe Lys Gln Gly Leu Asp Arg Met Thr Ala Gly Ser Asp

```
                465                 470                 475                 480

Ser Leu Lys Gly Phe Lys Asp Ile Ile Thr Lys Phe Lys Lys
                        485                 490                 495

Val Phe Pro Thr Leu Ser Leu Gly Leu Asp Lys Glu Val Arg Tyr Ala
                        500                 505                 510

Tyr Arg Gly Gly Phe Thr Trp Leu Asn Asp Arg Phe Lys Glu Lys Glu
                        515                 520                 525

Ile Gly Glu Gly Met Val Phe Asp Val Asn Ser Leu Tyr Pro Ala Gln
                        530                 535                 540

Met Tyr Ser Arg Leu Leu Pro Tyr Gly Glu Pro Ile Val Phe Glu Gly
        545                 550                 555                 560

Lys Tyr Val Trp Asp Glu Asp Tyr Pro Leu His Ile Gln His Ile Arg
                        565                 570                 575

Cys Glu Phe Glu Leu Lys Glu Gly Tyr Ile Pro Thr Ile Gln Ile Lys
                        580                 585                 590

Arg Ser Arg Phe Tyr Lys Gly Asn Glu Tyr Leu Lys Ser Ser Gly Gly
                        595                 600                 605

Glu Ile Ala Asp Leu Trp Leu Ser Asn Val Asp Leu Glu Leu Met Lys
                        610                 615                 620

Glu His Tyr Asp Leu Tyr Asn Val Glu Tyr Ile Ser Gly Leu Lys Phe
        625                 630                 635                 640

Lys Ala Thr Thr Gly Leu Phe Lys Asp Phe Ile Asp Lys Trp Thr Tyr
                        645                 650                 655

Ile Lys Thr Thr Ser His Gly Ala Ile Lys Gln Leu Ala Lys Leu Met
                        660                 665                 670

Leu Asn Ser Leu Tyr Gly Lys Phe Ala Ser Asn Pro Asp Val Thr Gly
                        675                 680                 685

Lys Val Pro Tyr Leu Lys Glu Asn Gly Ala Leu Gly Phe Arg Leu Gly
                        690                 695                 700

Glu Glu Glu Thr Lys Asp Pro Val Tyr Thr Pro Met Gly Val Phe Ile
        705                 710                 715                 720

Thr Ala Trp Ala Arg Tyr Thr Thr Ile Thr Ala Ala Gln Ala Cys Tyr
                        725                 730                 735

Asp Arg Ile Ile Tyr Cys Asp Thr Asp Ser Ile His Leu Thr Gly Thr
                        740                 745                 750

Glu Ile Pro Asp Val Ile Lys Asp Ile Val Asp Pro Lys Lys Leu Gly
                        755                 760                 765

Tyr Trp Ala His Glu Ser Thr Phe Lys Arg Ala Lys Tyr Leu Arg Gln
        770                 775                 780

Lys Thr Tyr Ile Gln Asp Ile Tyr Met Lys Glu Val Asp Gly Lys Leu
        785                 790                 795                 800

Val Glu Gly Ser Pro Asp Asp Tyr Thr Asp Ile Lys Phe Ser Val Lys
                        805                 810                 815

Cys Ala Gly Met Thr Asp Lys Ile Lys Lys Glu Val Thr Phe Glu Asn
                        820                 825                 830

Phe Lys Val Gly Phe Ser Arg Lys Met Lys Pro Lys Pro Val Gln Val
                        835                 840                 845

Pro Gly Gly Val Val Leu Val Asp Asp Thr Phe Thr Ile Lys
                        850                 855                 860

<210> SEQ ID NO 5
<211> LENGTH: 862
<212> TYPE: PRT
<213> ORGANISM: Artificial
```

<220> FEATURE:
<223> OTHER INFORMATION: GST, His, and S-tagged E375S-N62D mutant Phi29 polymerase

<400> SEQUENCE: 5

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
        275                 280                 285

Lys His Met Pro Arg Lys Met Tyr Ser Cys Asp Phe Glu Thr Thr Thr
    290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
        355                 360                 365

Ser Ala Asp Gly Leu Pro Asn Thr Tyr Asn Thr Ile Ile Ser Arg Met
    370                 375                 380

Gly Gln Trp Tyr Met Ile Asp Ile Cys Leu Gly Tyr Lys Gly Lys Arg
```

-continued

```
            385                 390                 395                 400
Lys Ile His Thr Val Ile Tyr Asp Ser Leu Lys Lys Leu Pro Phe Pro
                    405                 410                 415
Val Lys Lys Ile Ala Lys Asp Phe Lys Leu Thr Val Leu Lys Gly Asp
                420                 425                 430
Ile Asp Tyr His Lys Glu Arg Pro Val Gly Tyr Lys Ile Thr Pro Glu
            435                 440                 445
Glu Tyr Ala Tyr Ile Lys Asn Asp Ile Gln Ile Ala Glu Ala Leu
        450                 455                 460
Leu Ile Gln Phe Lys Gln Gly Leu Asp Arg Met Thr Ala Gly Ser Asp
465                 470                 475                 480
Ser Leu Lys Gly Phe Lys Asp Ile Ile Thr Lys Lys Phe Lys Lys
                    485                 490                 495
Val Phe Pro Thr Leu Ser Leu Gly Leu Asp Lys Glu Val Arg Tyr Ala
                500                 505                 510
Tyr Arg Gly Gly Phe Thr Trp Leu Asn Asp Arg Phe Lys Glu Lys Glu
            515                 520                 525
Ile Gly Glu Gly Met Val Phe Asp Val Asn Ser Leu Tyr Pro Ala Gln
        530                 535                 540
Met Tyr Ser Arg Leu Leu Pro Tyr Gly Glu Pro Ile Val Phe Glu Gly
545                 550                 555                 560
Lys Tyr Val Trp Asp Glu Asp Tyr Pro Leu His Ile Gln His Ile Arg
                    565                 570                 575
Cys Glu Phe Glu Leu Lys Glu Gly Tyr Ile Pro Thr Ile Gln Ile Lys
                580                 585                 590
Arg Ser Arg Phe Tyr Lys Gly Asn Glu Tyr Leu Lys Ser Ser Gly Gly
            595                 600                 605
Glu Ile Ala Asp Leu Trp Leu Ser Asn Val Asp Leu Glu Leu Met Lys
        610                 615                 620
Glu His Tyr Asp Leu Tyr Asn Val Glu Tyr Ile Ser Gly Leu Lys Phe
625                 630                 635                 640
Lys Ala Thr Thr Gly Leu Phe Lys Asp Phe Ile Asp Lys Trp Thr Tyr
                    645                 650                 655
Ile Lys Thr Thr Ser Ser Gly Ala Ile Lys Gln Leu Ala Lys Leu Met
                660                 665                 670
Leu Asn Ser Leu Tyr Gly Lys Phe Ala Ser Asn Pro Asp Val Thr Gly
            675                 680                 685
Lys Val Pro Tyr Leu Lys Glu Asn Gly Ala Leu Gly Phe Arg Leu Gly
        690                 695                 700
Glu Glu Glu Thr Lys Asp Pro Val Tyr Thr Pro Met Gly Val Phe Ile
705                 710                 715                 720
Thr Ala Trp Ala Arg Tyr Thr Thr Ile Thr Ala Ala Gln Ala Cys Tyr
                    725                 730                 735
Asp Arg Ile Ile Tyr Cys Asp Thr Asp Ser Ile His Leu Thr Gly Thr
                740                 745                 750
Glu Ile Pro Asp Val Ile Lys Asp Ile Val Asp Pro Lys Lys Leu Gly
            755                 760                 765
Tyr Trp Ala His Glu Ser Thr Phe Lys Arg Ala Lys Tyr Leu Arg Gln
        770                 775                 780
Lys Thr Tyr Ile Gln Asp Ile Tyr Met Lys Glu Val Asp Gly Lys Leu
785                 790                 795                 800
Val Glu Gly Ser Pro Asp Asp Tyr Thr Asp Ile Lys Phe Ser Val Lys
                    805                 810                 815
```

-continued

```
Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
            835                 840                 845

Pro Gly Gly Val Val Leu Val Asp Asp Thr Phe Thr Ile Lys
            850                 855                 860

<210> SEQ ID NO 6
<211> LENGTH: 862
<212> TYPE: PRT
<213> ORGANISM: Artificial
<220> FEATURE:
<223> OTHER INFORMATION: GST, His, and S-tagged E375K-N62D mutant Phi29
      polymerase

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
        275                 280                 285

Lys His Met Pro Arg Lys Met Tyr Ser Cys Asp Phe Glu Thr Thr Thr
    290                 295                 300

Lys Val Glu Asp Cys Arg Val Trp Ala Tyr Gly Tyr Met Asn Ile Glu
```

```
            305                 310                 315                 320
Asp His Ser Glu Tyr Lys Ile Gly Asn Ser Leu Asp Glu Phe Met Ala
                    325                 330                 335

Trp Val Leu Lys Val Gln Ala Asp Leu Tyr Phe His Asp Leu Lys Phe
                    340                 345                 350

Asp Gly Ala Phe Ile Ile Asn Trp Leu Glu Arg Asn Gly Phe Lys Trp
                    355                 360                 365

Ser Ala Asp Gly Leu Pro Asn Thr Tyr Asn Thr Ile Ile Ser Arg Met
                    370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                    405                 410                 415

Val Lys Lys Ile Ala Lys Asp Phe Lys Leu Thr Val Leu Lys Gly Asp
                    420                 425                 430

Ile Asp Tyr His Lys Glu Arg Pro Val Gly Tyr Lys Ile Thr Pro Glu
                    435                 440                 445

Glu Tyr Ala Tyr Ile Lys Asn Asp Ile Gln Ile Ile Ala Glu Ala Leu
                    450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
                    485                 490                 495

Val Phe Pro Thr Leu Ser Leu Gly Leu Asp Lys Glu Val Arg Tyr Ala
                    500                 505                 510

Tyr Arg Gly Gly Phe Thr Trp Leu Asn Asp Arg Phe Lys Glu Lys Glu
                    515                 520                 525

Ile Gly Glu Gly Met Val Phe Asp Val Asn Ser Leu Tyr Pro Ala Gln
                    530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
                    565                 570                 575

Cys Glu Phe Glu Leu Lys Glu Gly Tyr Ile Pro Thr Ile Gln Ile Lys
                    580                 585                 590

Arg Ser Arg Phe Tyr Lys Gly Asn Glu Tyr Leu Lys Ser Ser Gly Gly
                    595                 600                 605

Glu Ile Ala Asp Leu Trp Leu Ser Asn Val Asp Leu Glu Leu Met Lys
                    610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                    645                 650                 655

Ile Lys Thr Thr Ser Lys Gly Ala Ile Lys Gln Leu Ala Lys Leu Met
                    660                 665                 670

Leu Asn Ser Leu Tyr Gly Lys Phe Ala Ser Asn Pro Asp Val Thr Gly
                    675                 680                 685

Lys Val Pro Tyr Leu Lys Glu Asn Gly Ala Leu Gly Phe Arg Leu Gly
                    690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                    725                 730                 735
```

Asp Arg Ile Ile Tyr Cys Asp Thr Asp Ser Ile His Leu Thr Gly Thr
            740                 745                 750

Glu Ile Pro Asp Val Ile Lys Asp Ile Val Asp Pro Lys Lys Leu Gly
            755                 760                 765

Tyr Trp Ala His Glu Ser Thr Phe Lys Arg Ala Lys Tyr Leu Arg Gln
770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
            805                 810                 815

Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
            835                 840                 845

Pro Gly Gly Val Val Leu Val Asp Asp Thr Phe Thr Ile Lys
            850                 855                 860

<210> SEQ ID NO 7
<211> LENGTH: 862
<212> TYPE: PRT
<213> ORGANISM: Artificial
<220> FEATURE:
<223> OTHER INFORMATION: GST, His, and S-tagged E375R-N62D mutant Phi29
      polymerase

<400> SEQUENCE: 7

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg

```
            225                 230                 235                 240
Gly Ser Thr Ala Ile Gly Met Lys Glu Thr Ala Ala Ala Lys Phe Glu
                245                 250                 255
Arg Gln His Met Asp Ser Pro Asp Leu Gly Thr Gly Gly Gly Ser Gly
                260                 265                 270
Asp Asp Asp Asp Lys Ser Pro Met Gly Tyr Arg Gly Ser Glu Phe Met
                275                 280                 285
Lys His Met Pro Arg Lys Met Tyr Ser Cys Asp Phe Glu Thr Thr Thr
                290                 295                 300
Lys Val Glu Asp Cys Arg Val Trp Ala Tyr Gly Tyr Met Asn Ile Glu
305                 310                 315                 320
Asp His Ser Glu Tyr Lys Ile Gly Asn Ser Leu Asp Glu Phe Met Ala
                325                 330                 335
Trp Val Leu Lys Val Gln Ala Asp Leu Tyr Phe His Asp Leu Lys Phe
                340                 345                 350
Asp Gly Ala Phe Ile Ile Asn Trp Leu Glu Arg Asn Gly Phe Lys Trp
                355                 360                 365
Ser Ala Asp Gly Leu Pro Asn Thr Tyr Asn Thr Ile Ile Ser Arg Met
                370                 375                 380
Gly Gln Trp Tyr Met Ile Asp Ile Cys Leu Gly Tyr Lys Gly Lys Arg
385                 390                 395                 400
Lys Ile His Thr Val Ile Tyr Asp Ser Leu Lys Lys Leu Pro Phe Pro
                405                 410                 415
Val Lys Lys Ile Ala Lys Asp Phe Lys Leu Thr Val Leu Lys Gly Asp
                420                 425                 430
Ile Asp Tyr His Lys Glu Arg Pro Val Gly Tyr Lys Ile Thr Pro Glu
                435                 440                 445
Glu Tyr Ala Tyr Ile Lys Asn Asp Ile Gln Ile Ile Ala Glu Ala Leu
                450                 455                 460
Leu Ile Gln Phe Lys Gln Gly Leu Asp Arg Met Thr Ala Gly Ser Asp
465                 470                 475                 480
Ser Leu Lys Gly Phe Lys Asp Ile Ile Thr Thr Lys Lys Phe Lys Lys
                485                 490                 495
Val Phe Pro Thr Leu Ser Leu Gly Leu Asp Lys Glu Val Arg Tyr Ala
                500                 505                 510
Tyr Arg Gly Gly Phe Thr Trp Leu Asn Asp Arg Phe Lys Glu Lys Glu
                515                 520                 525
Ile Gly Glu Gly Met Val Phe Asp Val Asn Ser Leu Tyr Pro Ala Gln
                530                 535                 540
Met Tyr Ser Arg Leu Leu Pro Tyr Gly Glu Pro Ile Val Phe Glu Gly
545                 550                 555                 560
Lys Tyr Val Trp Asp Glu Asp Tyr Pro Leu His Ile Gln His Ile Arg
                565                 570                 575
Cys Glu Phe Glu Leu Lys Glu Gly Tyr Ile Pro Thr Ile Gln Ile Lys
                580                 585                 590
Arg Ser Arg Phe Tyr Lys Gly Asn Glu Tyr Leu Lys Ser Ser Gly Gly
                595                 600                 605
Glu Ile Ala Asp Leu Trp Leu Ser Asn Val Asp Leu Glu Leu Met Lys
                610                 615                 620
Glu His Tyr Asp Leu Tyr Asn Val Glu Tyr Ile Ser Gly Leu Lys Phe
625                 630                 635                 640
Lys Ala Thr Thr Gly Leu Phe Lys Asp Phe Ile Asp Lys Trp Thr Tyr
                645                 650                 655
```

```
Ile Lys Thr Thr Ser Arg Gly Ala Ile Lys Gln Leu Ala Lys Leu Met
            660                 665                 670

Leu Asn Ser Leu Tyr Gly Lys Phe Ala Ser Asn Pro Asp Val Thr Gly
            675                 680                 685

Lys Val Pro Tyr Leu Lys Glu Asn Gly Ala Leu Gly Phe Arg Leu Gly
690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                725                 730                 735

Asp Arg Ile Ile Tyr Cys Asp Thr Asp Ser Ile His Leu Thr Gly Thr
            740                 745                 750

Glu Ile Pro Asp Val Ile Lys Asp Ile Val Asp Pro Lys Lys Leu Gly
            755                 760                 765

Tyr Trp Ala His Glu Ser Thr Phe Lys Arg Ala Lys Tyr Leu Arg Gln
770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
                805                 810                 815

Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
            835                 840                 845

Pro Gly Gly Val Val Leu Val Asp Asp Thr Phe Thr Ile Lys
850                 855                 860

<210> SEQ ID NO 8
<211> LENGTH: 862
<212> TYPE: PRT
<213> ORGANISM: Artificial
<220> FEATURE:
<223> OTHER INFORMATION: GST, His, and S-tagged L384R-N62D mutant Phi29
      polymerase

<400> SEQUENCE: 8

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
```

```
            145                 150                 155                 160
    Val Val Leu Tyr Met Asp Pro Met Cys Leu Asp Ala Phe Pro Lys Leu
                        165                 170                 175
    Val Cys Phe Lys Lys Arg Ile Glu Ala Ile Pro Gln Ile Asp Lys Tyr
                        180                 185                 190
    Leu Lys Ser Ser Lys Tyr Ile Ala Trp Pro Leu Gln Gly Trp Gln Ala
                        195                 200                 205
    Thr Phe Gly Gly Gly Asp His Pro Pro Lys Ser Asp Gly Ser Thr Ser
            210                 215                 220
    Gly Ser Gly His His His His His His Ser Ala Gly Leu Val Pro Arg
    225                 230                 235                 240
    Gly Ser Thr Ala Ile Gly Met Lys Glu Thr Ala Ala Ala Lys Phe Glu
                        245                 250                 255
    Arg Gln His Met Asp Ser Pro Asp Leu Gly Thr Gly Gly Gly Ser Gly
                        260                 265                 270
    Asp Asp Asp Asp Lys Ser Pro Met Gly Tyr Arg Gly Ser Glu Phe Met
                        275                 280                 285
    Lys His Met Pro Arg Lys Met Tyr Ser Cys Asp Phe Glu Thr Thr Thr
            290                 295                 300
    Lys Val Glu Asp Cys Arg Val Trp Ala Tyr Gly Tyr Met Asn Ile Glu
    305                 310                 315                 320
    Asp His Ser Glu Tyr Lys Ile Gly Asn Ser Leu Asp Glu Phe Met Ala
                        325                 330                 335
    Trp Val Leu Lys Val Gln Ala Asp Leu Tyr Phe His Asp Leu Lys Phe
                        340                 345                 350
    Asp Gly Ala Phe Ile Ile Asn Trp Leu Glu Arg Asn Gly Phe Lys Trp
                        355                 360                 365
    Ser Ala Asp Gly Leu Pro Asn Thr Tyr Asn Thr Ile Ile Ser Arg Met
                        370                 375                 380
    Gly Gln Trp Tyr Met Ile Asp Ile Cys Leu Gly Tyr Lys Gly Lys Arg
    385                 390                 395                 400
    Lys Ile His Thr Val Ile Tyr Asp Ser Leu Lys Lys Leu Pro Phe Pro
                        405                 410                 415
    Val Lys Lys Ile Ala Lys Asp Phe Lys Leu Thr Val Leu Lys Gly Asp
                        420                 425                 430
    Ile Asp Tyr His Lys Glu Arg Pro Val Gly Tyr Lys Ile Thr Pro Glu
                        435                 440                 445
    Glu Tyr Ala Tyr Ile Lys Asn Asp Ile Gln Ile Ala Glu Ala Leu
            450                 455                 460
    Leu Ile Gln Phe Lys Gln Gly Leu Asp Arg Met Thr Ala Gly Ser Asp
    465                 470                 475                 480
    Ser Leu Lys Gly Phe Lys Asp Ile Ile Thr Thr Lys Lys Phe Lys Lys
                        485                 490                 495
    Val Phe Pro Thr Leu Ser Leu Gly Leu Asp Lys Glu Val Arg Tyr Ala
                        500                 505                 510
    Tyr Arg Gly Gly Phe Thr Trp Leu Asn Asp Arg Phe Lys Glu Lys Glu
                        515                 520                 525
    Ile Gly Glu Gly Met Val Phe Asp Val Asn Ser Leu Tyr Pro Ala Gln
                        530                 535                 540
    Met Tyr Ser Arg Leu Leu Pro Tyr Gly Glu Pro Ile Val Phe Glu Gly
    545                 550                 555                 560
    Lys Tyr Val Trp Asp Glu Asp Tyr Pro Leu His Ile Gln His Ile Arg
                        565                 570                 575
```

```
Cys Glu Phe Glu Leu Lys Glu Gly Tyr Ile Pro Thr Ile Gln Ile Lys
                580                 585                 590

Arg Ser Arg Phe Tyr Lys Gly Asn Glu Tyr Leu Lys Ser Ser Gly Gly
            595                 600                 605

Glu Ile Ala Asp Leu Trp Leu Ser Asn Val Asp Leu Glu Leu Met Lys
        610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                645                 650                 655

Ile Lys Thr Thr Ser Glu Gly Ala Ile Lys Gln Leu Ala Lys Arg Met
                660                 665                 670

Leu Asn Ser Leu Tyr Gly Lys Phe Ala Ser Asn Pro Asp Val Thr Gly
            675                 680                 685

Lys Val Pro Tyr Leu Lys Glu Asn Gly Ala Leu Gly Phe Arg Leu Gly
        690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                725                 730                 735

Asp Arg Ile Ile Tyr Cys Asp Thr Asp Ser Ile His Leu Thr Gly Thr
                740                 745                 750

Glu Ile Pro Asp Val Ile Lys Asp Ile Val Asp Pro Lys Lys Leu Gly
            755                 760                 765

Tyr Trp Ala His Glu Ser Thr Phe Lys Arg Ala Lys Tyr Leu Arg Gln
        770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
                805                 810                 815

Cys Ala Gly Met Thr Asp Lys Ile Lys Lys Glu Val Thr Phe Glu Asn
                820                 825                 830

Phe Lys Val Gly Phe Ser Arg Lys Met Lys Pro Lys Pro Val Gln Val
            835                 840                 845

Pro Gly Gly Val Val Leu Val Asp Asp Thr Phe Thr Ile Lys
        850                 855                 860

<210> SEQ ID NO 9
<211> LENGTH: 862
<212> TYPE: PRT
<213> ORGANISM: Artificial
<220> FEATURE:
<223> OTHER INFORMATION: GST, His, and S-tagged E486A-N62D mutant Phi29
      polymerase

<400> SEQUENCE: 9

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
```

```
                65                  70                  75                  80
        Met Leu Gly Gly Cys Pro Lys Glu Arg Ala Glu Ile Ser Met Leu Glu
                        85                  90                  95

Gly Ala Val Leu Asp Ile Arg Tyr Gly Val Ser Arg Ile Ala Tyr Ser
                       100                 105                 110

Lys Asp Phe Glu Thr Leu Lys Val Asp Phe Leu Ser Lys Leu Pro Glu
                       115                 120                 125

Met Leu Lys Met Phe Glu Asp Arg Leu Cys His Lys Thr Tyr Leu Asn
                   130                 135                 140

Gly Asp His Val Thr His Pro Asp Phe Met Leu Tyr Asp Ala Leu Asp
        145                 150                 155                 160

Val Val Leu Tyr Met Asp Pro Met Cys Leu Asp Ala Phe Pro Lys Leu
                       165                 170                 175

Val Cys Phe Lys Lys Arg Ile Glu Ala Ile Pro Gln Ile Asp Lys Tyr
                       180                 185                 190

Leu Lys Ser Ser Lys Tyr Ile Ala Trp Pro Leu Gln Gly Trp Gln Ala
                       195                 200                 205

Thr Phe Gly Gly Gly Asp His Pro Pro Lys Ser Asp Gly Ser Thr Ser
                   210                 215                 220

Gly Ser Gly His His His His His His Ser Ala Gly Leu Val Pro Arg
        225                 230                 235                 240

Gly Ser Thr Ala Ile Gly Met Lys Glu Thr Ala Ala Ala Lys Phe Glu
                       245                 250                 255

Arg Gln His Met Asp Ser Pro Asp Leu Gly Thr Gly Gly Gly Ser Gly
                       260                 265                 270

Asp Asp Asp Asp Lys Ser Pro Met Gly Tyr Arg Gly Ser Glu Phe Met
                   275                 280                 285

Lys His Met Pro Arg Lys Met Tyr Ser Cys Asp Phe Glu Thr Thr Thr
                   290                 295                 300

Lys Val Glu Asp Cys Arg Val Trp Ala Tyr Gly Tyr Met Asn Ile Glu
        305                 310                 315                 320

Asp His Ser Glu Tyr Lys Ile Gly Asn Ser Leu Asp Glu Phe Met Ala
                       325                 330                 335

Trp Val Leu Lys Val Gln Ala Asp Leu Tyr Phe His Asp Leu Lys Phe
                       340                 345                 350

Asp Gly Ala Phe Ile Ile Asn Trp Leu Glu Arg Asn Gly Phe Lys Trp
                       355                 360                 365

Ser Ala Asp Gly Leu Pro Asn Thr Tyr Asn Thr Ile Ile Ser Arg Met
                   370                 375                 380

Gly Gln Trp Tyr Met Ile Asp Ile Cys Leu Gly Tyr Lys Gly Lys Arg
        385                 390                 395                 400

Lys Ile His Thr Val Ile Tyr Asp Ser Leu Lys Lys Leu Pro Phe Pro
                       405                 410                 415

Val Lys Lys Ile Ala Lys Asp Phe Lys Leu Thr Val Leu Lys Gly Asp
                       420                 425                 430

Ile Asp Tyr His Lys Glu Arg Pro Val Gly Tyr Lys Ile Thr Pro Glu
                       435                 440                 445

Glu Tyr Ala Tyr Ile Lys Asn Asp Ile Gln Ile Ala Glu Ala Leu
                       450                 455                 460

Leu Ile Gln Phe Lys Gln Gly Leu Asp Arg Met Thr Ala Gly Ser Asp
        465                 470                 475                 480

Ser Leu Lys Gly Phe Lys Asp Ile Ile Thr Thr Lys Lys Phe Lys Lys
                       485                 490                 495
```

Val Phe Pro Thr Leu Ser Leu Gly Leu Asp Lys Glu Val Arg Tyr Ala
            500                 505                 510

Tyr Arg Gly Gly Phe Thr Trp Leu Asn Asp Arg Phe Lys Glu Lys Glu
            515                 520                 525

Ile Gly Glu Gly Met Val Phe Asp Val Asn Ser Leu Tyr Pro Ala Gln
            530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
            565                 570                 575

Cys Glu Phe Glu Leu Lys Glu Gly Tyr Ile Pro Thr Ile Gln Ile Lys
            580                 585                 590

Arg Ser Arg Phe Tyr Lys Gly Asn Glu Tyr Leu Lys Ser Ser Gly Gly
            595                 600                 605

Glu Ile Ala Asp Leu Trp Leu Ser Asn Val Asp Leu Glu Leu Met Lys
            610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
            645                 650                 655

Ile Lys Thr Thr Ser Glu Gly Ala Ile Lys Gln Leu Ala Lys Leu Met
            660                 665                 670

Leu Asn Ser Leu Tyr Gly Lys Phe Ala Ser Asn Pro Asp Val Thr Gly
            675                 680                 685

Lys Val Pro Tyr Leu Lys Glu Asn Gly Ala Leu Gly Phe Arg Leu Gly
            690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
            725                 730                 735

Asp Arg Ile Ile Tyr Cys Asp Thr Asp Ser Ile His Leu Thr Gly Thr
            740                 745                 750

Glu Ile Pro Asp Val Ile Lys Asp Ile Val Asp Pro Lys Lys Leu Gly
            755                 760                 765

Tyr Trp Ala His Ala Ser Thr Phe Lys Arg Ala Lys Tyr Leu Arg Gln
            770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
            805                 810                 815

Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
            835                 840                 845

Pro Gly Gly Val Val Leu Val Asp Asp Thr Phe Thr Ile Lys
            850                 855                 860

<210> SEQ ID NO 10
<211> LENGTH: 862
<212> TYPE: PRT
<213> ORGANISM: Artificial
<220> FEATURE:
<223> OTHER INFORMATION: GST, His, and S-tagged E486D-N62D mutant Phi29
      polymerase

<400> SEQUENCE: 10

```
Met Ser Pro Ile Leu Gly Tyr Trp Lys Ile Lys Gly Leu Val Gln Pro
 1               5                  10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Gly Ser Thr Ser
    210                 215                 220
Gly Ser Gly His His His His His His Ser Ala Gly Leu Val Pro Arg
225                 230                 235                 240
Gly Ser Thr Ala Ile Gly Met Lys Glu Thr Ala Ala Ala Lys Phe Glu
                245                 250                 255
Arg Gln His Met Asp Ser Pro Asp Leu Gly Thr Gly Gly Gly Ser Gly
            260                 265                 270
Asp Asp Asp Asp Lys Ser Pro Met Gly Tyr Arg Gly Ser Glu Phe Met
        275                 280                 285
Lys His Met Pro Arg Lys Met Tyr Ser Cys Asp Phe Glu Thr Thr Thr
    290                 295                 300
Lys Val Glu Asp Cys Arg Val Trp Ala Tyr Gly Tyr Met Asn Ile Glu
305                 310                 315                 320
Asp His Ser Glu Tyr Lys Ile Gly Asn Ser Leu Asp Glu Phe Met Ala
                325                 330                 335
Trp Val Leu Lys Val Gln Ala Asp Leu Tyr Phe His Asp Leu Lys Phe
            340                 345                 350
Asp Gly Ala Phe Ile Ile Asn Trp Leu Glu Arg Asn Gly Phe Lys Trp
        355                 360                 365
Ser Ala Asp Gly Leu Pro Asn Thr Tyr Asn Thr Ile Ile Ser Arg Met
    370                 375                 380
Gly Gln Trp Tyr Met Ile Asp Ile Cys Leu Gly Tyr Lys Gly Lys Arg
385                 390                 395                 400
Lys Ile His Thr Val Ile Tyr Asp Ser Leu Lys Lys Leu Pro Phe Pro
                405                 410                 415
```

```
Val Lys Lys Ile Ala Lys Asp Phe Lys Leu Thr Val Leu Lys Gly Asp
            420                 425                 430

Ile Asp Tyr His Lys Glu Arg Pro Val Gly Tyr Lys Ile Thr Pro Glu
        435                 440                 445

Glu Tyr Ala Tyr Ile Lys Asn Asp Ile Gln Ile Ala Glu Ala Leu
    450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Phe Lys Lys
                485                 490                 495

Val Phe Pro Thr Leu Ser Leu Gly Leu Asp Lys Glu Val Arg Tyr Ala
                500                 505                 510

Tyr Arg Gly Gly Phe Thr Trp Leu Asn Asp Arg Phe Lys Glu Lys Glu
        515                 520                 525

Ile Gly Glu Gly Met Val Phe Asp Val Asn Ser Leu Tyr Pro Ala Gln
    530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
                565                 570                 575

Cys Glu Phe Glu Leu Lys Glu Gly Tyr Ile Pro Thr Ile Gln Ile Lys
            580                 585                 590

Arg Ser Arg Phe Tyr Lys Gly Asn Glu Tyr Leu Lys Ser Ser Gly Gly
        595                 600                 605

Glu Ile Ala Asp Leu Trp Leu Ser Asn Val Asp Leu Glu Leu Met Lys
    610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                645                 650                 655

Ile Lys Thr Thr Ser Glu Gly Ala Ile Lys Gln Leu Ala Lys Leu Met
            660                 665                 670

Leu Asn Ser Leu Tyr Gly Lys Phe Ala Ser Asn Pro Asp Val Thr Gly
        675                 680                 685

Lys Val Pro Tyr Leu Lys Glu Asn Gly Ala Leu Gly Phe Arg Leu Gly
    690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                725                 730                 735

Asp Arg Ile Ile Tyr Cys Asp Thr Asp Ser Ile His Leu Thr Gly Thr
            740                 745                 750

Glu Ile Pro Asp Val Ile Lys Asp Ile Val Asp Pro Lys Lys Leu Gly
        755                 760                 765

Tyr Trp Ala His Asp Ser Thr Phe Lys Arg Ala Lys Tyr Leu Arg Gln
    770                 775                 780

Lys Thr Tyr Ile Gln Asp Ile Tyr Met Lys Glu Val Asp Gly Lys Leu
785                 790                 795                 800

Val Glu Gly Ser Pro Asp Asp Tyr Thr Asp Ile Lys Phe Ser Val Lys
                805                 810                 815

Cys Ala Gly Met Thr Asp Lys Ile Lys Lys Glu Val Thr Phe Glu Asn
            820                 825                 830
```

```
Phe Lys Val Gly Phe Ser Arg Lys Met Lys Pro Lys Pro Val Gln Val
                835                 840                 845

Pro Gly Gly Val Val Leu Val Asp Asp Thr Phe Thr Ile Lys
        850                 855                 860

<210> SEQ ID NO 11
<211> LENGTH: 862
<212> TYPE: PRT
<213> ORGANISM: Artificial
<220> FEATURE:
<223> OTHER INFORMATION: GST, His, and S-tagged K512A-N62D mutant Phi29
      polymerase

<400> SEQUENCE: 11

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ser Pro Met Gly Tyr Arg Gly Ser Glu Phe Met
        275                 280                 285

Lys His Met Pro Arg Lys Met Tyr Ser Cys Asp Phe Glu Thr Thr Thr
    290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335
```

```
Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
            355                 360                 365

Ser Ala Asp Gly Leu Pro Asn Thr Tyr Asn Thr Ile Ile Ser Arg Met
370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Lys Asp Phe Lys Leu Thr Val Leu Lys Gly Asp
                420                 425                 430

Ile Asp Tyr His Lys Glu Arg Pro Val Gly Tyr Lys Ile Thr Pro Glu
                435                 440                 445

Glu Tyr Ala Tyr Ile Lys Asn Asp Ile Gln Ile Ala Glu Ala Leu
            450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
                485                 490                 495

Val Phe Pro Thr Leu Ser Leu Gly Leu Asp Lys Glu Val Arg Tyr Ala
            500                 505                 510

Tyr Arg Gly Gly Phe Thr Trp Leu Asn Asp Arg Phe Lys Glu Lys Glu
            515                 520                 525

Ile Gly Glu Gly Met Val Phe Asp Val Asn Ser Leu Tyr Pro Ala Gln
            530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
                565                 570                 575

Cys Glu Phe Glu Leu Lys Glu Gly Tyr Ile Pro Thr Ile Gln Ile Lys
            580                 585                 590

Arg Ser Arg Phe Tyr Lys Gly Asn Glu Tyr Leu Lys Ser Ser Gly Gly
    595                 600                 605

Glu Ile Ala Asp Leu Trp Leu Ser Asn Val Asp Leu Glu Leu Met Lys
610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                645                 650                 655

Ile Lys Thr Thr Ser Glu Gly Ala Ile Lys Gln Leu Ala Lys Leu Met
                660                 665                 670

Leu Asn Ser Leu Tyr Gly Lys Phe Ala Ser Asn Pro Asp Val Thr Gly
                675                 680                 685

Lys Val Pro Tyr Leu Lys Glu Asn Gly Ala Leu Gly Phe Arg Leu Gly
            690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                725                 730                 735

Asp Arg Ile Ile Tyr Cys Asp Thr Asp Ser Ile His Leu Thr Gly Thr
            740                 745                 750
```

```
Glu Ile Pro Asp Val Ile Lys Asp Ile Val Asp Pro Lys Leu Gly
            755                 760                 765

Tyr Trp Ala His Glu Ser Thr Phe Lys Arg Ala Lys Tyr Leu Arg Gln
770                 775                 780

Lys Thr Tyr Ile Gln Asp Ile Tyr Met Lys Glu Val Asp Gly Ala Leu
785                 790                 795                 800

Val Glu Gly Ser Pro Asp Asp Tyr Thr Asp Ile Lys Phe Ser Val Lys
                805                 810                 815

Cys Ala Gly Met Thr Asp Lys Ile Lys Lys Glu Val Thr Phe Glu Asn
            820                 825                 830

Phe Lys Val Gly Phe Ser Arg Lys Met Lys Pro Lys Pro Val Gln Val
            835                 840                 845

Pro Gly Gly Val Val Leu Val Asp Asp Thr Phe Thr Ile Lys
    850                 855                 860

<210> SEQ ID NO 12
<211> LENGTH: 845
<212> TYPE: PRT
<213> ORGANISM: Artificial
<220> FEATURE:
<223> OTHER INFORMATION: GST, His, and S-tagged N62D mutant Phi29
      polymerase with deletion of residues 505-525

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255
```

```
Arg Gln His Met Asp Ser Pro Asp Leu Gly Thr Gly Gly Ser Gly
            260                 265                 270

Asp Asp Asp Lys Ser Pro Met Gly Tyr Arg Gly Ser Glu Phe Met
            275                 280                 285

Lys His Met Pro Arg Lys Met Tyr Ser Cys Asp Phe Glu Thr Thr Thr
290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
            355                 360                 365

Ser Ala Asp Gly Leu Pro Asn Thr Tyr Asn Thr Ile Ile Ser Arg Met
370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Lys Asp Phe Lys Leu Thr Val Leu Lys Gly Asp
            420                 425                 430

Ile Asp Tyr His Lys Glu Arg Pro Val Gly Tyr Lys Ile Thr Pro Glu
            435                 440                 445

Glu Tyr Ala Tyr Ile Lys Asn Asp Ile Gln Ile Ile Ala Glu Ala Leu
            450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
                485                 490                 495

Val Phe Pro Thr Leu Ser Leu Gly Leu Asp Lys Glu Val Arg Tyr Ala
            500                 505                 510

Tyr Arg Gly Gly Phe Thr Trp Leu Asn Asp Arg Phe Lys Glu Lys Glu
            515                 520                 525

Ile Gly Glu Gly Met Val Phe Asp Val Asn Ser Leu Tyr Pro Ala Gln
            530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
                565                 570                 575

Cys Glu Phe Glu Leu Lys Glu Gly Tyr Ile Pro Thr Ile Gln Ile Lys
            580                 585                 590

Arg Ser Arg Phe Tyr Lys Gly Asn Glu Tyr Leu Lys Ser Ser Gly Gly
            595                 600                 605

Glu Ile Ala Asp Leu Trp Leu Ser Asn Val Asp Leu Glu Leu Met Lys
            610                 615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                645                 650                 655

Ile Lys Thr Thr Ser Glu Gly Ala Ile Lys Gln Leu Ala Lys Leu Met
            660                 665                 670
```

```
Leu Asn Ser Leu Tyr Gly Lys Phe Ala Ser Asn Pro Asp Val Thr Gly
            675                 680                 685

Lys Val Pro Tyr Leu Lys Glu Asn Gly Ala Leu Gly Phe Arg Leu Gly
        690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Gln Ala Cys Tyr
                725                 730                 735

Asp Arg Ile Ile Tyr Cys Asp Thr Asp Ser Ile His Leu Thr Gly Thr
                740                 745                 750

Glu Ile Pro Asp Val Ile Lys Asp Ile Val Asp Pro Lys Lys Leu Gly
            755                 760                 765

Tyr Trp Ala His Glu Ser Thr Phe Lys Arg Ala Lys Tyr Leu Arg Gln
        770                 775                 780

Lys Thr Tyr Ile Gln Asp Ile Lys Asp Gly Glu Phe Ser Val Lys Cys
785                 790                 795                 800

Ala Gly Met Thr Asp Lys Ile Lys Lys Glu Val Thr Phe Glu Asn Phe
                805                 810                 815

Lys Val Gly Phe Ser Arg Lys Met Lys Pro Lys Pro Val Gln Val Pro
            820                 825                 830

Gly Gly Val Val Leu Val Asp Asp Thr Phe Thr Ile Lys
        835                 840                 845

<210> SEQ ID NO 13
<211> LENGTH: 843
<212> TYPE: PRT
<213> ORGANISM: Artificial
<220> FEATURE:
<223> OTHER INFORMATION: GST, His, and S-tagged N62D mutant Phi29
      polymerase with deletion of residues 505-525

<400> SEQUENCE: 13

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
                260                 265                 270

Asp Asp Asp Lys Ser Pro Met Gly Tyr Arg Gly Ser Glu Phe Met
        275                 280                 285

Lys His Met Pro Arg Lys Met Tyr Ser Cys Asp Phe Glu Thr Thr Thr
        290                 295                 300

Lys Val Glu Asp Cys Arg Val Trp Ala Tyr Gly Tyr Met Asn Ile Glu
305                 310                 315                 320

Asp His Ser Glu Tyr Lys Ile Gly Asn Ser Leu Asp Glu Phe Met Ala
                325                 330                 335

Trp Val Leu Lys Val Gln Ala Asp Leu Tyr Phe His Asp Leu Lys Phe
            340                 345                 350

Asp Gly Ala Phe Ile Ile Asn Trp Leu Glu Arg Asn Gly Phe Lys Trp
            355                 360                 365

Ser Ala Asp Gly Leu Pro Asn Thr Tyr Asn Thr Ile Ile Ser Arg Met
    370                 375                 380

Gly Gln Trp Tyr Met Ile Asp Ile Cys Leu Gly Tyr Lys Gly Lys Arg
385                 390                 395                 400

Lys Ile His Thr Val Ile Tyr Asp Ser Leu Lys Lys Leu Pro Phe Pro
                405                 410                 415

Val Lys Lys Ile Ala Lys Asp Phe Lys Leu Thr Val Leu Lys Gly Asp
            420                 425                 430

Ile Asp Tyr His Lys Glu Arg Pro Val Gly Tyr Lys Ile Thr Pro Glu
        435                 440                 445

Glu Tyr Ala Tyr Ile Lys Asn Asp Ile Gln Ile Ile Ala Glu Ala Leu
    450                 455                 460

Leu Ile Gln Phe Lys Gln Gly Leu Asp Arg Met Thr Ala Gly Ser Asp
465                 470                 475                 480

Ser Leu Lys Gly Phe Lys Asp Ile Ile Thr Thr Lys Lys Phe Lys Lys
                485                 490                 495

Val Phe Pro Thr Leu Ser Leu Gly Leu Asp Lys Glu Val Arg Tyr Ala
            500                 505                 510

Tyr Arg Gly Gly Phe Thr Trp Leu Asn Asp Arg Phe Lys Glu Lys Glu
        515                 520                 525

Ile Gly Glu Gly Met Val Phe Asp Val Asn Ser Leu Tyr Pro Ala Gln
    530                 535                 540

Met Tyr Ser Arg Leu Leu Pro Tyr Gly Glu Pro Ile Val Phe Glu Gly
545                 550                 555                 560

Lys Tyr Val Trp Asp Glu Asp Tyr Pro Leu His Ile Gln His Ile Arg
                565                 570                 575

Cys Glu Phe Glu Leu Lys Glu Gly Tyr Ile Pro Thr Ile Gln Ile Lys
            580                 585                 590

Arg Ser Arg Phe Tyr Lys Gly Asn Glu Tyr Leu Lys Ser Ser Gly Gly
        595                 600                 605
```

Glu Ile Ala Asp Leu Trp Leu Ser Asn Val Asp Glu Leu Met Lys
610             615                 620

Glu His Tyr Asp Leu Tyr Asn Val Glu Tyr Ile Ser Gly Leu Lys Phe
625                 630                 635                 640

Lys Ala Thr Thr Gly Leu Phe Lys Asp Phe Ile Asp Lys Trp Thr Tyr
                645                 650                 655

Ile Lys Thr Thr Ser Glu Gly Ala Ile Lys Gln Leu Ala Lys Leu Met
                660                 665                 670

Leu Asn Ser Leu Tyr Gly Lys Phe Ala Ser Asn Pro Asp Val Thr Gly
            675                 680                 685

Lys Val Pro Tyr Leu Lys Glu Asn Gly Ala Leu Gly Phe Arg Leu Gly
690                 695                 700

Glu Glu Glu Thr Lys Asp Pro Val Tyr Thr Pro Met Gly Val Phe Ile
705                 710                 715                 720

Thr Ala Trp Ala Arg Tyr Thr Thr Ile Thr Ala Ala Gln Ala Cys Tyr
                725                 730                 735

Asp Arg Ile Ile Tyr Cys Asp Thr Asp Ser Ile His Leu Thr Gly Thr
                740                 745                 750

Glu Ile Pro Asp Val Ile Lys Asp Ile Val Asp Pro Lys Lys Leu Gly
755                 760                 765

Tyr Trp Ala His Glu Ser Thr Phe Lys Arg Ala Lys Tyr Leu Arg Gln
770                 775                 780

Lys Thr Tyr Ile Gln Asp Ile Asp Gly Phe Ser Val Lys Cys Ala Gly
785                 790                 795                 800

Met Thr Asp Lys Ile Lys Lys Glu Val Thr Phe Glu Asn Phe Lys Val
                805                 810                 815

Gly Phe Ser Arg Lys Met Lys Pro Lys Pro Val Gln Val Pro Gly Gly
                820                 825                 830

Val Val Leu Val Asp Asp Thr Phe Thr Ile Lys
                835                 840

<210> SEQ ID NO 14
<211> LENGTH: 7667
<212> TYPE: DNA
<213> ORGANISM: Artificial
<220> FEATURE:
<223> OTHER INFORMATION: plasmide encoding N62D mutant Phi29 polymerase

<400> SEQUENCE: 14
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaagccg tttctgtaat gaaggagaaa     660
actcaccgag gcagttccat aggatggcaa gatcctggta tcggtctgcg attccgactc     720

```
gtccaacatc aatacaacct attaatttcc cctcgtcaaa aataaggtta tcaagtgaga    780
aatcaccatg agtgacgact gaatccggtg agaatggcaa aagtttatgc atttcttttcc   840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200
cttttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tatttttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagactttta  3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
```

```
ccgccagcct agccgggtcc tcaacgacag gagcacgatc atgctagtca tgccccgcgc   3180
ccaccggaag gagctgactg ggttgaaggc tctcaagggc atcggtcgag atcccggtgc   3240
ctaatgagtg agctaactta cattaattgc gttgcgctca ctgcccgctt tccagtcggg   3300
aaacctgtcg tgccagctgc attaatgaat cggccaacgc gcggggagag gcggtttgcg   3360
tattgggcgc cagggtggtt tttcttttca ccagtgagac gggcaacagc tgattgccct   3420
tcaccgcctg gccctgagag agttgcagca agcggtccac gctggtttgc cccagcaggc   3480
gaaaatcctg tttgatggtg gttaacggcg ggatataaca tgagctgtct cggtatcgt   3540 cgtatcccac taccgagatg tccgcaccaa cgcgcagccc ggactcggta atggcgcgca   3600
ttgcgcccag cgccatctga tcgttggcaa ccagcatcgc agtgggaacg atgccctcat   3660
tcagcatttg catggtttgt tgaaaaccgg acatggcact ccagtcgcct tcccgttccg   3720
ctatcggctg aatttgattg cgagtgagat atttatgcca gccagcagca gcagacgcg   3780 ccgagacaga acttaatggg cccgctaaca gcgcgatttg ctggtgaccc aatgcgacca   3840
gatgctccac gcccagtcgc gtaccgtctt catgggagaa aataatactg ttgatgggtg   3900
tctggtcaga gacatcaaga aataacgccg gaacattagt gcaggcagct tccacagcaa   3960
tggcatcctg gtcatccagc ggatagttaa tgatcagccc actgacgcgt tgcgcgagaa   4020
gattgtgcac cgccgcttta caggcttcga cgccgcttcg ttctaccatc gacaccacca   4080
cgctggcacc cagttgatcg gcgcgagatt taatcgccgc gacaatttgc gacggcgcgt   4140
gcagggccag actggaggtg gcaacgccaa tcagcaacga ctgtttgccc gccagttgtt   4200
gtgccacgcg gttgggaatg taattcagct ccgccatcgc cgcttccact ttttcccgcg   4260
ttttcgcaga aacgtggctg gcctggttca ccacgcggga aacggtctga taagagacac   4320
cggcatactc tgcgacatcg tataacgtta ctggtttcac attcaccacc ctgaattgac   4380
tctcttccgg gcgctatcat gccataccgc gaaaggtttt gcgccattcg atggtgtccg   4440
ggatctcgac gctctccctt atgcgactcc tgcattagga agcagcccag tagtaggttg   4500
aggccgttga gcaccgccgc cgcaaggaat ggtgcatgca aggagatggc gcccaacagt   4560
cccccggcca cggggcctgc caccatacccc acgccgaaac aagcgctcat gagcccgaag   4620
tggcgagccc gatcttcccc atcggtgatg tcggcgatat aggcgccagc aaccgcacct   4680
gtggcgccgc tgatgccggc cacgatgcgt ccggcgtaga ggatcgagat cgatctcgat   4740
cccgcgaaat taatacgact cactataggg gaattgtgag cggataacaa ttcccctcta   4800
gaaataattt tgtttaactt taagaaggag atatacatat gtcccctata ctaggttatt   4860
ggaaaattaa gggccttgtg caacccactc gacttctttt ggaatatctt gaagaaaaat   4920
atgaagagca tttgtatgag cgcgatgaag gtgataaatg gcgaaacaaa agtttgaat   4980 tgggtttgga gtttcccaat cttccttatt atattgatgg tgatgttaaa ttaacacagt   5040
ctatggccat catacgttat atagctgaca agcacaacat gttgggtggt tgtccaaaag   5100
agcgtgcaga gatttcaatg cttgaaggag cggttttgga tattagatac ggtgtttcga   5160
gaattgcata tagtaaagac tttgaaactc tcaaagttga ttttcttagc aagctacctg   5220
aaatgctgaa aatgttcgaa gatcgtttat gtcataaaac atatttaaat ggtgatcatg   5280
taacccatcc tgacttcatg ttgtatgacg ctcttgatgt tgttttatac atggacccaa   5340
tgtgcctgga tgcgttccca aaattagttt gttttaaaaa acgtattgaa gctatcccac   5400
aaattgataa gtacttgaaa tccagcaagt atatagcatg cctttgcag ggctggcaag   5460
```

```
ccacgtttgg tggtggcgac catcctccaa aatcggatgg ttcaactagt ggttctggtc   5520
atcaccatca ccatcactcc gcgggtctgg tgccacgcgg tagtactgca attggtatga   5580
aagaaaccgc tgctgctaaa ttcgaacgcc agcacatgga cagcccagat ctgggtaccg   5640
gtggtggctc cggtgatgac gacgacaaga gtcccatggg atatcgggga tccgaattca   5700
tgaagcatat gccgagaaag atgtatagtt gtgactttga caactactact aaagtggaag   5760
actgtagggt atgggcgtat ggttatatga atatagaaga tcacagtgag tacaaaatag   5820
gtaatagcct ggatgagttt atggcgtggg tgttgaaggt acaagctgat ctatatttcc   5880
atgatctcaa atttgacgga gcttttatca ttaactggtt ggaacgtaat ggttttaagt   5940
ggtcggctga cggattgcca aacacatata atacgatcat atctcgcatg ggacaatggt   6000
acatgattga tatatgttta ggctacaaag gaaacgtaa gatacataca gtgatatatg   6060
acagcttaaa gaaactaccg tttcctgtta agaagatagc taaagacttt aaactaactg   6120
ttcttaaagg tgatattgat taccacaaag aaagaccagt cggctataag ataacacccg   6180
aagaatacgc ctatattaaa aacgatattc agattattgc ggaagctctg ttaattcagt   6240
ttaagcaagg tttagaccgg atgacagcag gcagtgacag tctaaaaggt ttcaaggata   6300
ttataaccac taagaaattc aaaaaggtgt ttcctacatt gagtcttgga ctcgataagg   6360
aagtgagata cgcctataga ggtggtttta catggttaaa tgataggttc aaagaaaaag   6420
aaatcggaga aggcatggtc ttcgatgtta atagtctata tcctgcacag atgtatagtc   6480
gtctccttcc atatggtgaa cctatagtat tcgagggtaa atacgtttgg gacgaagatt   6540
acccactaca catacagcat atcagatgtg agttcgaatt gaaagagggc tatatacccag   6600
ctatacagat aaaaagaagt aggttttata aaggtaatga gtacctaaaa agtagcggcg   6660
gggagatagc cgacctctgg ttgtcaaatg tagacctaga attaatgaaa gaacactacg   6720
atttatataa cgttgaatat atcagcggct taaaatttaa agcaactaca ggtttgttta   6780
aagattttat agataaatgg acgtacatca agacgacatc agaaggagcg atcaagcaac   6840
tagcaaaact gatgttaaac agtctatacg gtaaattcgc tagtaaccct gatgttacag   6900
ggaaagtccc ttatttaaaa gagaatgggg cgctaggttt cagacttgga gaagaggaaa   6960
caaaagaccc tgtttataca cctatgggcg ttttcatcac tgcatgggct agatacacga   7020
caattacagc ggcacaggct tgttatgatc ggataatata ctgtgatact gacagcatac   7080
atttaacggg tacagagata cctgatgtaa taaaagatat agttgaccct aagaaattgg   7140
gatactgggc acatgaaagt acattcaaaa gagctaaata tctgagacag aagacccta   7200
tacaagacat ctatatgaaa gaagtagatg gtaagttagt agaaggtagt ccagatgatt   7260
acactgatat aaaatttagt gttaaatgtg cggaatgac tgacaagatt aagaaagagg   7320
ttacgtttga gaatttcaaa gtcggattca gtcggaaaat gaagcctaag cctgtgcaag   7380
tgccgggcgg ggtggttctg gttgatgaca cattcacaat caaataagaa ttctgtacag   7440
gccttggcgc gcctgcaggc gagctccgtc gacaagcttg cggccgcact cgagcaccac   7500
caccaccacc accaccacta attgattaat acctaggctg ctaaacaaag cccgaaagga   7560
agctgagttg gctgctgcca ccgctgagca ataactagca tacccccttg gggcctctaa   7620
acgggtcttg aggggttttt tgctgaaagg aggaactata tccggat        7667
```

<210> SEQ ID NO 15
<211> LENGTH: 1728
<212> TYPE: DNA
<213> ORGANISM: Artificial
<220> FEATURE:
<223> OTHER INFORMATION: encodes K135A-N62D mutant Phi29 polymerase

<400> SEQUENCE: 15

```
atgaagcaca tgccgagaaa gatgtatagt tgtgactttg agacaactac taaagtggaa      60
gactgtaggg tatgggcgta tggttatatg aatatagaag atcacagtga gtacaaaata     120
ggtaatagcc tggatgagtt tatggcgtgg gtgttgaagg tacaagctga tctatatttc     180
catgatctca aatttgacgg agcttttatc attaactggt tggaacgtaa tggttttaag     240
tggtcggctg acggattgcc aaacacatat aatacgatca tatctcgcat gggacaatgg     300
tacatgattg atatatgttt aggctacaaa gggaaacgta agatacatac agtgatatat     360
gacagcttaa agaaactacc gtttcctgtt aagaagatag ctgccgactt taaactaact     420
gttcttaaag gtgatattga ttaccacaaa gaaagaccag tcggctataa gataacaccc     480
gaagaatacg cctatattaa aaacgatatt cagattattg cggaagctct gttaattcag     540
tttaagcaag gtttagaccg gatgacagca ggcagtgaca gtctaaaagg tttcaaggat     600
attataacca ctaagaaatt caaaaaggtg tttcctacat tgagtcttgg actcgataag     660
gaagtgagat acgcctatag aggtggtttt acatggttaa atgataggtt caaagaaaaa     720
gaaatcggag aaggcatggt cttcgatgtt aatagtctat atcctgcaca gatgtatagt     780
cgtctccttc catacggtga acctatagta ttcgagggta atacgtttg ggacgaagat     840
tacccactac acatacagca tatcagatgt gagttcgaat gaaagaggg ctatataccc     900
actatacaga taaaaagaag taggttttat aaaggtaatg agtacctaaa aagtagcggc     960
ggggagatag ccgacctctg gttgtcaaat gtagacctag aattaatgaa agaacactac    1020
gatttatata cgttgaata tatcagcggc ttaaaattta aagcaactac aggtttgttt    1080
aaagatttta tagataaatg gacgtacatc aagacgacat cagaaggagc gatcaagcaa    1140
ctagcaaaac tgatgttaaa cagtctatac ggtaaattcg ctagtaaccc tgatgttaca    1200
gggaaagtcc cttatttaaa agagaatggg gcgctaggtt tcagacttgg agaagaggaa    1260
acaaaagacc ctgtttatac acctatgggc gttttcatca ctgcatgggc tagatacacg    1320
acaattacag cggcacaggc ttgttatgat cggatatat actgtgatac tgacagcata    1380
catttaacgg gtacagagat acctgatgta ataaagata tagttgaccc taagaaattg    1440
ggatactggg cacatgaaag tacattcaaa agagctaaat atctgagaca gaagacctat    1500
atacaagaca tctatatgaa agaagtagat ggtaagttag tagaaggtag tccagatgat    1560
tacactgata taaaatttag tgttaaatgt gcgggaatga ctgacaagat taagaaagag    1620
gttacgtttg agaatttcaa agtcggattc agtcggaaaa tgaagcctaa gcctgtgcaa    1680
gtgccgggcg gggtggttct ggttgatgac acattcacaa tcaaataa                 1728
```

<210> SEQ ID NO 16
<211> LENGTH: 1728
<212> TYPE: DNA
<213> ORGANISM: Artificial
<220> FEATURE:
<223> OTHER INFORMATION: encodes E375H-N62D mutant Phi29 polymerase

<400> SEQUENCE: 16

```
atgaagcaca tgccgagaaa gatgtatagt tgtgactttg agacaactac taaagtggaa      60
gactgtaggg tatgggcgta tggttatatg aatatagaag atcacagtga gtacaaaata     120
ggtaatagcc tggatgagtt tatggcgtgg gtgttgaagg tacaagctga tctatatttc     180
```

```
catgatctca aatttgacgg agcttttatc attaactggt tggaacgtaa tggtttaag    240 tggtcggctg acggattgcc aaacacatat aatacgatca tatctcgcat gggacaatgg   300
tacatgattg atatatgttt aggctacaaa gggaaacgta agatacatac agtgatatat   360
gacagcttaa agaaactacc gtttcctgtt aagaagatag ctaaagactt taaactaact   420
gttcttaaag gtgatattga ttaccacaaa gaaagaccag tcggctataa gataacaccc   480
gaagaatacg cctatattaa aaacgatatt cagattattg cggaagctct gttaattcag   540
tttaagcaag gtttagaccg gatgacagca ggcagtgaca gtctaaaagg tttcaaggat   600
attataacca ctaagaaatt caaaaaggtg tttcctacat gagtcttgg actcgataag    660 gaagtgagat acgcctatag aggtggtttt acatggttaa atgataggtt caaagaaaaa   720
gaaatcggag aaggcatggt cttcgatgtt aatagtctat atcctgcaca gatgtatagt   780
cgtctccttc catacggtga acctatagta ttcgagggta aatacgtttg ggacgaagat   840
tacccactac acatacagca tatcagatgt gagttcgaat tgaaagaggg ctatataccc   900
actatacaga taaaaagaag taggtttat aaaggtaatg agtacctaaa aagtagcggc    960
ggggagatag ccgacctctg gttgtcaaat gtagacctag aattaatgaa agaacactac  1020
gatttatata acgttgaata tatcagcggc ttaaaattta agcaactac aggtttgttt   1080 aaagattta tagataatg acgtacatc aagacgacat cacacggagc gatcaagcaa    1140
ctagcaaaac tgatgttaaa cagtctatac ggtaaattcg ctagtaaccc tgatgttaca  1200
gggaaagtcc cttatttaaa agagaatggg gcgctaggtt tcagacttgg agaagaggaa  1260
acaaaagacc ctgtttatac acctatgggc gttttcatca ctgcatgggc tagatacacg  1320
acaattacag cggcacaggc ttgttatgat cggataatat actgtgatac tgacagcata  1380
catttaacgg gtacagagat acctgatgta ataaaagata tagttgaccc taagaaattg  1440
ggatactggg cacatgaaag tacattcaaa agagctaaat atctgagaca gaagacctat  1500
atacaagaca tctatatgaa agaagtagat ggtaagttag tagaaggtag tccagatgat  1560
tacactgata taaaatttag tgttaaatgt gcgggaatga ctgacaagat taagaaagag  1620
gttacgtttg agaatttcaa agtcggattc agtcggaaaa tgaagcctaa gcctgtgcaa  1680
gtgccgggcg gggtggttct ggttgatgac acattcacaa tcaaataa              1728
```

<210> SEQ ID NO 17
<211> LENGTH: 1728
<212> TYPE: DNA
<213> ORGANISM: Artificial
<220> FEATURE:
<223> OTHER INFORMATION: encodes E375S-N62D mutant Phi29 polymerase

<400> SEQUENCE: 17

```
atgaagcaca tgccgagaaa gatgtatagt tgtgactttg agacaactac taaagtggaa    60
gactgtaggg tatgggcgta tggttatatg aatatagaag atcacagtga gtacaaaata   120
ggtaatagcc tggatgagtt tatggcgtgg gtgttgaagg tacaagctga tctatatttc   180
catgatctca aatttgacgg agcttttatc attaactggt tggaacgtaa tggtttaag    240 tggtcggctg acggattgcc aaacacatat aatacgatca tatctcgcat gggacaatgg   300
tacatgattg atatatgttt aggctacaaa gggaaacgta agatacatac agtgatatat   360
gacagcttaa agaaactacc gtttcctgtt aagaagatag ctaaagactt taaactaact   420
gttcttaaag gtgatattga ttaccacaaa gaaagaccag tcggctataa gataacaccc   480
gaagaatacg cctatattaa aaacgatatt cagattattg cggaagctct gttaattcag   540
```

```
tttaagcaag gtttagaccg gatgacagca ggcagtgaca gtctaaaagg tttcaaggat      600
attataacca ctaagaaatt caaaaaggtg tttcctacat tgagtcttgg actcgataag      660
gaagtgagat acgcctatag aggtggtttt acatggttaa atgataggtt caaagaaaaa      720
gaaatcggag aaggcatggt cttcgatgtt aatagtctat atcctgcaca gatgtatagt      780
cgtctccttc catacggtga acctatagta ttcgagggta aatacgtttg ggacgaagat      840
tacccactac acatacagca tatcagatgt gagttcgaat tgaaagaggg ctatataccc      900
actatacaga taaaaagaag taggttttat aaaggtaatg agtacctaaa aagtagcggc      960
ggggagatag ccgacctctg gttgtcaaat gtagacctag aattaatgaa agaacactac     1020
gatttatata acgttgaata tatcagcggc ttaaaattta agcaactac aggtttgttt     1080 aaagatttta tagataaatg gacgtacatc aagacgacat caagcggagc gatcaagcaa     1140
ctagcaaaac tgatgttaaa cagtctatac ggtaaattcg ctagtaaccc tgatgttaca     1200
gggaaagtcc cttatttaaa agagaatggg gcgctaggtt tcagacttgg agaagaggaa     1260
acaaaagacc ctgtttatac acctatgggc gttttcatca ctgcatgggc tagatacacg     1320
acaattacag cggcacaggc ttgttatgat cggataatat actgtgatac tgacagcata     1380
catttaacgg gtacagagat acctgatgta ataaaagata tagttgaccc taagaaattg     1440
ggatactggg cacatgaaag tacattcaaa agagctaaat atctgagaca gaagacctat     1500
atacaagaca tctatatgaa agaagtagat ggtaagttag tagaaggtag tccagatgat     1560
tacactgata taaaatttag tgttaaatgt gcgggaatga ctgacaagat taagaaagag     1620
gttacgtttg agaatttcaa agtcggattc agtcggaaaa tgaagcctaa gcctgtgcaa     1680
gtgccgggcg gggtggttct ggttgatgac acattcacaa tcaaataa                  1728
```

<210> SEQ ID NO 18
<211> LENGTH: 1728
<212> TYPE: DNA
<213> ORGANISM: Artificial
<220> FEATURE:
<223> OTHER INFORMATION: encodes L384R-N62D mutant Phi29 polymerase

<400> SEQUENCE: 18

```
atgaagcaca tgccgagaaa gatgtatagt tgtgactttg agacaactac taaagtggaa       60
gactgtaggg tatgggcgta tggttatatg aatatagaag atcacagtga gtacaaaata      120
ggtaatagcc tggatgagtt tatggcgtgg gtgttgaagg tacaagctga tctatatttc      180
catgatctca aatttgacgg agcttttatc attaactggt tggaacgtaa tggttttaag      240
tggtcggctg acggattgcc aaacacatat aatacgatca tatctcgcat gggacaatgg      300
tacatgattg atatatgttt aggctacaaa gggaaacgta agatacatac agtgatatat      360
gacagcttaa agaaactacc gtttcctgtt aagaagatag ctaaagactt taaactaact      420
gttcttaaag gtgatattga ttaccacaaa gaaagaccag tcggctataa gataacaccc      480
gaagaatacg cctatattaa aaacgatatt cagattattg cggaagctct gttaattcag      540
tttaagcaag gtttagaccg gatgacagca ggcagtgaca gtctaaaagg tttcaaggat      600
attataacca ctaagaaatt caaaaaggtg tttcctacat tgagtcttgg actcgataag      660
gaagtgagat acgcctatag aggtggtttt acatggttaa atgataggtt caaagaaaaa      720
gaaatcggag aaggcatggt cttcgatgtt aatagtctat atcctgcaca gatgtatagt      780
cgtctccttc catacggtga acctatagta ttcgagggta aatacgtttg ggacgaagat      840
```

|  |  |  |  |  |
|---|---|---|---|---|
| tacccactac | acatacagca | tatcagatgt | gagttcgaat | tgaaagaggg ctatataccc | 900 |
| actatacaga | taaaaagaag | taggtttat | aaaggtaatg | agtacctaaa aagtagcggc | 960 |
| ggggagatag | ccgacctctg | gttgtcaaat | gtagacctag | aattaatgaa agaacactac | 1020 |
| gatttatata | acgttgaata | tatcagcggc | ttaaaattta | aagcaactac aggtttgttt | 1080 |
| aaagatttta | tagataaatg | gacgtacatc | aagacgacat | cagaaggagc gatcaagcaa | 1140 |
| ctagcaaaac | ggatgttaaa | cagtctatac | ggtaaattcg | ctagtaaccc tgatgttaca | 1200 |
| gggaaagtcc | cttatttaaa | agagaatggg | gcgctaggtt | tcagacttgg agaagaggaa | 1260 |
| acaaaagacc | ctgtttatac | acctatgggc | gttttcatca | ctgcatgggc tagatacacg | 1320 |
| acaattacag | cggcacaggc | ttgttatgat | cggataatat | actgtgatac tgacagcata | 1380 |
| catttaacgg | gtacagagat | acctgatgta | ataaaagata | tagttgaccc taagaaattg | 1440 |
| ggatactggg | cacatgaaag | tacattcaaa | agagctaaat | atctgagaca gaagacctat | 1500 |
| atacaagaca | tctatatgaa | agaagtagat | ggtaagttag | tagaaggtag tccagatgat | 1560 |
| tacactgata | taaaatttag | tgttaaatgt | gcgggaatga | ctgacaagat taagaaagag | 1620 |
| gttacgtttg | agaatttcaa | agtcggattc | agtcggaaaa | tgaagcctaa gcctgtgcaa | 1680 |
| gtgccgggcg | gggtggttct | ggttgatgac | acattcacaa | tcaaataa | 1728 |

<210> SEQ ID NO 19
<211> LENGTH: 1728
<212> TYPE: DNA
<213> ORGANISM: Artificial
<220> FEATURE:
<223> OTHER INFORMATION: encodes E486A-N62D mutant Phi29 polymerase

<400> SEQUENCE: 19

|  |  |  |  |  |
|---|---|---|---|---|
| atgaagcaca | tgccgagaaa | gatgtatagt | tgtgactttg | agacaactac taaagtggaa | 60 |
| gactgtaggg | tatgggcgta | tggttatatg | aatatagaag | atcacagtga gtacaaaata | 120 |
| ggtaatagcc | tggatgagtt | tatggcgtgg | gtgttgaagg | tacaagctga tctatatttc | 180 |
| catgatctca | aatttgacgg | agcttttatc | attaactggt | tggaacgtaa tggttttaag | 240 |
| tggtcggctg | acggattgcc | aaacacatat | aatacgatca | tatctcgcat gggacaatgg | 300 |
| tacatgattg | atatatgttt | aggctacaaa | gggaaacgta | agatacatac agtgatatat | 360 |
| gacagcttaa | agaaactacc | gtttcctgtt | aagaagatag | ctaaagactt taaactaact | 420 |
| gttcttaaag | gtgatattga | ttaccacaaa | gaaagaccag | tcggctataa gataacaccc | 480 |
| gaagaatacg | cctatattaa | aaacgatatt | cagattattg | cggaagctct gttaattcag | 540 |
| tttaagcaag | gtttagaccg | gatgacagca | ggcagtgaca | gtctaaaagg tttcaaggat | 600 |
| attataacca | ctaagaaatt | caaaaaggtg | tttcctacat | tgagtcttgg actcgataag | 660 |
| gaagtgagat | acgcctatag | aggtggtttt | acatggttaa | atgataggtt caaagaaaaa | 720 |
| gaaatcggag | aaggcatggt | cttcgatgtt | aatagtctat | atcctgcaca gatgtatagt | 780 |
| cgtctccttc | catacggtga | acctatagta | ttcgagggta | aatacgtttg ggacgaagat | 840 |
| tacccactac | acatacagca | tatcagatgt | gagttcgaat | tgaaagaggg ctatataccc | 900 |
| actatacaga | taaaaagaag | taggtttat | aaaggtaatg | agtacctaaa aagtagcggc | 960 |
| ggggagatag | ccgacctctg | gttgtcaaat | gtagacctag | aattaatgaa agaacactac | 1020 |
| gatttatata | acgttgaata | tatcagcggc | ttaaaattta | aagcaactac aggtttgttt | 1080 |
| aaagatttta | tagataaatg | gacgtacatc | aagacgacat | cagaaggagc gatcaagcaa | 1140 |
| ctagcaaaac | tgatgttaaa | cagtctatac | ggtaaattcg | ctagtaaccc tgatgttaca | 1200 |

```
gggaaagtcc cttatttaaa agagaatggg gcgctaggtt tcagacttgg agaagaggaa    1260
acaaaagacc ctgtttatac acctatgggc gttttcatca ctgcatgggc tagatacacg    1320
acaattacag cggcacaggc ttgttatgat cggataatat actgtgatac tgacagcata    1380
catttaacgg gtacagagat acctgatgta ataaaagata tagttgaccc taagaaattg    1440
ggatactggg cacatgccag tacattcaaa agagctaaat atctgagaca gaagacctat    1500
atacaagaca tctatatgaa agaagtagat ggtaagttag tagaaggtag tccagatgat    1560
tacactgata taaaatttag tgttaaatgt gcgggaatga ctgacaagat taagaaagag    1620
gttacgtttg agaatttcaa agtcggattc agtcggaaaa tgaagcctaa gcctgtgcaa    1680
gtgccgggcg gggtggttct ggttgatgac acattcacaa tcaaataa                 1728
```

<210> SEQ ID NO 20
<211> LENGTH: 1728
<212> TYPE: DNA
<213> ORGANISM: Artificial
<220> FEATURE:
<223> OTHER INFORMATION: encodes E486D-N62D mutant Phi29 polymerase

<400> SEQUENCE: 20

```
atgaagcaca tgccgagaaa gatgtatagt tgtgactttg agacaactac taaagtggaa     60
gactgtaggg tatgggcgta tggttatatg aatatagaag atcacagtga gtacaaaata    120
ggtaatagcc tggatgagtt tatggcgtgg gtgttgaagg tacaagctga tctatatttc    180
catgatctca aatttgacgg agcttttatc attaactggt tggaacgtaa tggttttaag    240
tggtcggctg acggattgcc aaacacatat aatacgatca tatctcgcat gggacaatgg    300
tacatgattg atatatgttt aggctacaaa gggaaacgta agatacatac agtgatatat    360
gacagcttaa agaaactacc gtttcctgtt aagaagatag ctaaagactt taaactaact    420
gttcttaaag gtgatattga ttaccacaaa gaaagaccag tcggctataa gataacaccc    480
gaagaatacg cctatattaa aaacgatatt cagattattg cggaagctct gttaattcag    540
tttaagcaag gttagaccg gatgacagca ggcagtgaca gtctaaaagg tttcaaggat    600
attataacca ctaagaaatt caaaaaggtg tttcctacat tgagtcttgg actcgataag    660
gaagtgagat acgcctatag aggtggtttt acatggttaa atgataggtt caaagaaaaa    720
gaaatcggag aaggcatggt cttcgatgtt aatagtctat atcctgcaca gatgtatagt    780
cgtctccttc catacggtga acctatagta ttcgagggta atacgtttg ggacgaagat    840 tacccactac acatacagca tatcagatgt gagttcgaat tgaaagaggg ctatataccc    900
actatacaga taaaaagaag taggttttat aaaggtaatg agtacctaaa agtagcggc    960 ggggagatag ccgacctctg gttgtcaaat gtagacctag aattaatgaa agaacactac   1020
gatttatata acgttgaata tatcagcggc ttaaaattta aagcaactac aggtttgttt   1080
aaagatttta tagataaatg gacgtacatc aagacgacat cagaaggagc gatcaagcaa   1140
ctagcaaaac tgatgttaaa cagtctatac ggtaaattcg ctagtaaccc tgatgttaca   1200
gggaaagtcc cttatttaaa agagaatggg gcgctaggtt tcagacttgg agaagaggaa   1260
acaaaagacc ctgtttatac acctatgggc gttttcatca ctgcatgggc tagatacacg   1320
acaattacag cggcacaggc ttgttatgat cggataatat actgtgatac tgacagcata   1380
catttaacgg gtacagagat acctgatgta ataaaagata tagttgaccc taagaaattg   1440
ggatactggg cacatgacag tacattcaaa agagctaaat atctgagaca gaagacctat   1500
```

```
atacaagaca tctatatgaa agaagtagat ggtaagttag tagaaggtag tccagatgat    1560
tacactgata taaaatttag tgttaaatgt gcgggaatga ctgacaagat taagaaagag    1620
gttacgtttg agaatttcaa agtcggattc agtcggaaaa tgaagcctaa gcctgtgcaa    1680
gtgccgggcg gggtggttct ggttgatgac acattcacaa tcaaataa                 1728
```

<210> SEQ ID NO 21
<211> LENGTH: 1728
<212> TYPE: DNA
<213> ORGANISM: Artificial
<220> FEATURE:
<223> OTHER INFORMATION: encodes K512A-N62D mutant Phi29 polymerase

<400> SEQUENCE: 21

```
atgaagcaca tgccgagaaa gatgtatagt tgtgactttg agacaactac taaagtggaa     60
gactgtaggg tatgggcgta tggttatatg aatatagaag atcacagtga gtacaaaata    120
ggtaatagcc tggatgagtt tatggcgtgg gtgttgaagg tacaagctga tctatatttc    180
catgatctca aatttgacgg agcttttatc attaactggt tggaacgtaa tggttttaag    240
tggtcggctg acggattgcc aaacacatat aatacgatca tatctcgcat gggacaatgg    300
tacatgattg atatatgttt aggctacaaa gggaaacgta agatacatac agtgatatat    360
gacagcttaa agaaactacc gtttcctgtt aagaagatag ctaaagactt taaactaact    420
gttcttaaag gtgatattga ttaccacaaa gaaagaccag tcggctataa gataacaccc    480
gaagaatacg cctatattaa aaacgatatt cagattattg cggaagctct gttaattcag    540
tttaagcaag gtttagaccg gatgacagca ggcagtgaca gtctaaaagg tttcaaggat    600
attataacca ctaagaaatt caaaaaggtg tttcctacat tgagtcttgg actcgataag    660
gaagtgagat acgcctatag aggtggtttt acatggttaa atgataggtt caaagaaaaa    720
gaaatcggag aaggcatggt cttcgatgtt aatagtctat atcctgcaca gatgtatagt    780
cgtctccttc catacggtga acctatagta ttcgagggta aatacgtttg ggacgaagat    840
tacccactac acatacagca tatcagatgt gagttcgaat tgaaagaggg ctatatacc     900 actatacaga taaaaagaag taggtttttat aaaggtaatg agtacctaaa aagtagcggc    960
ggggagatag ccgacctctg gttgtcaaat gtagacctag aattaatgaa agaacactac    1020
gatttatata acgttgaata tatcagcggc ttaaaattta aagcaactac aggtttgttt    1080
aaagatttta tagataaatg gacgtacatc aagacgacat cagaaggagc gatcaagcaa    1140
ctagcaaaac tgatgttaaa cagtctatac ggtaaattcg ctagtaaccc tgatgttaca    1200
gggaaagtcc cttatttaaa agagaatggg gcgctaggtt tcagacttgg agaagaggaa    1260
acaaaagacc ctgtttatac acctatgggc gttttcatca ctgcatgggc tagatacacg    1320
acaattacag cggcacaggc ttgttatgat cggataatat actgtgatac tgacagcata    1380
catttaacgg gtacagagat acctgatgta ataaaagata tagttgaccc taagaaattg    1440
ggatactggg cacatgaaag tacattcaaa agagctaaat atctgagaca gaagacctat    1500
atacaagaca tctatatgaa agaagtagat ggtgccttag tagaaggtag tccagatgat    1560
tacactgata taaaatttag tgttaaatgt gcgggaatga ctgacaagat taagaaagag    1620
gttacgtttg agaatttcaa agtcggattc agtcggaaaa tgaagcctaa gcctgtgcaa    1680
gtgccgggcg gggtggttct ggttgatgac acattcacaa tcaaataa                 1728
```

<210> SEQ ID NO 22
<211> LENGTH: 1677

<212> TYPE: DNA
<213> ORGANISM: Artificial
<220> FEATURE:
<223> OTHER INFORMATION: encodes N62D mutant Phi29 polymerase with deletion of residues 505-525

<400> SEQUENCE: 22

| | |
|---|---|
| atgaagcaca tgccgagaaa gatgtatagt tgtgactttg agacaactac taaagtggaa | 60 |
| gactgtaggg tatgggcgta tggttatatg aatatagaag atcacagtga gtacaaaata | 120 |
| ggtaatagcc tggatgagtt tatggcgtgg gtgttgaagg tacaagctga tctatatttc | 180 |
| catgatctca aatttgacgg agcttttatc attaactggt tggaacgtaa tggttttaag | 240 |
| tggtcggctg acggattgcc aaacacatat aatacgatca tatctcgcat gggacaatgg | 300 |
| tacatgattg atatatgttt aggctacaaa gggaaacgta agatacatac agtgatatat | 360 |
| gacagcttaa agaaactacc gtttcctgtt aagaagatag ctaaagactt taaactaact | 420 |
| gttcttaaag gtgatattga ttaccacaaa gaaagaccag tcggctataa gataacaccc | 480 |
| gaagaatacg cctatattaa aaacgatatt cagattattg cggaagctct gttaattcag | 540 |
| tttaagcaag gtttagaccg gatgacagca ggcagtgaca gtctaaaagg tttcaaggat | 600 |
| attataacca ctaagaaatt caaaaaggtg tttcctacat tgagtcttgg actcgataag | 660 |
| gaagtgagat acgcctatag aggtggtttt acatggttaa atgataggtt caaagaaaaa | 720 |
| gaaatcggag aaggcatggt cttcgatgtt aatagtctat atcctgcaca gatgtatagt | 780 |
| cgtctccttc catacggtga acctatagta ttcgagggta aatacgtttg ggacgaagat | 840 |
| tacccactac acatacagca tatcagatgt gagttcgaat tgaaagaggg ctatataccc | 900 |
| actatacaga taaaaagaag taggttttat aaaggtaatg agtacctaaa aagtagcggc | 960 |
| ggggagatag ccgacctctg gttgtcaaat gtagacctag aattaatgaa agaacactac | 1020 |
| gatttatata acgttgaata tatcagcggc ttaaaattta agcaactac aggtttgttt | 1080 |
| aaagatttta tagataaatg gacgtacatc aagacgacat cagaaggagc gatcaagcaa | 1140 |
| ctagcaaaac tgatgttaaa cagtctatac ggtaaattcg ctagtaaccc tgatgttaca | 1200 |
| gggaaagtcc cttatttaaa agagaatggg gcgctaggtt tcagacttgg agaagaggaa | 1260 |
| acaaaagacc ctgtttatac acctatgggc gttttcatca ctgcatgggc tagatacacg | 1320 |
| acaattacag cggcacaggc ttgttatgat cggataatat actgtgatac tgacagcata | 1380 |
| catttaacgg gtacagagat acctgatgta ataaaagata tagttgaccc taagaaattg | 1440 |
| ggatactggg cacatgaaag tacattcaaa agagctaaat atctgagaca gaagacctat | 1500 |
| atacaagaca tcaaggatgg agagtttagt gttaaatgtg cgggaatgac tgacaagatt | 1560 |
| aagaaagagg ttacgtttga gaatttcaaa gtcggattca gtcggaaaat gaagcctaag | 1620 |
| cctgtgcaag tgccgggcgg ggtggttctg gttgatgaca cattcacaat caaataa | 1677 |

<210> SEQ ID NO 23
<211> LENGTH: 1671
<212> TYPE: DNA
<213> ORGANISM: Artificial
<220> FEATURE:
<223> OTHER INFORMATION: encodes N62D mutant Phi29 polymerase with deletion of residues 505-525

<400> SEQUENCE: 23

| | |
|---|---|
| atgaagcaca tgccgagaaa gatgtatagt tgtgactttg agacaactac taaagtggaa | 60 |
| gactgtaggg tatgggcgta tggttatatg aatatagaag atcacagtga gtacaaaata | 120 |

| | | |
|---|---|---|
| ggtaatagcc tggatgagtt tatggcgtgg gtgttgaagg tacaagctga tctatatttc | 180 |
| catgatctca aatttgacgg agctttatc attaactggt tggaacgtaa tggttttaag | 240 |
| tggtcggctg acggattgcc aaacacatat aatacgatca tatctcgcat gggacaatgg | 300 |
| tacatgattg atatatgttt aggctacaaa gggaaacgta agatacatac agtgatatat | 360 |
| gacagcttaa agaaactacc gtttcctgtt aagaagatag ctaaagactt taaactaact | 420 |
| gttcttaaag gtgatattga ttaccacaaa gaaagaccag tcggctataa gataacaccc | 480 |
| gaagaatacg cctatattaa aaacgatatt cagattattg cggaagctct gttaattcag | 540 |
| tttaagcaag gtttagaccg gatgacagca ggcagtgaca gtctaaaagg tttcaaggat | 600 |
| attataacca ctaagaaatt caaaaaggtg tttcctacat tgagtcttgg actcgataag | 660 |
| gaagtgagat acgcctatag aggtggtttt acatggttaa atgataggtt caagaaaaaa | 720 |
| gaaatcggag aaggcatggt cttcgatgtt aatagtctat atcctgcaca gatgtatagt | 780 |
| cgtctccttc atacggtga acctatagta ttcgagggta aatacgtttg ggacgaagat | 840 |
| tacccactac acatacagca tatcagatgt gagttcgaat tgaaagaggg ctatataccc | 900 |
| actatacaga taaaaagaag taggttttat aaaggtaatg agtacctaaa agtagcggc | 960 |
| ggggagatag ccgacctctg gttgtcaaat gtagacctag aattaatgaa agaacactac | 1020 |
| gatttatata acgttgaata tatcagcggc ttaaaattta agcaactac aggtttgttt | 1080 |
| aaagatttta tagataaatg gacgtacatc aagacgacat cagaaggagc gatcaagcaa | 1140 |
| ctagcaaaac tgatgttaaa cagtctatac ggtaaattcg ctagtaaccc tgatgttaca | 1200 |
| gggaaagtcc cttatttaaa agagaatggg gcgctaggtt tcagacttgg agaagaggaa | 1260 |
| acaaaagacc ctgtttatac acctatgggc gttttcatca ctgcatgggc tagatacacg | 1320 |
| acaattacag cggcacaggc ttgttatgat cggataatat actgtgatac tgacagcata | 1380 |
| catttaacgg gtacagagat acctgatgta ataaagata tagttgaccc taagaaattg | 1440 |
| ggatactggg cacatgaaag tacattcaaa agagctaaat atctgagaca gaagacctat | 1500 |
| atacaagaca tcgacggctt tagtgttaaa tgtgcgggaa tgactgacaa gattaagaaa | 1560 |
| gaggttacgt ttgagaattt caaagtcgga ttcagtcgga aaatgaagcc taagcctgtg | 1620 |
| caagtgccgg gcggggtggt tctggttgat gacacattca caatcaaata a | 1671 |

<210> SEQ ID NO 24
<211> LENGTH: 575
<212> TYPE: PRT
<213> ORGANISM: Artificial
<220> FEATURE:
<223> OTHER INFORMATION: K135A-N62D mutant Phi29 polymerase

<400> SEQUENCE: 24

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asp Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95
```

```
Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Ala Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510
```

```
Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 25
<211> LENGTH: 575
<212> TYPE: PRT
<213> ORGANISM: Artificial
<220> FEATURE:
<223> OTHER INFORMATION: E375H-N62D mutant Phi29 polymerase

<400> SEQUENCE: 25

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300
```

```
Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser His Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 26
<211> LENGTH: 575
<212> TYPE: PRT
<213> ORGANISM: Artificial
<220> FEATURE:
<223> OTHER INFORMATION: E375S-N62D mutant Phi29 polymerase

<400> SEQUENCE: 26

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asp Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
            85                  90                  95
```

```
Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
        355                 360                 365

Tyr Ile Lys Thr Thr Ser Ser Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
        500                 505                 510

Leu Val Glu Gly Ser Pro Asp Asp Tyr Thr Asp Ile Lys Phe Ser Val
```

```
            515                 520                 525
Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Leu Val Asp Asp Thr Phe Thr Ile Lys
                565                 570                 575

<210> SEQ ID NO 27
<211> LENGTH: 575
<212> TYPE: PRT
<213> ORGANISM: Artificial
<220> FEATURE:
<223> OTHER INFORMATION: E375K-N62D mutant Phi29 polymerase

<400> SEQUENCE: 27

Met Lys His Met Pro Arg Lys Met Tyr Ser Cys Asp Phe Glu Thr Thr
1               5                  10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
```

```
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Lys Gly Ala Ile Lys Gln Leu Ala Lys Leu
                370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Thr Lys Asp Pro Val Tyr Thr Pro Met Gly Val Phe
                420                 425                 430
Ile Thr Ala Trp Ala Arg Tyr Thr Thr Ile Thr Ala Ala Gln Ala Cys
                435                 440                 445
Tyr Asp Arg Ile Ile Tyr Cys Asp Thr Asp Ser Ile His Leu Thr Gly
                450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
                500                 505                 510
Leu Val Glu Gly Ser Pro Asp Asp Tyr Thr Asp Ile Lys Phe Ser Val
                515                 520                 525
Lys Cys Ala Gly Met Thr Asp Lys Ile Lys Lys Glu Val Thr Phe Glu
                530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575

<210> SEQ ID NO 28
<211> LENGTH: 575
<212> TYPE: PRT
<213> ORGANISM: Artificial
<220> FEATURE:
<223> OTHER INFORMATION: E375R-N62D mutant Phi29 polymerase

<400> SEQUENCE: 28

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
                20                  25                  30
Glu Asp His Ser Glu Tyr Lys Ile Gly Asn Ser Leu Asp Glu Phe Met
                35                  40                  45
Ala Trp Val Leu Lys Val Gln Ala Asp Leu Tyr Phe His Asp Leu Lys
50                  55                  60
Phe Asp Gly Ala Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Cys Leu Gly Tyr Lys Gly Lys
```

```
                100             105             110
Arg Lys Ile His Thr Val Ile Tyr Asp Ser Leu Lys Lys Leu Pro Phe
            115                 120                 125
Pro Val Lys Lys Ile Ala Lys Asp Phe Lys Leu Thr Val Leu Lys Gly
            130                 135             140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
            195                 200                 205
Lys Val Phe Pro Thr Leu Ser Leu Gly Leu Asp Lys Glu Val Arg Tyr
            210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
            275                 280                 285
Arg Cys Glu Phe Glu Leu Lys Glu Gly Tyr Ile Pro Thr Ile Gln Ile
            290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
            355                 360                 365
Tyr Ile Lys Thr Thr Ser Arg Gly Ala Ile Lys Gln Leu Ala Lys Leu
            370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
            435                 440                 445
Tyr Asp Arg Ile Ile Tyr Cys Asp Thr Asp Ser Ile His Leu Thr Gly
            450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
            500                 505                 510
Leu Val Glu Gly Ser Pro Asp Asp Tyr Thr Asp Ile Lys Phe Ser Val
            515                 520                 525
```

```
Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
            565                 570                 575

<210> SEQ ID NO 29
<211> LENGTH: 575
<212> TYPE: PRT
<213> ORGANISM: Artificial
<220> FEATURE:
<223> OTHER INFORMATION: L384R-N62D mutant Phi29 polymerase

<400> SEQUENCE: 29

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320
```

```
Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Arg
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 30
<211> LENGTH: 575
<212> TYPE: PRT
<213> ORGANISM: Artificial
<220> FEATURE:
<223> OTHER INFORMATION: E486A-N62D mutant Phi29 polymerase

<400> SEQUENCE: 30

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110
```

-continued

```
Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Ala Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525
```

-continued

```
Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 31
<211> LENGTH: 575
<212> TYPE: PRT
<213> ORGANISM: Artificial
<220> FEATURE:
<223> OTHER INFORMATION: E486D-N62D mutant Phi29 polymerase

<400> SEQUENCE: 31

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320
```

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Asp Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 32
<211> LENGTH: 575
<212> TYPE: PRT
<213> ORGANISM: Artificial
<220> FEATURE:
<223> OTHER INFORMATION: K512A-N62D mutant Phi29 polymerase

<400> SEQUENCE: 32

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

```
Arg Lys Ile His Thr Val Ile Tyr Asp Ser Leu Lys Lys Leu Pro Phe
            115                 120                 125
Pro Val Lys Lys Ile Ala Lys Asp Phe Lys Leu Thr Val Leu Lys Gly
        130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
        195                 200                 205
Lys Val Phe Pro Thr Leu Ser Leu Gly Leu Asp Lys Glu Val Arg Tyr
        210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
        275                 280                 285
Arg Cys Glu Phe Glu Leu Lys Glu Gly Tyr Ile Pro Thr Ile Gln Ile
        290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
        355                 360                 365
Tyr Ile Lys Thr Thr Ser Glu Gly Ala Ile Lys Gln Leu Ala Lys Leu
        370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
        435                 440                 445
Tyr Asp Arg Ile Ile Tyr Cys Asp Thr Asp Ser Ile His Leu Thr Gly
        450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Ala
            500                 505                 510
Leu Val Glu Gly Ser Pro Asp Asp Tyr Thr Asp Ile Lys Phe Ser Val
        515                 520                 525
Lys Cys Ala Gly Met Thr Asp Lys Ile Lys Lys Glu Val Thr Phe Glu
```

-continued

```
                530             535             540
Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 33
<211> LENGTH: 558
<212> TYPE: PRT
<213> ORGANISM: Artificial
<220> FEATURE:
<223> OTHER INFORMATION: N62D mutant Phi29 polymerase with deletion of
      residues 505-525

<400> SEQUENCE: 33

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320
```

```
Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
        340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Lys Asp Gly Glu Phe Ser Val Lys
        500                 505                 510

Cys Ala Gly Met Thr Asp Lys Ile Lys Lys Glu Val Thr Phe Glu Asn
            515                 520                 525

Phe Lys Val Gly Phe Ser Arg Lys Met Lys Pro Lys Pro Val Gln Val
        530                 535                 540

Pro Gly Gly Val Val Leu Val Asp Asp Thr Phe Thr Ile Lys
545                 550                 555

<210> SEQ ID NO 34
<211> LENGTH: 556
<212> TYPE: PRT
<213> ORGANISM: Artificial
<220> FEATURE:
<223> OTHER INFORMATION: N62D mutant Phi29 polymerase with deletion of
      residues 505-525

<400> SEQUENCE: 34

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
            85                  90                  95

Met Gly Gln Trp Tyr Met Ile Asp Ile Cys Leu Gly Tyr Lys Gly Lys
        100                 105                 110

Arg Lys Ile His Thr Val Ile Tyr Asp Ser Leu Lys Lys Leu Pro Phe
    115                 120                 125
```

```
Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Asp Gly Phe Ser Val Lys Cys Ala
            500                 505                 510

Gly Met Thr Asp Lys Ile Lys Lys Glu Val Thr Phe Glu Asn Phe Lys
        515                 520                 525

Val Gly Phe Ser Arg Lys Met Lys Pro Lys Pro Val Gln Val Pro Gly
    530                 535                 540
```

Gly Val Val Leu Val Asp Asp Thr Phe Thr Ile Lys
545                 550                 555

<210> SEQ ID NO 35
<211> LENGTH: 35
<212> TYPE: PRT
<213> ORGANISM: Bacteriophage phi-29

<400> SEQUENCE: 35

Thr Tyr Ile Gln Asp Ile Tyr Met Lys Glu Val Asp Gly Lys Leu Val
1               5                   10                  15

Glu Gly Ser Pro Asp Asp Tyr Thr Asp Ile Lys Phe Ser Val Lys Cys
            20                  25                  30

Ala Gly Met
        35

<210> SEQ ID NO 36
<211> LENGTH: 35
<212> TYPE: PRT
<213> ORGANISM: Bacteriophage B103

<400> SEQUENCE: 36

Thr Tyr Ile Gln Asp Ile Tyr Ala Lys Glu Val Asp Gly Lys Leu Ile
1               5                   10                  15

Glu Cys Ser Pro Asp Glu Ala Thr Thr Thr Lys Phe Ser Val Lys Cys
            20                  25                  30

Ala Gly Met
        35

<210> SEQ ID NO 37
<211> LENGTH: 35
<212> TYPE: PRT
<213> ORGANISM: Bacteriophage PZA

<400> SEQUENCE: 37

Thr Tyr Ile Gln Asp Ile Tyr Met Lys Glu Val Asp Gly Lys Leu Val
1               5                   10                  15

Glu Gly Ser Pro Asp Asp Tyr Thr Thr Ile Lys Phe Ser Val Lys Cys
            20                  25                  30

Ala Gly Met
        35

<210> SEQ ID NO 38
<211> LENGTH: 35
<212> TYPE: PRT
<213> ORGANISM: Bacteriophage M2

<400> SEQUENCE: 38

Thr Tyr Ile Gln Asp Ile Tyr Val Lys Glu Val Asp Gly Lys Leu Lys
1               5                   10                  15

Glu Cys Ser Pro Asp Glu Ala Thr Thr Thr Lys Phe Ser Val Lys Cys
            20                  25                  30

Ala Gly Met
        35

<210> SEQ ID NO 39
<211> LENGTH: 36
<212> TYPE: PRT
<213> ORGANISM: Bacteriophage G1

<400> SEQUENCE: 39

```
Thr Tyr Phe Ile Glu Thr Thr Trp Lys Glu Asn Asp Lys Gly Lys Leu
1               5                   10                  15

Val Val Cys Glu Pro Gln Asp Ala Thr Lys Val Lys Pro Lys Ile Ala
            20                  25                  30

Cys Ala Gly Met
        35

<210> SEQ ID NO 40
<211> LENGTH: 22
<212> TYPE: PRT
<213> ORGANISM: Bacteriophage CP-1

<400> SEQUENCE: 40

Leu Tyr Ile Glu Glu Leu Ile Gln Glu Asp Gly Thr Thr His Leu Asp
1               5                   10                  15

Val Lys Gly Ala Gly Met
            20

<210> SEQ ID NO 41
<211> LENGTH: 45
<212> TYPE: PRT
<213> ORGANISM: Bacteriophage phi-29

<400> SEQUENCE: 41

Leu Lys Phe Lys Ala Thr Thr Gly Leu Phe Lys Asp Phe Ile Asp Lys
1               5                   10                  15

Trp Thr Tyr Ile Lys Thr Thr Ser Glu Gly Ala Ile Lys Gln Leu Ala
            20                  25                  30

Lys Leu Met Leu Asn Ser Leu Tyr Gly Lys Phe Ala Ser
        35                  40                  45

<210> SEQ ID NO 42
<211> LENGTH: 45
<212> TYPE: PRT
<213> ORGANISM: Bacteriophage B103

<400> SEQUENCE: 42

Phe Lys Phe Arg Glu Lys Thr Gly Leu Phe Lys Glu Phe Ile Asp Lys
1               5                   10                  15

Trp Thr Tyr Val Lys Thr His Glu Lys Gly Ala Lys Lys Gln Leu Ala
            20                  25                  30

Lys Leu Met Phe Asp Ser Leu Tyr Gly Lys Phe Ala Ser
        35                  40                  45

<210> SEQ ID NO 43
<211> LENGTH: 45
<212> TYPE: PRT
<213> ORGANISM: Bacteriophage PZA

<400> SEQUENCE: 43

Leu Lys Phe Lys Ala Thr Thr Gly Leu Phe Lys Asp Phe Ile Asp Lys
1               5                   10                  15

Trp Thr His Ile Lys Thr Thr Ser Glu Gly Ala Ile Lys Gln Leu Ala
            20                  25                  30

Lys Leu Met Leu Asn Ser Leu Tyr Gly Lys Phe Ala Ser
        35                  40                  45

<210> SEQ ID NO 44
<211> LENGTH: 45
<212> TYPE: PRT
<213> ORGANISM: Bacteriophage M2
```

<400> SEQUENCE: 44

Phe Lys Phe Arg Glu Lys Thr Gly Leu Phe Lys Asp Phe Ile Asp Lys
1               5                   10                  15

Trp Thr Tyr Val Lys Thr His Glu Glu Gly Ala Lys Lys Gln Leu Ala
            20                  25                  30

Lys Leu Met Leu Asn Ser Leu Tyr Gly Lys Phe Ala Ser
        35                  40                  45

<210> SEQ ID NO 45
<211> LENGTH: 47
<212> TYPE: PRT
<213> ORGANISM: Bacteriophage G1

<400> SEQUENCE: 45

Phe Met Phe Lys Gly Phe Ile Gly Phe Phe Asp Glu Tyr Ile Asp Arg
1               5                   10                  15

Phe Met Glu Ile Lys Asn Ser Pro Asp Ser Ser Ala Glu Gln Ser Leu
            20                  25                  30

Gln Ala Lys Leu Met Leu Asn Ser Leu Tyr Gly Lys Phe Ala Thr
        35                  40                  45

<210> SEQ ID NO 46
<211> LENGTH: 46
<212> TYPE: PRT
<213> ORGANISM: Bacteriophage CP-1

<400> SEQUENCE: 46

Leu Glu Phe Gln Thr Glu Ser Asp Leu Phe Asp Asp Tyr Ile Thr Thr
1               5                   10                  15

Tyr Arg Tyr Lys Lys Glu Asn Ala Gln Ser Pro Ala Glu Lys Gln Lys
            20                  25                  30

Ala Lys Ile Met Leu Asn Ser Leu Tyr Gly Lys Phe Gly Ala
        35                  40                  45

<210> SEQ ID NO 47
<211> LENGTH: 13
<212> TYPE: PRT
<213> ORGANISM: Bacteriophage phi-29

<400> SEQUENCE: 47

Gly Tyr Trp Ala His Glu Ser Thr Phe Lys Arg Ala Lys
1               5                   10

<210> SEQ ID NO 48
<211> LENGTH: 13
<212> TYPE: PRT
<213> ORGANISM: Bacteriophage B103

<400> SEQUENCE: 48

Gly Tyr Trp Ala His Glu Ser Thr Phe Lys Arg Ala Lys
1               5                   10

<210> SEQ ID NO 49
<211> LENGTH: 13
<212> TYPE: PRT
<213> ORGANISM: Bacteriophage PZA

<400> SEQUENCE: 49

Gly Tyr Trp Ala His Glu Ser Thr Phe Lys Arg Ala Lys
1               5                   10

```
<210> SEQ ID NO 50
<211> LENGTH: 13
<212> TYPE: PRT
<213> ORGANISM: Bacteriophage M2

<400> SEQUENCE: 50

Gly Tyr Trp Ala His Glu Ser Thr Phe Lys Arg Ala Lys
1               5                   10

<210> SEQ ID NO 51
<211> LENGTH: 13
<212> TYPE: PRT
<213> ORGANISM: Bacteriophage G1

<400> SEQUENCE: 51

Gly Tyr Trp Asp His Glu Ala Thr Phe Gln Arg Ala Arg
1               5                   10

<210> SEQ ID NO 52
<211> LENGTH: 13
<212> TYPE: PRT
<213> ORGANISM: Bacteriophage CP-1

<400> SEQUENCE: 52

Gly Lys Trp Ala His Glu Gly Arg Ala Val Lys Ala Lys
1               5                   10

<210> SEQ ID NO 53
<211> LENGTH: 10
<212> TYPE: PRT
<213> ORGANISM: Bacteriophage phi-29

<400> SEQUENCE: 53

Lys Glu Val Asp Gly Lys Leu Val Glu Gly
1               5                   10

<210> SEQ ID NO 54
<211> LENGTH: 10
<212> TYPE: PRT
<213> ORGANISM: Bacteriophage B103

<400> SEQUENCE: 54

Lys Glu Val Asp Gly Lys Leu Ile Glu Cys
1               5                   10

<210> SEQ ID NO 55
<211> LENGTH: 10
<212> TYPE: PRT
<213> ORGANISM: Bacteriophage PZA

<400> SEQUENCE: 55

Lys Glu Val Asp Gly Lys Leu Val Glu Gly
1               5                   10

<210> SEQ ID NO 56
<211> LENGTH: 10
<212> TYPE: PRT
<213> ORGANISM: Bacteriophage M2

<400> SEQUENCE: 56

Lys Glu Val Asp Gly Lys Leu Lys Glu Cys
1               5                   10

<210> SEQ ID NO 57
```

```
<211> LENGTH: 11
<212> TYPE: PRT
<213> ORGANISM: Bacteriophage G1

<400> SEQUENCE: 57

Lys Glu Asn Asp Lys Gly Lys Leu Val Val Cys
1               5                   10

<210> SEQ ID NO 58
<211> LENGTH: 4
<212> TYPE: PRT
<213> ORGANISM: Bacteriophage CP-1

<400> SEQUENCE: 58

Glu Asp Gly Thr
1

<210> SEQ ID NO 59
<211> LENGTH: 10
<212> TYPE: PRT
<213> ORGANISM: Bacteriophage phi-29

<400> SEQUENCE: 59

Val Lys Lys Ile Ala Lys Asp Phe Lys Leu
1               5                   10

<210> SEQ ID NO 60
<211> LENGTH: 10
<212> TYPE: PRT
<213> ORGANISM: Bacteriophage B103

<400> SEQUENCE: 60

Val Lys Lys Ile Ala Lys Asp Phe Gln Leu
1               5                   10

<210> SEQ ID NO 61
<211> LENGTH: 10
<212> TYPE: PRT
<213> ORGANISM: Bacteriophage PZA

<400> SEQUENCE: 61

Val Lys Lys Ile Ala Lys Asp Phe Lys Leu
1               5                   10

<210> SEQ ID NO 62
<211> LENGTH: 10
<212> TYPE: PRT
<213> ORGANISM: Bacteriophage M2

<400> SEQUENCE: 62

Val Lys Lys Ile Ala Lys Asp Phe Gln Leu
1               5                   10

<210> SEQ ID NO 63
<211> LENGTH: 10
<212> TYPE: PRT
<213> ORGANISM: Bacteriophage G1

<400> SEQUENCE: 63

Val Glu Gln Ile Ala Lys Gly Phe Gly Leu
1               5                   10

<210> SEQ ID NO 64
<211> LENGTH: 10
<212> TYPE: PRT
```

```
<213> ORGANISM: Bacteriophage CP-1

<400> SEQUENCE: 64

Ile Ala Thr Met Ala Gly Leu Phe Lys Met
1               5                   10

<210> SEQ ID NO 65
<211> LENGTH: 12
<212> TYPE: DNA
<213> ORGANISM: Artificial Sequence
<220> FEATURE:
<223> OTHER INFORMATION: sequence of exemplary DNA template

<400> SEQUENCE: 65
acgtacgtac gt                                                              12

<210> SEQ ID NO 66
<211> LENGTH: 12
<212> TYPE: DNA
<213> ORGANISM: Artificial Sequence
<220> FEATURE:
<223> OTHER INFORMATION: sequence of exemplary DNA template

<400> SEQUENCE: 66
aaccggttaa cc                                                              12
```